(12) United States Patent
Yu et al.

(10) Patent No.: US 12,024,565 B2
(45) Date of Patent: Jul. 2, 2024

(54) TARGETED CD73 ANTIBODY AND ANTIBODY-DRUG CONJUGATE, AND PREPARATION METHOD THEREFOR AND USES THEREOF

(71) Applicants: FUDAN UNIVERSITY, Shanghai (CN); Bliss Biopharmaceutical (Hangzhou) Co., Ltd., Zhejiang (CN)

(72) Inventors: Ke Yu, Shanghai (CN); Rui Jin, Shanghai (CN); Liang Liu, Shanghai (CN)

(73) Assignees: Fudan University, Shangai (CN); Bliss Biopharmaceutical (Hangzhou) Co., Ltd., Zhejiang (CN)

( * ) Notice: Subject to any disclaimer, the term of this patent is extended or adjusted under 35 U.S.C. 154(b) by 968 days.

(21) Appl. No.: 16/978,995

(22) PCT Filed: Mar. 7, 2019

(86) PCT No.: PCT/CN2019/077369
§ 371 (c)(1),
(2) Date: Sep. 8, 2020

(87) PCT Pub. No.: WO2019/170131
PCT Pub. Date: Sep. 12, 2019

(65) Prior Publication Data
US 2021/0024646 A1   Jan. 28, 2021

(30) Foreign Application Priority Data

Mar. 7, 2018 (CN) .......................... 201810188351.8
May 24, 2018 (CN) .......................... 201810506111.8

(51) Int. Cl.
*A61K 39/395* (2006.01)
*A61K 39/00* (2006.01)
*A61K 47/68* (2017.01)
*A61P 35/00* (2006.01)
*C07K 16/00* (2006.01)
*C07K 16/28* (2006.01)
*C07K 16/40* (2006.01)
*C07K 16/46* (2006.01)

(52) U.S. Cl.
CPC ...... *C07K 16/2896* (2013.01); *A61K 47/6849* (2017.08); *A61K 47/6851* (2017.08); *A61P 35/00* (2018.01); *C07K 16/40* (2013.01); *A61K 2039/505* (2013.01); *A61K 2039/51* (2013.01); *C07K 2317/24* (2013.01); *C07K 2317/56* (2013.01); *C07K 2317/622* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS 10,100,129 B2    10/2018  Lonberg et al.
2018/0127523 A1   5/2018  Hinrichs et al.

FOREIGN PATENT DOCUMENTS

| CN | 107001474 A | 8/2017 | |
| WO | 2016/075099 A1 | 5/2016 | |
| WO | WO-2017064043 A1 * | 4/2017 | ............. A61P 35/00 |
| WO | 2017/100670 A1 | 6/2017 | |
| WO | 2017/149515 A1 | 9/2017 | |

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91. (Year: 1991).*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*
Rabia et al . Understanding and overcoming trade-offs between antibody affinity, specificity, stability and solubility. Biochem Eng J. Sep. 15, 2018:137:365-374. (Year: 2018).*
Allard et al., "The ectonucleotidases CD39 and CD73: Novel checkpoint inhibitor targets," *Immunological Reviews* 276:121-144 (2017).
Supplementary European Search Report for EP 19 76 3891, 10 pages, dated Jan. 20, 2022.

* cited by examiner

*Primary Examiner* — Maher M Haddad
(74) *Attorney, Agent, or Firm* — Seed IP Law Group LLP

(57) ABSTRACT

Disclosed by the present invention are a targeted CD73 antibody and an antibody-drug conjugate (ADC), and a preparation method therefor and application thereof. Further disclosed is a method for preparing the described monoclonal antibody and ADC. The monoclonal antibody and the corresponding ADC disclosed by the present invention can be efficiently and highly specifically combined with purified CD73 protein and CD73 on the surfaces of multiple tumor cells to block the catalytic activity of CD73 enzyme, and have high affinity, low immunogenicity and significant anti-tumor effect.

12 Claims, 36 Drawing Sheets
Specification includes a Sequence Listing.

FIGURE 1A
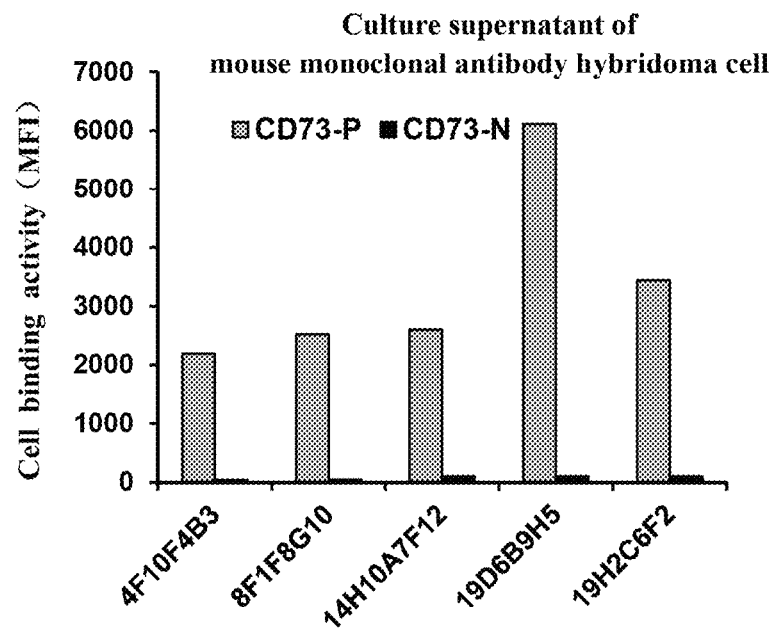
Figure 1B
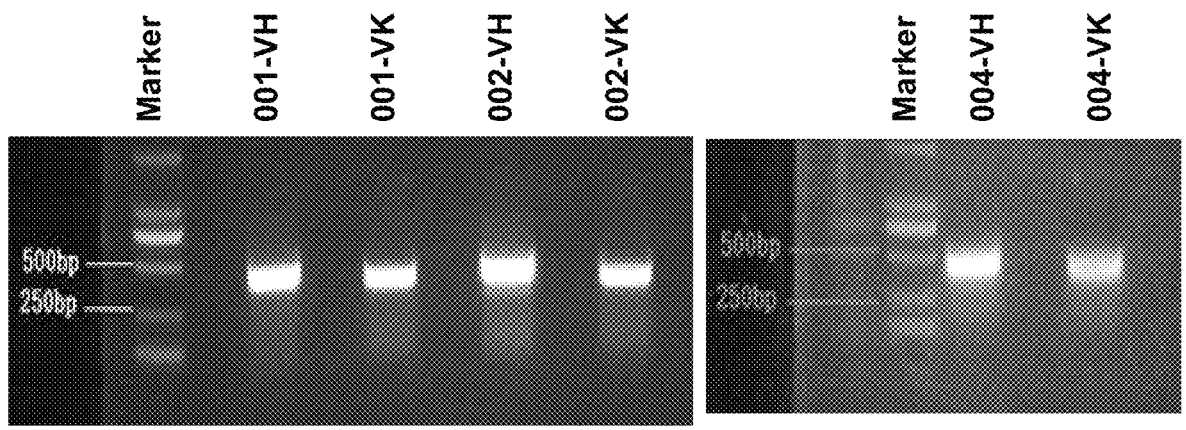
Figure 2

Recombinant human CD73 enzyme activity

| Antibody | Top (%) | Bottom (%) | IC50 (nM) | Antibody | Top (%) | Bottom (%) | IC50 (nM) |
|---|---|---|---|---|---|---|---|
| mAb001c | 97.72 | -0.21 | 0.03 | mAb001c | 95.83 | -8.74 | 0.02 |
| mAb001c-Vk-SGS | 97.16 | -4.75 | 0.02 | mAb001c-VK-SGS | 95.01 | -2.85 | 0.02 |
| Hu001C-14 | 105.10 | -9.23 | 0.08 | Hu001C-14 | 95.18 | -5.31 | 0.06 |
| Hu001C-15 | 95.16 | 3.25 | 0.04 | Hu001C-15 | 96.59 | 3.23 | 0.02 |
| Hu001C-21 | 98.29 | 11.19 | 0.12 | Hu001C-23 | 93.82 | -2.30 | 0.04 |
| Hu001C-22 | 95.88 | 7.96 | 0.03 | Hu001C-24 | 98.90 | 3.56 | 0.03 |
| Hu001C-23 | 95.71 | 5.97 | 0.03 | Hu001C-30 | 97.55 | 18.37 | 0.128 |
| Hu001C-24 | 98.26 | 7.35 | 0.02 | Hu001C-31 | 105.00 | 13.94 | 0.12 |
| Hu001C-25 | 95.83 | 18.08 | 0.30 | Hu001C-32 | 97.50 | 10.27 | 0.07 |
| Hu001C-28 | 98.02 | 11.17 | 0.03 | | | | |

Recombinant human CD73 enzyme activity

| Antibody | Top (%) | Bottom (%) | IC50 (nM) | Antibody | Top (%) | Bottom (%) | IC50 (nM) |
|---|---|---|---|---|---|---|---|
| mAb002c | 91.38 | 0.365 | 0.037 | mAb002c | 93.83 | -1.153 | 0.038 |
| mAb002c-VH-QG,Vk-SG | 98.44 | 2.852 | 0.038 | mAb002c-VH-QG,Vk-SG | 101 | -1.889 | 0.060 |
| Hu002C-2 | 100.3 | 8.091 | 0.042 | Hu002C-10 | 97.66 | 6.071 | 0.059 |
| Hu002C-3 | 91.81 | 7.583 | 0.036 | Hu002C-11 | 92.5 | 5.190 | 0.060 |
| Hu002C-4 | 95.82 | 9.051 | 0.049 | Hu002C-12 | 97.5 | 5.460 | 0.057 |
| Hu002C-6 | 90.89 | 9.703 | 0.064 | Hu002C-14 | 100 | 10.530 | 0.058 |
| Hu002C-7 | 100.9 | 12.680 | 0.028 | Hu002C-15 | 97.71 | 10.180 | 0.075 |
| Hu002C-8 | 94.32 | 7.841 | 0.025 | Hu002C-16 | 100.1 | 10.430 | 0.068 |

Endocytosis of humanized antibody

NCI-H292

MDA-MB-231

| FD114-ADC 3/6 mg/kg | | RBC | HGB | HCT | MCV | MCH | MCHC | RDW | RET |
|---|---|---|---|---|---|---|---|---|---|
| | Day(s) Relative to Start Date | (10^12/L) | (g/L) | (%) | (fL) | (pg) | (g/L) | (%) | (10^9/L) |
| 2101 | -2 | 5.68 | 136 | 41.7 | 73.4 | 24.0 | 327 | 13.0 | 64.9 |
| | 7 | 4.90 | 116 | 35.4 | 72.3 | 23.6 | 326 | 12.8 | 7.5 |
| | 14 | 4.69 | 111 | 34.0 | 72.6 | 23.6 | 325 | 13.4 | 20.8 |
| | 21 | 4.60 | 110 | 34.4 | 74.8 | 23.8 | 319 | 15.7 | 171.6 |
| | 28 | 4.34 | 102 | 31.8 | 73.3 | 23.6 | 322 | 15.6 | 57.6 |
| | 35 | 4.91 | 113 | 35.8 | 73.1 | 23.0 | 315 | 15.3 | 172.3 |
| | 42 | 4.62 | 106 | 33.8 | 73.2 | 23.0 | 314 | 15.4 | 108.6 |
| 2102 | -2 | 5.21 | 120 | 39.2 | 75.3 | 23.1 | 307 | 12.8 | 45.3 |
| | 7 | 4.51 | 103 | 33.7 | 74.7 | 22.8 | 305 | 12.7 | 6.9 |
| | 14 | 4.50 | 99 | 33.5 | 74.3 | 22.1 | 297 | 13.1 | 142.9 |
| | 21 | 4.26 | 96 | 31.3 | 73.4 | 22.5 | 306 | 14.3 | 64.7 |
| | 28 | 3.63 | 83 | 26.8 | 73.8 | 22.9 | 311 | 14.4 | 14.8 |
| | 35 | 3.76 | 80 | 27.1 | 71.9 | 21.4 | 297 | 14.8 | 224.9 |
| | 42 | 4.25 | 90 | 31.0 | 73.0 | 21.2 | 290 | 14.9 | 137.8 |

| FD114-ADC 3/6 mg/kg | | PLT | WBC | NEUT | LYMP | MONO | EOS | BASO |
|---|---|---|---|---|---|---|---|---|
| | Day(s) Relative to Start Date | (10^9/L) | (10^9/L) | (10^9/L) | (10^9/L) | (10^9/L) | (10^9/L) | (10^9/L) |
| 2101 | -2 | 393 | 9.45 | 2.90 | 5.78 | 0.30 | 0.38 | 0.04 |
| | 7 | 424 | 3.94 | 0.32 | 3.54 | 0.03 | 0.03 | 0.01 |
| | 14 | 671 | 29.77 | 16.74 | 11.09 | 0.95 | 0.02 | 0.54 |
| | 21 | 396 | 10.60 | 6.45 | 3.85 | 0.23 | 0.00 | 0.02 |
| | 28 | 445 | 4.76 | 1.06 | 2.91 | 0.58 | 0.08 | 0.02 |
| | 35 | 689 | 8.95 | 3.60 | 4.53 | 0.73 | 0.03 | 0.03 |
| | 42 | 457 | 11.75 | 7.25 | 4.22 | 0.16 | 0.04 | 0.03 |
| 2102 | -2 | 540 | 15.09 | 4.96 | 8.49 | 0.74 | 0.77 | 0.05 |
| | 7 | 567 | 7.84 | 0.27 | 7.27 | 0.11 | 0.11 | 0.04 |
| | 14 | 985 | 18.37 | 3.72 | 13.49 | 0.75 | 0.01 | 0.21 |
| | 21 | 452 | 18.39 | 9.45 | 8.45 | 0.35 | 0.01 | 0.07 |
| | 28 | 746 | 8.73 | 1.41 | 6.53 | 0.41 | 0.25 | 0.05 |
| | 35 | 841 | 6.54 | 0.44 | 5.53 | 0.48 | 0.01 | 0.03 |
| | 42 | 443 | 13.22 | 5.36 | 7.44 | 0.29 | 0.02 | 0.05 |

Figure 70

| FD114-ADC 3/6 mg/kg | | PT | APTT | FIB |
|---|---|---|---|---|
| | Day(s) Relative to Start Date | (Seconds) | (Seconds) | (g/L) |
| 2101 | -2 | 8.9 | 17.7 | 1.80 |
| | 7 | 8.9 | 16.1 | 1.84 |
| | 14 | 9.2 | 18.0 | 4.21 |
| | 21 | 8.7 | 15.9 | 1.93 |
| | 28 | 9.3 | 16.4 | 3.14 |
| | 35 | 9.2 | 16.6 | 3.51 |
| | 42 | 9.1 | 17.7 | 2.95 |
| 2102 | -2 | 8.5 | 20.8 | 1.95 |
| | 7 | 8.8 | 18.1 | 2.05 |
| | 14 | 8.4 | 19.6 | 3.51 |
| | 21 | 8.8 | 18.9 | 2.19 |
| | 28 | 8.7 | 19.4 | 2.41 |
| | 35 | 8.9 | 17.9 | 1.95 |
| | 42 | 8.9 | 19.0 | 1.72 |

Figure 71

| FD114-ADC 3/6 mg/kg | Day(s) Relative to Start Date | ALT (U/L) | AST (U/L) | ALP (U/L) | GGT (U/L) | CK (U/L) | TBIL (μmol/L) | GLU (mmol/L) | UREA (mmol/L) | CREA (μmol/L) |
|---|---|---|---|---|---|---|---|---|---|---|
| 2101 | -2 | 39.6 | 30.3 | 355 | 33 | 236 | 1.4 | 3.60 | 5.1 | 60 |
|  | 7 | 53.5 | 35.0 | 327 | 30 | 235 | 1.2 | 5.55 | 4.9 | 64 |
|  | 14 | 41.4 | 37.8 | 394 | 33 | 188 | 0.5 | 4.65 | 4.2 | 56 |
|  | 21 | 34.4 | 32.7 | 383 | 35 | 177 | 1.1 | 4.40 | 2.8 | 61 |
|  | 28 | 34.9 | 61.7 | 333 | 29 | 1159 | 1.0 | 3.83 | 5.2 | 59 |
|  | 35 | 35.7 | 37.2 | 519 | 29 | 237 | 1.3 | 4.89 | 4.4 | 58 |
|  | 42 | 34.4 | 35.8 | 420 | 30 | 249 | 0.6 | 4.14 | 5.0 | 61 |
| 2102 | -2 | 27.7 | 20.0 | 410 | 41 | 150 | 1.1 | 5.10 | 6.9 | 68 |
|  | 7 | 70.3 | 29.3 | 419 | 38 | 353 | 1.1 | 5.62 | 6.8 | 67 |
|  | 14 | 34.2 | 36.3 | 545 | 23 | 198 | 0.6 | 7.42 | 6.3 | 73 |
|  | 21 | 32.1 | 29.6 | 448 | 43 | 298 | 1.1 | 6.45 | 5.1 | 87 |
|  | 28 | 46.8 | 39.9 | 347 | 45 | 201 | 1.0 | 6.36 | 6.9 | 70 |
|  | 35 | 30.4 | 28.8 | 531 | 42 | 111 | 1.3 | 6.49 | 4.5 | 69 |
|  | 42 | 34.9 | 31.0 | 449 | 43 | 169 | 0.8 | 4.41 | 6.8 | 77 |

| FD114-ADC 3/6 mg/kg | Day(s) Relative to Start Date | TG (mmol/L) | CHOL (mmol/L) | TP (g/L) | ALB (g/L) | GLOB (g/L) | A/G | Na (mmol/L) | K (mmol/L) | Cl (mmol/L) |
|---|---|---|---|---|---|---|---|---|---|---|
| 2101 | -2 | 0.18 | 4.27 | 70.1 | 42.4 | 27.7 | 1.5 | 144 | 3.97 | 107.5 |
|  | 7 | 0.14 | 4.03 | 66.1 | 40.2 | 25.9 | 1.6 | 146 | 3.52 | 108.6 |
|  | 14 | 0.30 | 4.12 | 71.4 | 33.7 | 37.7 | 0.9 | 146 | 3.90 | 107.7 |
|  | 21 | 0.40 | 3.92 | 69.9 | 36.0 | 33.9 | 1.1 | 143 | 3.90 | 103.6 |
|  | 28 | 0.12 | 4.05 | 71.9 | 35.8 | 36.1 | 1.0 | 146 | 3.91 | 106.8 |
|  | 35 | 0.50 | 3.87 | 79.8 | 40.2 | 39.6 | 1.0 | 147 | 4.09 | 107.5 |
|  | 42 | 0.38 | 3.78 | 79.3 | 37.7 | 41.6 | 0.9 | 142 | 3.98 | 103.4 |
| 2102 | -2 | 0.25 | 1.98 | 69.4 | 37.5 | 31.9 | 1.2 | 148 | 3.96 | 108.2 |
|  | 7 | 0.21 | 1.89 | 68.4 | 36.6 | 31.8 | 1.2 | 150 | 3.96 | 105.9 |
|  | 14 | 0.29 | 2.46 | 73.5 | 34.8 | 38.7 | 0.9 | 150 | 4.11 | 104.3 |
|  | 21 | 0.29 | 2.23 | 73.8 | 35.1 | 38.7 | 0.9 | 152 | 4.69 | 105.1 |
|  | 28 | 0.40 | 2.47 | 75.3 | 34.6 | 40.7 | 0.9 | 146 | 4.19 | 107.4 |
|  | 35 | 0.38 | 2.07 | 77.6 | 38.5 | 39.1 | 1.0 | 147 | 3.98 | 107.0 |
|  | 42 | 0.24 | 1.94 | 77.0 | 42.5 | 34.5 | 1.2 | 148 | 3.85 | 106.5 |

Figure 72

TARGETED CD73 ANTIBODY AND ANTIBODY-DRUG CONJUGATE, AND PREPARATION METHOD THEREFOR AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 370094.401USPC_SEQUENCE_LISTING.txt. The text file is 40.2 KB, was created on Sep. 8, 2020, and is being submitted electronically via EFS-Web.

TECHNICAL FIELD

The present invention relates to the field of medicine, and in particular to CD73-targeting antibody and antibody-drug conjugate, preparation method and use thereof.

BACKGROUND

CD73 is an extracellular 5-nuclease (NT5E) with a molecular weight of 70 KD, which is anchored on the cell surface by glycophosphatidylinositol (GPI). Under physiological conditions, CD73 is mainly expressed in a variety of tissues, such as the large intestine, kidney, liver, lung, lymph node and so on. Extracellular ATP/ADP is hydrolyzed by CD39 to produce adenosine monophosphate (AMP) or nicotinamide adenine dinucleotide (NAD+). The AMP produced by a series of metabolism is catalyzed by CD73 to remove phosphate groups, thereby producing a large amount of adenosines (ADOs) which are exposed around the tissues, and participate in various physiological processes of cells by binding to the corresponding adenosine receptors (A1AR, A2AR, A2BR, and A3AR).

Studies have shown that CD73 and adenosine pathways are closely related to the occurrence and development of tumors. First, they can promote tumor immune escape. Hypoxia, activation of inflammatory factors (IFN-γ, TNF-α, IL-1β, TGF-β, etc.) and related signaling pathways (Wnt, cAMP) can induce abnormal expression of CD73 in tumor cells. Through catalyzing AMP, CD73 can produce a large amount of ADOs which surround the tumor, thereby forming a suppressive "loop" microenvironment against tumor immunity and promoting tumor immune escape. The main mechanisms are as follows. 1) ADO acts on the adenosine receptor (A2AR) on the surface of CD8+ T cell, inhibits its proliferation and expansion through cAMP signaling pathway, and reduces the release of related pro-inflammatory cytokines IFN-γ, TNF-α, etc., thereby reducing its cytotoxic effect. 2) ADO can interfere with the adhesion between NK cells and tumor cells, thereby reducing the ability of exocytosis cytotoxic particles from NK cells so that the cytotoxic effect is weakened. 3) Through binding A2AR on the surface of regulatory T cells (Tregs), ADO promotes the expansion of Treg cells and enhances immunosuppressive and anti-inflammatory functions thereof. Meanwhile, ADO produced via catalysis of CD73 on the surface of Tregs combines with A2AR on CD8$^+$ effector T cells to inhibit NF-κB activation, thereby decreasing secretion of pro-inflammatory cytokines and chemokines. Preclinical studies have also shown that the injection of CD4+CD25+Tregs derived from wild-type mice into Treg-deficient mice will promote the development of colon cancer, while the injection of Tregs derived from CD73-deficient mice have no effect, suggesting that CD73 and Tregs play an important role in tumor immunosuppression. 4) ADO inhibits the differentiation of M1 macrophages and reduces the release of pro-inflammatory cytokines IL-12, TNF-α, iNOS, etc., which can activate M2 macrophages, and produces a large amount of anti-inflammatory cytokines (TGF-β, arginase1) to help tumor escape from the immune system. Secondly, CD73 can promote the process of tumor growth and metastasis. Preclinical research results show that CD73 is abnormally expressed in various tumor cells, such as breast cancer, bladder cancer, ovarian cancer, colon cancer, non-small cell lung cancer, etc., and clinical data show that high expression of CD73 is closely related to the poor prognosis of tumor patients [Expert Rev Anticancer Ther. 2017; 17: 527], suggesting that CD73 can be used as a clinical treatment and prognostic target for various tumors. In vitro studies indicate that CD73 can promote the formation of new blood vessels in C57BL/6 mice bearing B16F10 melanoma cells, and the use of CD73 blocking medicine can significantly inhibit the number of new blood vessels and the maturation of the vascular bed. In addition, through up-regulating cyclin D1, ADO produced by CD73 can promote the proliferation of microvascular endothelial cells and the release of vascular endothelial growth factor (VEGF), promote tumor angiogenesis, and provide sufficient energy for tumor growth. In vivo studies have shown that CD73-deficient mice exhibit reduced tumor blood vessels, suggesting that it is possible to combine a CD73-targeting treatment with anti-angiogenesis drugs (Bevacizumab) to provide a new therapy for clinical treatment of tumors. Many studies have shown that ADO is closely related to the metastasis of tumor cells. By analyzing tumor samples of bladder cancer, it was found that CD73 expression in lymph node metastasis samples was significantly higher than that in non-lymph node metastasis tumor samples. Stagg et al. treated mice with CD73 mAb [TY/23] which effectively inhibited 4T1.2 spontaneous lung metastasis. Another result also confirms that CD73 mAb AD2 promotes CD73 aggregation and endocytosis, thereby preventing circulating tumor cells from establishing secondary tumor sites, so that the ability of tumor cells to exude and colonize other tissues is greatly limited. Similarly, the analysis of clinical data shows that the high expression of CD73 is closely related to the metastases of gastric cancer, bladder cancer, malignant melanoma etc., further suggesting that CD73 plays an important role in tumor metastasis.

Drug resistance is a major problem and a challenge in tumor treatment. Studies have shown that CD73 is involved in the development of drug resistance in tumor chemotherapy, ultrasound therapy, targeted therapy and immunotherapy, which greatly hinders the effectiveness of tumor treatment [Discovery Today 2017; 22:1686]. Studies have shown that when doxorubicin (Anthracycline) is used for treating triple-negative breast cancer (TNBC) patients, high expression of CD73 is closely related to pathological complete response rate (pCR), that is, patients with low expression of CD73 show better response to doxorubicin therapy. The mechanism studies have shown that doxorubicin inhibits the secretion of IFN-γ in CD8+ T cells by up-regulating expression of CD73/CD39, thereby inhibiting anti-tumor immunity. The use of monoclonal antibodies targeting CD73 can significantly enhance the anti-tumor immune response and anti-tumor activity of doxorubicin. In addition, in a clinical trial of Trastuzumab in the treatment of Her2$^+$ breast cancer, high expression of CD73 was significantly associated with poor prognosis; a combination of CD73-targeting monoclonal antibody and Trastuzumab can increase CD8+ T cells and reduce MDSC infiltration, thereby producing synergistic anti-tumor effects [Cancer Res. 2017; 77: 5652].

By utilizing the characteristic that a monoclonal antibody specifically recognizes a specific antigen on the surface of tumor cells, an antibody-drug conjugate (ADC) can accurately deliver an anti-tumor drug (such as a small-molecule chemotherapeutic drug) to tumor target cells and release the drug there, so as to achieve the purpose of accurately killing tumors. ADC is also regarded as the most potential anti-tumor drug because of its appropriate molecular weight, high stability, strong targeting property, and low toxic side effect. However, with respect to successful development of ADCs, there are also many problems that have to be taken into account and have to be solved, for example, an antibody has to specifically recognize a lesion site, has a low immunosensitization, and can be efficiently and rapidly internalized by a cell; an antibody-drug linker has to be highly stable in blood and can be specifically activated and efficiently release the small-molecule drug in the targeted cell; the conjugated small-molecule drug has a strong ability of killing cells, and so on.

In summary, CD73 is abnormally expressed in a variety of tumor cells and is closely related to the poor prognosis of tumor patients. CD73 mainly produces suppressive effects on tumor immunity through the adenosine pathway to promote tumor growth, metastasis and angiogenesis. In addition, CD73 is also involved in the generation of resistance against anti-tumor drug, which brings great challenges to tumor treatment. Therefore, the development of CD73-targeting monoclonal antibody drug provides new solutions of single or combined therapy for the clinical treatment of patients with CD73 abnormal expression tumors. At the same time, there is a lack of highly specific antibody-drug conjugates against human CD73 in clinical practice at present. Therefore, the development of antibody-drug conjugates that target tumor CD73 and have better drug performance will exhibit inherent characteristics and advantages, and provide new ideas and prospects for the treatment of cancers with abnormal expression of CD73.

SUMMARY OF THE INVENTION

The present invention provides an antibody targeting human CD73, which has the activity of blocking CD73 from catalyzing the hydrolysis of adenosine monophosphate (AMP) into adenosine, has the activity of inhibiting tumor growth and metastasis, and can reduce the emergence of resistance to anti-tumor therapy.

In the first aspect of the present invention, it provides a heavy chain variable region of an antibody, wherein the heavy chain variable region comprises the following three complementarity determining regions or CDRs:
CDR1 as shown in SEQ ID NO. 10,
CDR2 as shown in SEQ ID NO. 11, and
CDR3 as shown in SEQ ID NO. 12;
or,
CDR1 as shown in SEQ ID NO. 1,
CDR2 as shown in SEQ ID NO. 2, and
CDR3 as shown in SEQ ID NO. 3;
or,
CDR1 as shown in SEQ ID NO. 21,
CDR2 as shown in SEQ ID NO. 22, and
CDR3 as shown in SEQ ID NO. 23;
wherein any one of the above amino acid sequences further comprises a derivative sequence which is obtained through optional addition, deletion, modification and/or substitution of at least one amino acid and is capable of retaining CD73 binding affinity.

In another preferred embodiment, the heavy chain variable region comprises the following complementarity determining regions:
heavy chain complementarity determining regions HCDR1, HCDR2, and HCDR3 of mAb002c as shown in SEQ ID NO. 10, SEQ ID NO. 11, and SEQ ID NO. 12; or
heavy chain complementarity determining regions HCDR1, HCDR2, and HCDR3 of mAb001c as shown in SEQ ID NO. 1, SEQ ID NO. 2, and SEQ ID NO. 3; or
heavy chain complementarity determining regions HCDR1, HCDR2, and HCDR3 of mAb004c as shown in SEQ ID NO. 21, SEQ ID NO. 22, and SEQ ID NO. 23.

In another preferred embodiment, the heavy chain variable region further comprises human FR regions or mouse FR regions.

In another preferred embodiment, the heavy chain variable region has the amino acid sequence as shown in SEQ ID NO. 7.

In another preferred embodiment, the heavy chain variable region has the amino acid sequence as shown in SEQ ID NO. 16, SEQ ID NO. 17, or SEQ ID NO. 18.

In another preferred embodiment, the heavy chain variable region has the amino acid sequence as shown in SEQ ID NO. 27, SEQ ID NO. 28, or SEQ ID NO. 29.

In another preferred embodiment, the heavy chain variable region has the amino acid sequence as shown in SEQ ID NO. 31, SEQ ID NO. 32, SEQ ID NO. 33, SEQ ID NO. 34, SEQ ID NO. 35, SEQ ID NO. 45, or SEQ ID NO. 46.

In another preferred embodiment, the heavy chain variable region has the amino acid sequence as shown in SEQ ID NO. 38, SEQ ID NO. 39, SEQ ID NO. 40, or SEQ ID NO. 41.

In the second aspect of the present invention, it provides a heavy chain of an antibody, which has the heavy chain variable region of the first aspect of the present invention.

In another preferred embodiment, the heavy chain of the antibody further comprises a heavy chain constant region.

In another preferred embodiment, the heavy chain constant region is of human, mouse or rabbit.

In the third aspect of the present invention, it provides a light chain variable region of an antibody, wherein the light chain variable region comprises the following three complementarity determining regions or CDRs:
CDR1' as shown in SEQ ID NO. 13,
CDR2' as shown in SEQ ID NO. 14, and
CDR3' as shown in SEQ ID NO. 15;
or,
CDR1' as shown in SEQ ID NO. 4,
CDR2' as shown in SEQ ID NO. 5, and
CDR3' as shown in SEQ ID NO. 6;
or,
CDR1' as shown in SEQ ID NO. 24,
CDR2' as shown in SEQ ID NO. 25, and
CDR3' as shown in SEQ ID NO. 26;
wherein any one of the above amino acid sequences further comprises a derivative sequence which is obtained through optional addition, deletion, modification and/or substitution of at least one amino acid and is capable of retaining CD73 binding affinity.

In another preferred embodiment, the light chain variable region comprises the following complementarity determining regions:
light chain complementarity determining regions LCDR1, LCDR2, and LCDR3 of mAb002c as shown in SEQ ID NO. 13, SEQ ID NO. 14, and SEQ ID NO. 15; or light chain complementarity determining regions LCDR1, LCDR2, and LCDR3 of mAb001c as shown in SEQ ID NO. 4, SEQ ID NO. 5, and SEQ ID NO. 6; or light chain complementarity determining regions LCDR1, LCDR2, and LCDR3 of mAb004c as shown in SEQ ID NO. 24, SEQ ID NO. 25, and SEQ ID NO. 26.

In another preferred embodiment, the light chain variable region further comprises human FR regions or mouse FR regions.

In another preferred embodiment, the light chain variable region has the amino acid sequence as shown in SEQ ID NO. 8, or SEQ ID NO. 9.

In another preferred embodiment, the light chain variable region has the amino acid sequence as shown in SEQ ID NO. 19, or SEQ ID NO. 20.

In another preferred embodiment, the light chain variable region has the amino acid sequence as shown in SEQ ID NO. 30.

In another preferred embodiment, the light chain variable region has the amino acid sequence as shown in SEQ ID NO. 36, SEQ ID NO. 37, or SEQ ID NO. 47.

In another preferred embodiment, the light chain variable region has the amino acid sequence as shown in SEQ ID NO. 42, SEQ ID NO. 43, or SEQ ID NO. 44.

In a fourth aspect of the present invention, it provides a light chain of an antibody, wherein the light chain has the light chain variable region of the third aspect of the present invention.

In another preferred embodiment, the light chain of the antibody further comprises a light chain constant region.

In another preferred embodiment, the light chain constant region is of human, mouse or rabbit.

In the fifth aspect of the present invention, it provides an antibody having:

(1) the heavy chain variable region of the first aspect of the present invention; and/or (2) the light chain variable region of the third aspect of the present invention;

alternatively, the antibody has: the heavy chain of the second aspect of the present invention; and/or the light chain of the fourth aspect of the present invention.

In another preferred embodiment, the antibody is selected from the group consisting of an animal-derived antibody, a chimeric antibody, a humanized antibody, and a combination thereof.

In another preferred embodiment, the CDR region of the humanized antibody comprises 1, 2, or 3 amino acid changes.

In another preferred embodiment, the animal is a non-human mammal, preferably a mouse, sheep, or rabbit.

In another preferred embodiment, the antibody is a double chain antibody or a single chain antibody.

In another preferred embodiment, the antibody is a monoclonal antibody.

In another preferred embodiment, the antibody is a partially or fully humanized monoclonal antibody. In another preferred embodiment, the number of added, deleted, modified and/or substituted amino acids does not exceed 40%, preferably 20%, more preferably 10% of the total number of amino acids in the initial amino acid sequence.

In another preferred embodiment, the number of added, deleted, modified and/or substituted amino acids is 1-7, preferably 1-3, and more preferably one.

In another preferred embodiment, the sequence obtained through addition, deletion, modification and/or substitution of at least one amino acid is an amino acid sequence with at least 80% homology.

In another preferred embodiment, the derivative sequence obtained through addition, deletion, modification and/or substitution of at least one amino acid can inhibit the protease catalytic function of cell surface CD73 or recombinant CD73.

In another preferred embodiment, the antibody is in the form of a drug conjugate.

In another preferred embodiment, the affinity $EC_{50}$ of the derivative sequence to CD73 (such as the extracellular domain of human CD73 protein, or CD73-ECD) is 0.016 to 0.2 nM, preferably 0.016 to 0.03 nM, more preferably is 0.016 to 0.02 nM.

In another preferred embodiment, the antibody has one or more properties selected from the group consisting of:

(a) inhibiting an activity of CD73 to catalyze hydrolysis of adenosine monophosphate (AMP) into adenosine;

(b) specifically binding to tumor cells, and/or CD73 of the immune/stromal cells in the tumor microenvironment;

(c) inhibiting an activity of CD73 to catalyze AMP hydrolysis in tumor/tumor microenvironment;

(d) inhibiting tumor cell migration or metastasis;

(e) inhibiting tumor growth and improving the anti-tumor efficacy of combination drug therapy;

(f) promoting the proliferation, survival and function of immune cells, thereby improving the effect of tumor immunity.

In the sixth aspect of the invention, it provides a recombinant protein which comprises:

(i) the heavy chain variable region of the first aspect of the present invention, the heavy chain of the second aspect of the present invention, the light chain variable region of the third aspect of the present invention, the light chain of the fourth aspect of the present invention, or the antibody of the fifth aspect of the present invention; and (ii) an optional tag sequence that assists expression and/or purification.

In another preferred embodiment, the tag sequence comprises a 6His tag.

In another preferred embodiment, the recombinant protein (or polypeptide) comprises fusion protein.

In another preferred embodiment, the recombinant protein is a monomer, a dimer, or a multimer.

In the seventh aspect of the present invention, it provides a CAR construct, wherein the scFv segment of the monoclonal antibody antigen binding region of the CAR construct is a binding region that specifically binds to CD73, and the scFv has the heavy chain variable region of the first aspect of the present invention and the light chain variable region of the third aspect of the present invention.

In the eighth aspect of the present invention, it provides a recombinant immune cell expressing exogenous CAR construct of the seventh aspect of the present invention.

In another preferred embodiment, the immune cell is selected from the group consisting of: a NK cell and a T cell.

In another preferred embodiment, the immune cell is derived from human or non-human mammals (such as mice).

In the ninth aspect of the present invention, it provides an antibody-drug conjugate comprising:

(A) an antibody moiety selected from the group consisting of: the heavy chain variable region of the first aspect of the present invention, the heavy chain of the second aspect of the present invention, the light chain variable region of the third aspect of the present invention, the light chain of the fourth aspect of the present invention, the antibody of the fifth aspect of the present invention, and a combination thereof; and (b) a coupling moiety coupled to the antibody moiety, and the coupling moiety is selected from the group consisting of a detectable label, a drug, a toxin, a cytokine, a radionuclide, an enzyme, and a combination thereof.

In another preferred embodiment, the antibody moiety is coupled to the coupling moiety via a chemical bond or linker.

In another preferred embodiment, the antibody-drug conjugate or ADC is as shown in the following molecular formula:

wherein,
Ab is an anti-CD73 antibody,
LU is a linker (also called as connector);
D is a drug;
and the subscript p is a value selected from 1-10, and preferably 1-8.

In another preferred embodiment, the LU is selected from the group consisting of:
6-maleimidocaproyl-valine-citrulline-p-aminobenzyloxycarbonyl (MC-val-cit-PAB), 6-maleimidocaproyl-alanine-phenylalanine-p-aminobenzyloxycarbonyl (MC-ala-phe-PAB), maleimidopropionyl-valine-citrulline-p-aminobenzyloxycarbonyl (MP-val-cit-PAB), maleimidopropionyl-alanine-phenylalanine-p-aminobenzyloxycarbonyl (MP-ala-phe-PAB), N-succinimidyl 4-(2-pyridylthio)pentanoate (SPP), N-succinimidyl 4-(N-maleimidomethyl)cyclohexane-1-carboxylate (SMCC), 4-(2-pyridyldithio)butanoic acid N-hydrosuccinimide ester (SPDB), N-succinimidyl (4-iodo-acetyl)aminobenzoate (SIAB) and disubstituted maleimide linker.

In another preferred embodiment, the LU is a disubstituted maleimide linker.

In another preferred embodiment, the structure of the antibody-drug conjugate is shown in formula Ia and Ib:

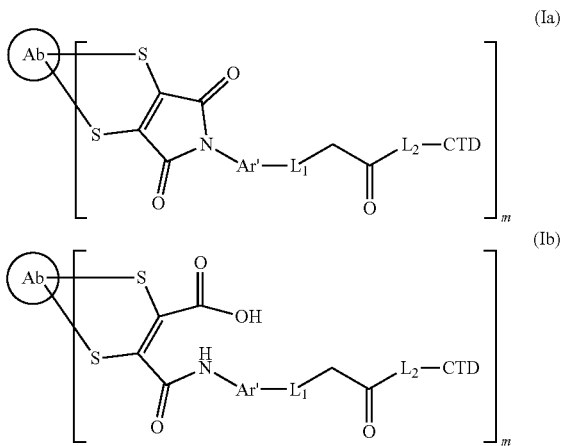

wherein,
Ar' is selected from the group consisting of: substituted or unsubstituted C6-C10 aryl, substituted or unsubstituted 5-12 membered heteroaryl, substituted or unsubstituted C6-C10 arylene, substituted or unsubstituted 5-12 membered heteroarylene;

$L_1$ is —O(CH$_2$CH$_2$O)$_n$— linked to the Ar' group, wherein n is selected from any integer from 1-20.

$L_2$ is a chemical bond, or AA-PAB structure; wherein AA is a polypeptide fragment consisted of 2-4 amino acids, and PAB is p-aminobenzylcarbamoyl;

CTD is a cytotoxic small molecule drug bonded to $L_2$ through an amide bond.

m is 1.0-5.0, preferably 3.0-4.2; more preferably 3.5-4.5; still more preferably 3.8-4.2, still more preferably 3.9-4.1, most preferably 4.0;

Ab is an antibody targeting CD73.

In another preferred embodiment, the formula Ib is a ring-opening product of the N-phenylmaleimide of formula Ia.

In another preferred embodiment, the conjugate is covalently linked with one or more drug components.

In another preferred embodiment, the antibody moiety and the coupling moiety are coupled by covalent means (for example, by covalently linking to the linker, respectively).

In another preferred embodiment, the ring-closing or ring-opening maleimide group is linked to a reduced sulfhydryl group of a disulfide chain in the hinge region of the antibody.

In another preferred embodiment, the antibody-drug conjugate Ia and/or Ib is obtained by the reduction of the disulfide linkage into a pair of cysteine residues in the hinge region of the antibody or the antibody fragment and by the substitution reaction of the sulfhydryl group in the cysteine residue with the aryl thioether in the substituted maleimide linker-drug conjugate as shown in formula Ic.

In another preferred embodiment, the ring-closing or ring-opening maleimide group is linked to the fully reduced antibody, that is, the 2 disulfide linkages in the hinge region are completely opened, and preferably m is 3.8-4.2, more preferably 3.9-4.1, and most preferably 4.0.

In another preferred embodiment, the Ar' is selected from the group consisting of phenyl, halogen-substituted phenyl, C1-C4 alkylphenyl, C1-C4 alkoxyphenyl, 2-pyridyl, 2-pyrimidinyl, 1-methylimidazol-2-yl,

wherein W is an amino $R^1$ linked to carbonyl, $R^1$ is selected from —NH$_2$,

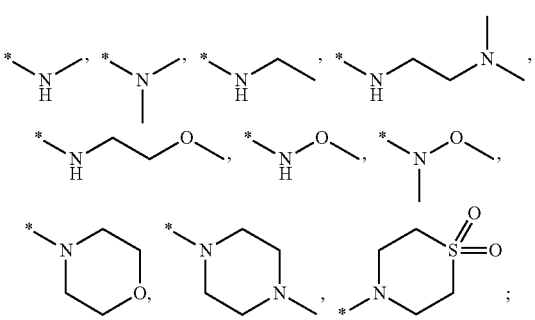

wherein, C1-C4 alkylphenyl is more preferably 4-methylphenyl; the C1-C4 alkoxyphenyl is more preferably 4-methoxyphenyl.

In another preferred embodiment, Ar' is selected from substituted or unsubstituted phenylene or pyridyl, and the substitution means that the hydrogen atom on the group is substituted by one or more substituents selected from the group consisting of: halogen, C1-C4 alkyl, C1-C4 alkoxy, trifluoromethyl, nitrile group (—CN), and amide group.

In another preferred embodiment, the AA is selected from the group consisting of: Val-Cit (valine-citrulline), Val-Ala (valine-alanine), Phe-Lys (phenylalanine-lysine), Ala-Ala-Asn (alanine-alanine-asparagine), D-Ala-Phe-Lys (D-alanine-phenylalanine-lysine), Gly-Gly-Phe-Gly (glycine-glycine-phenylalanine-glycine), and a combination thereof.

In another preferred embodiment, the drug D or CTD is selected from the group consisting of:
(i) a maytansine derivative (DM1, DM4), auristatin and dorastatin;
(ii) Monomethyl auristatin E (MMAE), Monomethyl auristatin F (MMAF), Monomethyl Dolastatin 10 (MMAD) derivatives and a combination thereof; and
(iii) a DNA damage drug, preferably, the DNA damage drug comprises docamycin, pyrrolo[2,1-c][1,4]benzodiazepine (PBD).

In another preferred embodiment, the antibody is selected from the group consisting of an animal-derived antibody, a chimeric antibody, a humanized antibody, and a combination thereof.

In another preferred embodiment, the heavy chain variable region sequence of the antibody is selected from the group consisting of: SEQ ID NO. 7, SEQ ID NO. 16, SEQ ID NO. 17, SEQ ID NO. 18, SEQ ID NO. 27, SEQ ID NO. 28, SEQ ID NO. 29, SEQ ID NO. 31, SEQ ID NO. 32, SEQ ID NO. 33, SEQ ID NO. 34, SEQ ID NO. 35, SEQ ID NO. 45, SEQ ID NO. 46, SEQ ID NO. 38, SEQ ID NO. 39, SEQ ID NO. 40, and SEQ ID NO. 41; and/or
the light chain variable region sequence of the antibody is selected from the group consisting of: SEQ ID NO. 8, SEQ ID NO. 9, SEQ ID NO. 19, SEQ ID NO. 20, SEQ ID NO. 30, SEQ ID NO. 36, SEQ ID NO. 37, SEQ ID NO. 47, SEQ ID NO. 42, SEQ ID NO. 43, and SEQ ID NO. 44.

In another preferred embodiment, the chimeric antibody is selected from the group consisting of: mAb001c, mAb001c-VK-SGS, mAb002c, mAb002c-VH-QG, mAb002c-VH-NA, mAb002c-VK-SG, mAb002c-VH-QG/VK-SG, mAb004c, mAb004c-VH-QG, and mAb004c-VH-NA (Table-1 in the specification); the humanized antibody is selected from the group consisting of: Hu001c-14, Hu001c-15, Hu001c-21, Hu001c-22, Hu001c-23, Hu001c-24, Hu001c-25, Hu001c-28, Hu001c-30, Hu001c-31, Hu001c-32, Hu002c-2, Hu002c-3, Hu002c-4, Hu002c-6, Hu002c-7, Hu002c-8, Hu002c-10, Hu002c-11, Hu002c-12, Hu002c-14, Hu002c-15, and Hu002c-16 (Table-2 in the specification).

In the tenth aspect of the present invention, it provides use of an active ingredient selected from the group consisting of: the heavy chain variable region of the first aspect of the present invention, the heavy chain of the second aspect of the present invention, the light chain variable region of the third aspect of the present invention, the light chain of the fourth aspect of the present invention, the antibody of the fifth aspect of the present invention, the recombinant protein of the sixth aspect of the present invention, the immune cell of the eighth aspect, the antibody-drug conjugate of the ninth aspect of the present invention, and a combination thereof, wherein the active ingredient is used for (a) preparing a detection reagent, a detection plate or a kit; and/or (b) preparing a drug for the prevention and/or treatment of a CD73-related disease.

In another aspect of the present invention, it provides use of the antibody-drug conjugate of the ninth aspect of the present invention, wherein the antibody-drug conjugate is used for (i) preparing a diagnostic reagent; and/or (ii) preparing a drug for the prevention and/or treatment of a CD73-related disease.

In another preferred embodiment, the detection reagent, detection plate or kit is used for:
(1) detecting CD73 protein in the sample; and/or
(2) detecting endogenous CD73 protein in tumor cells; and/or
(3) detecting tumor cells expressing CD73 protein.

In another preferred embodiment, the detection reagent, detection plate or kit is used for diagnosing a CD73-related disease.

In another preferred embodiment, the drug is used for treating or preventing a CD73 high expression tumor, tumor migration, or tumor resistance.

In another preferred embodiment, the tumor resistance comprises: resistance of tumor immunotherapy drug, resistance of tumor targeted therapy drug, resistance of conventional tumor chemotherapy, and insensitivity to radiotherapy.

In another preferred embodiment, the drug is used for a use selected from the group consisting of:
(a) inhibiting an activity of CD73 to catalyze the hydrolysis of adenosine monophosphate (AMP) into adenosine;
(b) specifically binding to tumor cells, and/or CD73 of the immune/stromal cells in the tumor microenvironment;
(c) inhibiting an activity of CD73 to catalyze AMP hydrolysis in tumor/tumor microenvironment;
(d) inhibiting tumor cell migration or metastasis;
(e) inhibiting tumor growth and improving the anti-tumor efficacy of combination drug therapy;
(f) promoting the proliferation, survival and function of immune cells, thereby improving the effect of tumor immunity.

In another preferred embodiment, the CD73-related disease is selected from the group consisting of cancer, an autoimmune disease, a metabolism-related disease, an infectious disease, and a combination thereof.

In another preferred embodiment, the CD73-related disease comprises: tumorigenesis, tumor growth and/or metastasis.

In another preferred embodiment, the cancer comprises a solid tumor and a hematologic cancer.

In another preferred embodiment, the cancer is a tumor with high CD73 expression.

In another preferred embodiment, the tumor with high CD73 expression is selected from the group consisting of breast cancer, lung cancer, pancreatic cancer, ovarian cancer, prostate cancer, rectal cancer, glioma, melanoma, leukemia, lymphoma, and a combination thereof.

In another preferred embodiment, the cancer is a drug-resistant tumor.

In another preferred embodiment, the tumor with high CD73 expression refers to the ratio of the level L1 of CD73 transcript and/or protein in tumor tissue to the level L0 of CD73 transcript and/or protein in normal tissue, L1/L0 is ≥2, preferably ≥3.

In another preferred embodiment, the metabolism-related diseases comprises diabetes, diet-induced obesity, and adipose inflammation.

In another preferred embodiment, the infectious disease comprises bacterial and viral infection.

In the eleventh aspect of the present invention, it provides a pharmaceutical composition comprising:

(i) an active ingredient selected from the group consisting of: the heavy chain variable region of the first aspect of the present invention, the heavy chain of the second aspect of the present invention, the light chain variable region of the third aspect of the present invention, the light chain of the fourth aspect of the present invention, the antibody of the fifth aspect of the present invention, the recombinant protein of the sixth aspect of the present invention, the immune cell of the eighth aspect, the antibody-drug conjugate of the ninth aspect of the present invention, and a combination thereof; and (ii) a pharmaceutically acceptable carrier.

In another aspect of the present invention, it provides a pharmaceutical composition comprising:

(i) an active ingredient, wherein the active ingredient is the antibody-drug conjugate of the ninth aspect of the present invention and a combination thereof; and (ii) a pharmaceutically acceptable carrier.

In another preferred embodiment, the pharmaceutical composition is a liquid formulation.

In another preferred embodiment, the pharmaceutical composition is an injection.

In the twelfth aspect of the present invention, it provides a polynucleotide encoding a polypeptide selected from the group consisting of:

(1) the heavy chain variable region of the first aspect of the present invention, the heavy chain of the second aspect of the present invention, the light chain variable region of the third aspect of the present invention, the light chain of the fourth aspect of the present invention, or the antibody of the fifth aspect of the present invention; or (2) the recombinant protein of the sixth aspect of the present invention;

(3) the CAR construct of the seventh aspect of the present invention.

In the thirteenth aspect of the invention, it provides a vector comprising the polynucleotide of the twelfth aspect of the present invention.

In another preferred embodiment, the vector comprises: a bacterial plasmid, a phage, a yeast plasmid, a plant cell virus, a mammalian cell virus such as an adenovirus, retrovirus, or other vectors.

In the fourteenth aspect of the invention, it provides a genetically engineered host cell comprising the vector of the thirteenth aspect of the present invention or having the polynucleotide of the twelfth present aspect of the invention integrated into its genome.

In the fifteenth aspect of the present invention, it provides an in vitro method (including diagnostic or non-diagnostic method) for detecting CD73 in a sample, wherein the method comprising the steps:

(1) contacting a sample with the antibody of the fifth aspect of the present invention in vitro;

(2) detecting whether an antigen-antibody complex is formed, wherein the formation of a complex indicates the presence of CD73 in the sample.

In the sixteenth aspect of the present invention, it provides a detection plate comprising a substrate (or support plate) and a test strip, wherein the test strip comprising the antibody of the fifth aspect of the present invention or the immunoconjugate of the ninth aspect of the present invention.

In the seventeenth aspect of the present invention, it provides a kit comprising:

(1) a first container containing the antibody of the fifth aspect of the present invention; and/or (2) a second container containing a secondary antibody against the antibody of the fifth aspect of the present invention;

alternatively, the kit comprises the detection plate of the sixteenth aspect of the present invention.

In the eighteenth aspect of the present invention, it provides a method for preparing a recombinant polypeptide, which comprises the steps of:

(i) culturing the host cell of the fourteenth aspect of the present invention under a condition suitable for expression;

(b) isolating a recombinant polypeptide from the culture, wherein the recombinant polypeptide is the antibody of the fifth aspect of the present invention or the recombinant protein of the sixth aspect of the present invention.

In the nineteenth aspect of the present invention, it provides a method for treating CD73-related diseases, wherein the method comprises: administering the antibody of the fifth aspect of the present invention, the antibody-drug conjugate of the antibody of the ninth aspect, or the CAR-T cell expressing the antibody, and a combination thereof, to a subject in need.

In another preferred embodiment, the method further comprises: administering other drugs or treatment methods to the subject in need for a combined therapy.

In another preferred embodiment, the other drugs or treatment methods comprise: an anti-tumor immunotherapy drug, a tumor-targeted drug, a tumor chemotherapeutic agent, and tumor radiotherapy.

In another preferred embodiment, the anti-tumor immunotherapy drug comprises a PD-1 and PD-L1 monoclonal antibody.

In the twentieth aspect of the invention, it provides a method for the preparation of a chimeric antibody, comprising the steps of:

cloning the nucleotide sequence of the heavy chain variable region of the first aspect of the present invention and/or the light chain variable region of the third aspect of the present invention into an expression vector containing the nucleotide sequence of a human antibody constant region, and expressing the human-mouse chimeric antibody by transfecting animal cells.

In the twenty-first aspect of the present invention, it provides a method for the preparation of a humanized antibody, comprising the steps of:

implanting the nucleotide sequences of the CDR regions in the heavy chain variable region of the first aspect of the present invention and/or the light chain variable region of the third aspect of the present invention into a nucleoside sequence template containing human antibody FR regions, then cloning the resultant template into an expression vector containing the constant region of a human antibody, and expressing the humanized antibody by transfecting animal cells.

In the twenty-second aspect of the present invention, it provides a method for inhibiting tumor cell growth and migration, comprising the steps of: administering the antibody of the fifth aspect of the present invention and an antibody-drug conjugate of the antibody, a CAR-T cell expressing the antibody, and a combination thereof to a subject in need.

In the twenty-third aspect of the present invention, it provides a method for inhibiting tumor growth in a model animal, comprising the steps of: administering the antibody of the fifth aspect of the present invention and an antibody-drug conjugate of the antibody, or a CAR-T cell expressing the antibody to a subject in need.

In another preferred embodiment, the drug can be administered alone or in combination with, such as, tumor immunotherapy, a tumor-targeted drug, a cytotoxic drug, and radiotherapy.

In the twenty-fourth aspect of the present invention, it provides a method for preparing the antibody-drug conjugate of the ninth aspect of the present invention, comprising the steps:

(1) reacting an antibody with a reducing reagent in a buffer to obtain a reduced antibody;

(2) cross-linking (coupling) a linker-drug conjugate of formula Ic with the reduced antibody obtained in step (1) in a mixture solution of a buffer solution and an organic solvent to obtain the antibody-drug conjugate 1a and/or 1b.

In another preferred embodiment, the cross-linking reaction of the preparation method is shown in the following scheme:

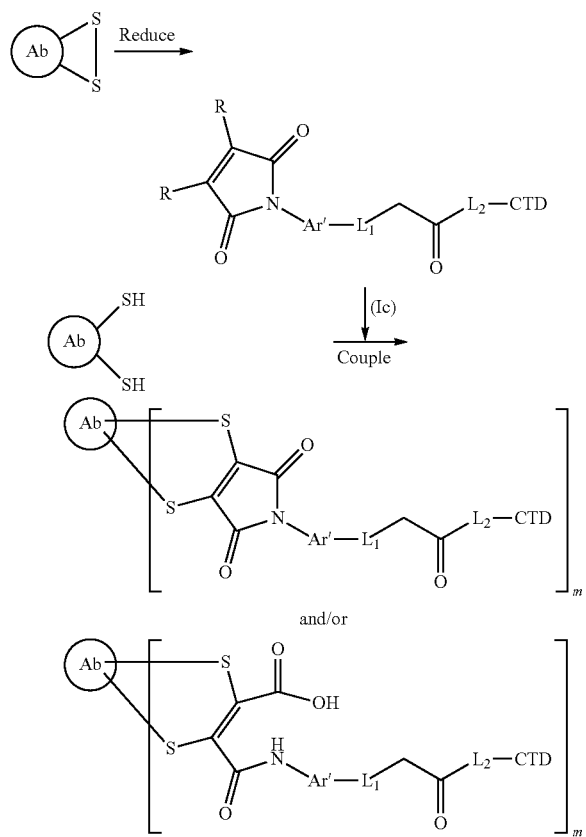

In another preferred embodiment, in step (1), the antibody is reduced by a reducing reagent, so that the inter-chain disulfide bond in the antibody is reduced to produce sulfhydryl groups.

In another preferred embodiment, the reducing agent in step (1) is tris(2-carboxyethyl)phosphine hydrochloride (TCEP), beta-mercaptoethanol, beta-mercaptoethylamine hydrochloride, or dithiothreitol (DTT).

In another preferred embodiment, the buffer is selected from the group consisting of: potassium dihydrogen phosphate-sodium hydroxide ($KH_2PO_4$—NaOH)/sodium chloride (NaCl)/diethylene triamine pentacetate acid (DTPA) buffer, disodium hydrogen phosphate-citric acid/sodium chloride (NaCl)/diethylene triamine pentaacetic acid (DTPA), boric acid-borax/sodium chloride (NaCl)/diethylene triamine pentaacetic acid (DTPA), histidine-sodium hydroxide/sodium chloride (NaCl)/diethylene triamine pentaacetic acid (DTPA), and PBS/diethylene triamine pentaacetic acid (DTPA).

In another preferred embodiment, in step (2), the organic solvent in the reaction solution is no more than 15% by volume.

In another preferred embodiment, the organic solvent in step (2) is selected from the group consisting of: acetonitrile (ACN), dimethylformamide (DMF), dimethylacetamide (DMA), and dimethyl sulfoxide (DMSO).

In another preferred embodiment, in step (2), the coupling reaction is conducted at a temperature of 0-37° C.

In another preferred embodiment, in step (1), the reduction is carried by using beta-mercaptoethanol, beta-mercaptoethylamine hydrochloride or DTT, and a further step is included between step (1) and step (2): passing the product through a desalting column or subjecting the product to ultrafiltration after the reduction reaction is completed to remove excessive reducing reagent.

In another preferred embodiment, the antibody-drug conjugate Ia is converted into the antibody-drug conjugate Ib in a pH 6-8 buffer.

It is to be understood that the various technical features of the present invention mentioned above and the various technical features specifically described hereinafter (as in the Examples) may be combined with each other within the scope of the present invention to constitute a new or preferred technical solution, which needs not be described one by one, due to space limitations.

DESCRIPTION OF DRAWINGS

FIGS. 1A and 1B shows the discovery of the anti-human CD73 antibody of the present invention. FIG. 1A shows the binding activity of a series of original anti-human CD73 monoclonal antibodies (original hybridoma) culture supernatant against human breast cancer cell MDA-MB-231 (CD73-P) with CD73-high expression and MDA-MB-453 (CD73-N) with CD73-low expression detected by Fluorescence Activated Cell Sorter (FACS). The five antibodies shown are numbered mAb001, mAb002, mAb003, mAb004, mAb005. FIG. 1B shows the identification of the subtypes of the 5 antibodies after purification, wherein the binding affinity for MDA-MB-231 cells was determined by FACS and the $EC_{50}$ were 1.24 nM, 0.65 nM, 10.7 nM, 4.69 nM, and 26.07 nM, respectively.

FIG. 2 shows the results of agarose gel electrophoresis of PCR amplified heavy chain variable region (VH) and light chain variable region (VL) fragments of mAb001, mAb002, and mAb004. After sequencing and identification, VH/VL fragments were used to clone and assemble human-mouse chimeric antibody expression vector.

FIG. 67A shows the observation of tumor growth, wherein the mice were divided into groups (n=8) on the 11th day after inoculation and administrated on 11th and 18th days, and the doses of antibody-conjugates in the two groups were both 3 mg/kg, 1 mg/kg. FIG. 67B shows the observation regression of large-volume tumors, wherein the mice were divided into groups (n=8) on the 23rd day of inoculation and administrated on 23rd and 30th days, and the doses were 5 mg/kg for antibody-conjugate and 15 mg/kg for docetaxel.

FIG. 70 shows the test results of hematological index of Hu001c14-vcMMAE (Test substance number FD114-ADC) in cynomolgus monkey security experiment.

FIG. 71 shows the test results of hemagglutination index of Hu001c14-vcMMAE (Test substance number FD114-ADC) in cynomolgus monkey security experiment.

FIG. 72 shows the test results of plasma biochemical index of Hu001c14-vcMMAE (Test substance number FD114-ADC) in cynomolgus monkey security experiment.

MODES FOR CARRYING OUT THE PRESENT INVENTION

Figure 3:
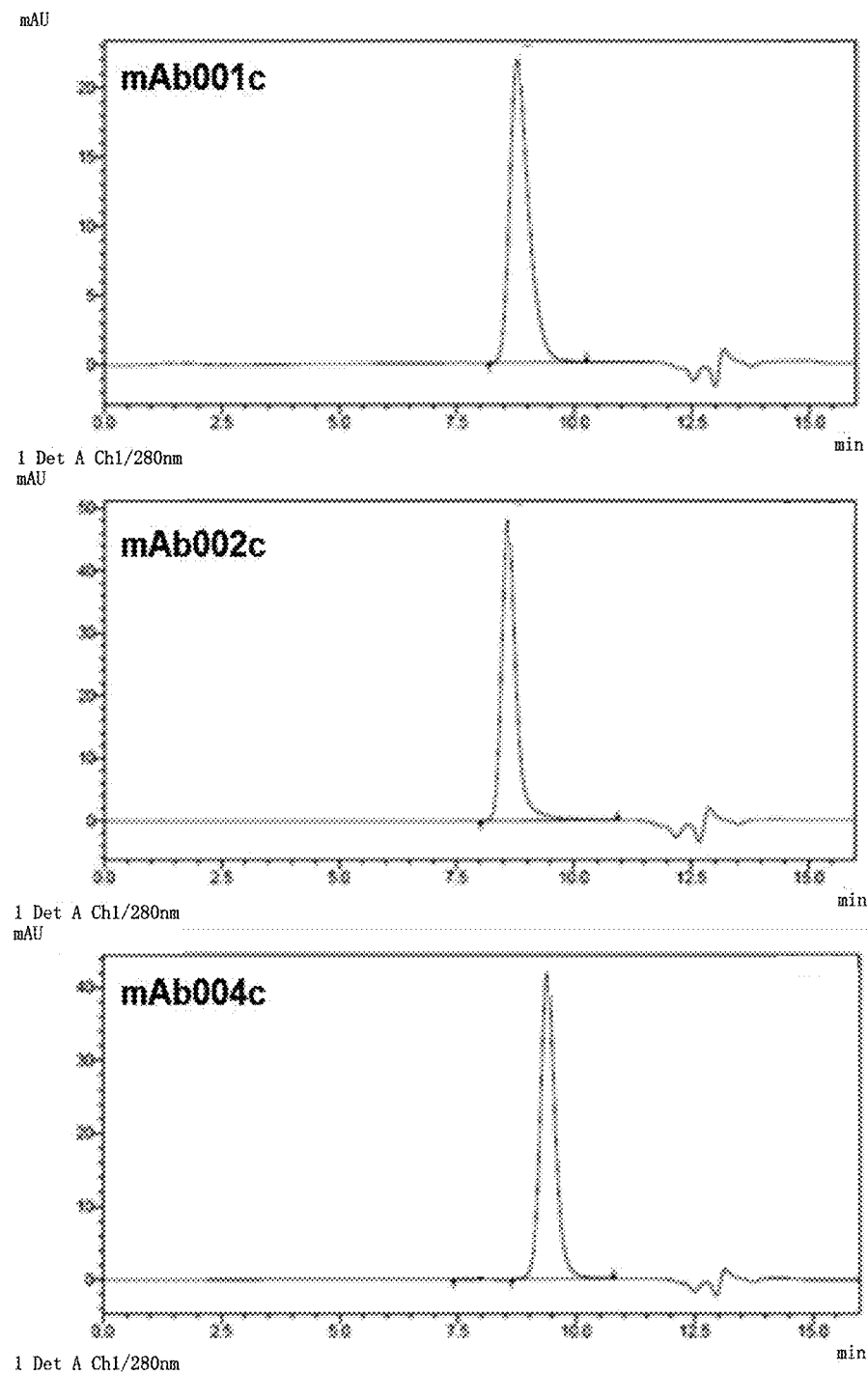
FIG. 3 shows the purification profile of the three human-mouse chimeric antibodies mAb001c, mAb002c, and mAb004c expressed by HEK293T cells using the MabSelect™ SuRe™ column.

Through extensive and intensive research, the inventors have unexpectedly obtained 5 anti-CD73 monoclonal antibodies after extensive screening, named mAb001 to mAb005, respectively. According to the activity test results, mAb001 (IgG1-κ), mAb002 (IgG1-κ), and mAb004 (IgG2b-κ) were selected to construct human-mouse chimeric antibodies mAb001c, mAb002c, and mAb004c. These antibodies can bind to CD73 antigen with high specificity, and the $EC_{50}$ values thereof determined by ELISA are 0.024 nM, 0.016 nM and 0.038 nM, respectively. In addition, these antibodies have significant anti-tumor activity without significant toxic and side effects to the mammal. In addition, the humanized antibodies designed based on mAb001c and mAb002c and the corresponding antibody-drug conjugates (ADCs) also have excellent characteristics. In addition, the CD73 antibody-drug conjugate product obtained by using the novel linker of the present invention has the advantages of high uniformity and further improved stability in vitro and in vivo. The present invention has been completed on the basis of these studies.

Antibody

As used herein, the term "antibody" or "immunoglobulin" is a heterotetrameric glycoprotein of about 150,000 Da having the same structural characteristics, which consists of two identical light chains (L) and two identical heavy chains (H). Each light chain is linked to a heavy chain via a covalent disulfide bond, and different immunoglobulin isotypes have different numbers of disulfide bonds between the heavy chains. There are also regularly spaced intrachain disulfide bonds in each heavy and each light chain. Each heavy chain has a variable region (VH) at one end, followed by a plurality of constant regions. Each light chain has a variable region (VL) at one end and a constant region at the other end; the constant region of a light chain pairs with the first constant region of a heavy chain, and the variable region of a light chain pairs with the variable region of a heavy chain. Special amino acid residues form an interface between the variable regions of a light chain and a heavy chain.

As used herein, the term "variable" means that antibodies are different from each other in terms of sequence in certain parts of variable regions, which is responsible for the binding and specificity of various specific antibodies to their specific antigens. However, the variability is not distributed evenly throughout the variable regions of an antibody. It is concentrated in three segments called complementarity determining regions (CDRs) or hypervariable regions in the light and heavy chain variable regions. The conserved parts of variable regions are called framework regions (FRs). Each of the variable regions of naturally occurring heavy and light chains comprises four FR regions, which are generally in a β-sheet configuration, joined by the three CDRs forming a linking loop, and in some cases, may form a partial β-sheet structure. The CDRs in each chain are closely linked together via the FR regions, and together with the CDRs of the other chain, form the antigen binding site of an antibody (see Kabat et al., NIH Publ. No. 91-3242, Vol. I, pp. 647-669 (1991)). The constant regions are not directly involved in the binding of an antibody to an antigen, however, they exhibit different effector functions, for example, and they are involved in the antibody-dependent cytotoxicity of an antibody.

The "light chain" of a vertebrate antibody (immunoglobulin) can be classified into one of the two obviously different classes (referred to as κ and λ) depending on the amino acid sequence of its constant region. Immunoglobulins can be classified into different classes depending on the amino acid sequences of their heavy chain constant regions. There are mainly five classes of immunoglobulins: IgA, IgD, IgE, IgG, and IgM, some of which can be further classified into subclasses (isotypes), such as IgG1, IgG2, IgG3, IgG4, IgA, and IgA2. The heavy chain constant regions corresponding to different classes of immunoglobulins are called α, δ, ε, γ, and μ, respectively. The subunit structures and three-dimensional configurations of different classes of immunoglobulins are well known for those skilled in the art.

In general, the antigen binding characteristics of an antibody can be described by three specific regions located in the heavy and light chain variable regions, called complementarity determining regions (CDRs), which divide the variable region into four framework regions (FRs); the amino acid sequences of the four FRs are relatively conservative and are not directly involved in the binding reaction. These CDRs form a ring structure, and approach to each other in the steric structure by virtue of the β-sheets formed by the FRs between them, and the CDRs on the heavy chain and the CDRs on the corresponding light chain constitute the antigen-binding site of an antibody. By comparison of the amino acid sequences of antibodies of the same type, it can be determined which amino acids form FRs or CDRs.

The present invention includes not only an intact antibody, but also the fragments of the antibody having an immunological activity or a fusion protein formed by the antibody and another sequence. Therefore, the present invention also includes fragments, derivatives and analogs of the antibody.

In the present invention, antibodies include murine, chimeric, humanized or fully human antibodies as prepared by techniques well known to those skilled in the art. Recombinant antibodies, such as chimeric and humanized monoclonal antibodies, including human and non-human portions, can be obtained by standard DNA recombination techniques, all of which are useful antibodies. A chimeric antibody is a molecule in which different portions are derived from different animal species, for example, a chimeric antibody having a variable region from a monoclonal antibody from a mouse and a constant region from a human immunoglobulin (see, for example, U.S. Pat. Nos. 4,816,567 and 4,816,397, which are incorporated herein by reference in its entirety). A humanized antibody refers to an antibody molecule derived from a non-human species, which has one or more complementarity determining regions (CDRs) derived from a non-human species and framework regions derived from a human immunoglobulin molecule (see U.S. Pat. No. 5,585,089, which is incorporated herein by reference in its entirety). These chimeric and humanized monoclonal antibodies can be prepared by recombinant DNA techniques well known in the art.

In the present invention, an antibody may be monospecific, bispecific, trispecific, or multi specific.

In the present invention, the antibody of the present invention further includes a conservative variant thereof, which refers to a polypeptide formed by substitution of at most 10, preferably at most 8, more preferably at most 5, and most preferably at most 3 amino acids with amino acids having similar or analogous property, as compared to the amino acid sequence of the antibody of the present invention. These conservative variant polypeptides are preferably formed by carrying out the amino acid substitution according to Table A.

TABLE A

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Anti-CD73 Antibody

The present invention provides three types of CD73 targeting antibodies with high specificity and high affinity, which comprise a heavy chain and a light chain. The heavy chain comprises the amino acid sequence of heavy chain variable region (VH), and the light chain comprises the amino acid sequence of light chain variable region (VL).

Preferably, the amino acid sequence of heavy chain variable region (VH) and the amino acid sequence of light chain variable region (VL) comprise HCDR1, HCDR2, HCDR3, LCDR1, LCDR2 and LCDR3 having the following polypeptide sequences:

a1) HCDR1 is
SEQ ID NO. 1:
NYYIY,

SEQ ID NO. 10:
SYWMH,
or

SEQ ID NO. 21:
DYNMD;

a2) HCDR2 is
SEQ ID NO. 2:
WIYPGNLNIKYNEKFKG,

SEQ ID NO. 11:
EINPSNGRSNYNEKFKS,
or

SEQ ID NO. 22:
DINPNNGGSVYNQKFKG;

a3) HCDR3 is
SEQ ID NO. 3:
DDNYAWFAY,

SEQ ID NO. 12:
RGVSGNYFDY,
or

SEQ ID NO. 23:
ITGTGYWSFDV;

a4) LCDR1 is
SEQ ID NO. 4:
KASQDVSTAVA,

SEQ ID NO. 13:
KASQDINTYLS,
or

SEQ ID NO. 24:
RASENIYSNLA;

a5) LCDR2 is
SEQ ID NO. 5:
WTNTRHT,

SEQ ID NO. 14:
RSNILVD,
or

SEQ ID NO. 25:
GATNLAE;
or a6) LCDR3 is
SEQ ID NO. 6:
QQHYSTPFT;

SEQ ID NO. 15:
LQYDEFPYT,
or

SEQ ID NO. 26:
QHFWGIPWT;

a7) a sequence with CD73 binding affinity which is obtained through addition, deletion, modification and/or substitution of at least one amino acid of any amino acid sequence of the above amino acid sequences.

In another preferred embodiment, the sequence obtained through addition, deletion, modification and/or substitution of at least one amino acid is preferably an amino acid sequence having a homology of at least 80%, preferably at least 85%, more preferably at least 90%, and most preferably at least 95%.

Preferably, the antibody can inhibit the catalytic function of CD73 on the cell surface and recombinant CD73, and the antibody can be quickly internalized into intracellular lysosome.

The antibody of the present invention may be a double-chain or single-chain antibody, and may be selected from an animal-derived antibody, a chimeric antibody, a human-animal chimeric antibody, and preferably is a humanized antibody, and more preferably a fully humanized antibody.

The antibody derivative of the present invention may be a single-chain antibody, and/or an antibody fragment, for example, Fab, Fab', (Fab')$_2$ or other antibody derivatives known in the art, etc., and may be any one or more of IgA, IgD, IgE, IgG and IgM antibodies or other subtype antibodies.

In the present invention, the animal is preferably a mammal, such as mouse.

The antibody of the present invention may be a chimeric antibody, a humanized antibody, a CDR grafted and/or modified antibody that targets human CD73.

In a preferred embodiment of the present invention, any one or more sequences of SEQ ID NOs. 1-3, SEQ ID NOs. 10-12, and SEQ ID NOs. 21-23, or sequences thereof that are obtained through addition, deletion, modification and/or substitution of at least one amino acid and have CD73 binding affinity, are located in the CDRs of heavy chain variable region (VH).

In a preferred embodiment of the present invention, any one or more sequences of SEQ ID NOs. 4-6, SEQ ID NOs. 13-15, and SEQ ID NOs. 24-26, or sequences thereof that are obtained through addition, deletion, modification and/or substitution of at least one amino acid and have CD73 binding affinity, are located in the CDRs of light chain variable region (VL).

In a more preferred embodiment of the present invention, VH CDR1, CDR2, CDR3 are independently selected from any one or more sequences of SEQ ID NO. 1, SEQ ID NO. 2, and SEQ ID NO. 3, or selected from SEQ ID NO. 10, SEQ ID NO. 11, and SEQ ID NO. 12, or selected from SEQ ID NO. 21, SEQ ID NO. 22, and SEQ ID NO. 23, or sequences thereof that are obtained through addition, deletion, modification and/or substitution of at least one amino acid and have CD73 binding affinity; VL CDR1, CDR2, CDR3 are independently selected from any one or more sequences of SEQ ID NO. 4, SEQ ID NO. 5, and SEQ ID NO. 6, or selected from SEQ ID NO. 13, SEQ ID NO. 14, and SEQ ID NO. 15, or selected from SEQ ID NO. 24, SEQ ID NO. 25, and SEQ ID NO. 26, or sequences thereof that are obtained through addition, deletion, modification and/or substitution of at least one amino acid and have CD73 binding affinity.

In above content of the present invention, the number of the added, deleted, modified and/or substituted amino acids, preferably does not exceed 40%, more preferably does not exceed 35%, is more preferably 1-33%, is more preferably 5-30%, is more preferably 10-25%, and is more preferably 15-20% of the total number of the amino acids of the initial amino acid sequence.

In the above content of the present invention, more preferably, the number of the added, deleted, modified and/or substituted amino acids, may be 1-7, more preferably 1-5, more preferably 1-3, and more preferably 1-2.

In another preferred embodiment, the antibody is the original murine antibody mAb001, mAb002, mAb003, mAb004, or mAb005.

In another preferred embodiment, the antibody is human-mouse chimeric antibody mAb001c, mAb001c-VK-SGS, mAb002c, mAb002c-VH-QG, mAb002c-VH-NA, mAb002c-VK-SG, mAb002c-VH-QG/VK-SG, mAb004c, mAb004c-VH-QG, or mAb004c-VH-NA.

In another preferred embodiment, the antibody is humanized antibody Hu001c-14, Hu001c-15, Hu001c-21, Hu001c-22, Hu001c-23, Hu001c-24, Hu001c-25, Hu001c-28, Hu001c-30, Hu001c-31, or Hu001c-32.

In another preferred embodiment, the antibody is humanized antibody Hu002c-2, Hu002c-3, Hu002c-4, Hu002c-6, Hu002c-7, Hu002c-8, Hu002c-10, Hu002c-11, Hu002c-12, Hu002c-14, Hu002c-15, or Hu001c-16.

In another preferred embodiment, the amino acid sequence ID numbers of the heavy chain and light chain variable regions (VH/VL) of the chimeric antibody are listed in Table 1.

In another preferred embodiment, the amino acid sequence ID numbers of the heavy chain and light chain variable regions (VH/VL) of the humanized antibody are listed in Table 2.

The three types of antibodies of the present invention can be used in combination, for constructing CAR constructs, recombinant immune cells containing CAR constructs, antibody drug conjugates, etc., and can also be used for (a) preparation of a detection reagent, detection plate or kit; and/or (b) preparation of a medicine for preventing and/or treating a CD73-related disease.

The representative meanings of each sequence involved in the sequence listing of the present invention are as follows:

| Sequence number | Sequence name |
| --- | --- |
| SEQ ID NO. 1 | mAb001 HCDR1 |
| SEQ ID NO. 2 | mAb001 HCDR2 |
| SEQ ID NO. 3 | mAb001 HCDR3 |
| SEQ ID NO. 4 | mAb001 LCDR1 |
| SEQ ID NO. 5 | mAb001 LCDR2 |
| SEQ ID NO. 6 | mAb001 LCDR3 |
| SEQ ID NO. 7 | mAb001-VH |
| SEQ ID NO. 8 | mAb001-VL |
| SEQ ID NO. 9 | mAb001-VL-SGS |
| SEQ ID NO. 10 | mAb002 HCDR1 |
| SEQ ID NO. 11 | mAb002 HCDR2 |
| SEQ ID NO. 12 | mAb002 HCDR3 |
| SEQ ID NO. 13 | mAb002 LCDR1 |
| SEQ ID NO. 14 | mAb002 LCDR2 |
| SEQ ID NO. 15 | mAb002 LCDR3 |
| SEQ ID NO. 16 | mAb002-VH |
| SEQ ID NO. 17 | mAb002-VH-QG |
| SEQ ID NO. 18 | mAb002-VH-NA |
| SEQ ID NO. 19 | mAb002-VL |
| SEQ ID NO. 20 | mAb002-VL-SG |
| SEQ ID NO. 21 | mAb004 HCDR1 |
| SEQ ID NO. 22 | mAb004 HCDR2 |
| SEQ ID NO. 23 | mAb004 HCDR3 |
| SEQ ID NO. 24 | mAb004 LCDR1 |
| SEQ ID NO. 25 | mAb004 LCDR2 |
| SEQ ID NO. 26 | mAb004 LCDR3 |
| SEQ ID NO. 27 | mAb004-VH |
| SEQ ID NO. 28 | mAb004-VH-QG |
| SEQ ID NO. 29 | mAb004-VH-NA |
| SEQ ID NO. 30 | mAb004-VL |
| SEQ ID NO. 31 | mAb001-VH__HuG.3 |
| SEQ ID NO. 32 | mAb001-VH__HuG.5 |
| SEQ ID NO. 33 | mAb001-VH__HuG.6 |
| SEQ ID NO. 34 | mAb001-VH__HuG.7 |
| SEQ ID NO. 35 | mAb001-VH__HuG.8 |
| SEQ ID NO. 36 | mAb001-VK__HuG.1 |
| SEQ ID NO. 37 | mAb001-VK__HuG.2 |
| SEQ ID NO. 38 | mAb002-VH__HuG0 |
| SEQ ID NO. 39 | mAb002-VH__HuG1 |
| SEQ ID NO. 40 | mAb002-VH__HuG2 |
| SEQ ID NO. 41 | mAb002-VH__HuG3 |
| SEQ ID NO. 42 | mAb002-VK__HuG1 |
| SEQ ID NO. 43 | mAb002-VK__HuG2 |
| SEQ ID NO. 44 | mAb002-VK__HuG3 |

-continued

| Sequence number | Sequence name |
|---|---|
| SEQ ID NO. 45 | mAb001-VH_HuG.9 |
| SEQ ID NO. 46 | mAb001-VH_HuG.10 |
| SEQ ID NO. 47 | mAb001-VK_HuG.0 |
| SEQ ID NO. 48 | Extracellular domain of human CD73 protein |
| SEQ ID NO. 49 | MEDI9447 VH |
| SEQ ID NO. 50 | MEDI9447 VL |

Antibody Preparation

The sequence of the DNA molecule for the antibody or a fragment thereof according to the present invention can be obtained by conventional techniques, for example, methods such as PCR amplification or genomic library screening. In addition, the sequences encoding light chain and heavy chain can be fused together, to form a single-chain antibody.

Once a relevant sequence is obtained, the relevant sequence can be obtained in bulk using a recombination method. This is usually carried out by cloning the sequence into a vector, transforming a cell with the vector, and then separating the relevant sequence from the proliferated host cell by conventional methods.

In addition, a relevant sequence can be synthesized artificially, especially when the fragment is short in length. Usually, several small fragments are synthesized first, and then are linked together to obtain a fragment with a long sequence.

At present, it is possible to obtain a DNA sequence encoding the antibody of the present invention (or fragments thereof, or derivatives thereof) completely by chemical synthesis. The DNA sequence can then be introduced into a variety of existing DNA molecules (or, for example, vectors) and cells known in the art. In addition, mutations can also be introduced into the protein sequences of the present invention by chemical synthesis.

The present invention further relates to a vector comprising said suitable DNA sequence and a suitable promoter or a control sequence. These vectors can be used to transform suitable host cells to enable them to express protein.

The host cell can be a prokaryotic cell, such as a bacterial cell; or a lower eukaryotic cell, such as a yeast cell; or a higher eukaryotic cell, such as a mammalian cell. Preferred animal cells include, but are not limited to, CHO-S, HEK-293 cells.

In general, under conditions suitable for expression of the antibody according to the present invention, the host cell obtained is cultured. Then, the antibody of the present invention is purified by using conventional immunoglobulin purification steps, for example, the conventional separation and purification means well known to those skilled in the art, such as protein A-Sepharose, hydroxyapatite chromatography, gel electrophoresis, dialysis, ion exchange chromatography, hydrophobic chromatography, molecular sieve chromatography or affinity chromatography.

The monoclonal antibody obtained can be identified by conventional means. For example, the binding specificity of a monoclonal antibody can be determined by immunoprecipitation or an in vitro binding assay (such as radioimmunoassay (RIA) or enzyme-linked immunosorbent assay (ELISA)). The binding affinity of a monoclonal antibody can be determined by, for example, the Scatchard analysis (Munson et al., Anal. Biochem. 107: 220 (1980)).

The antibody according to the present invention can be expressed in a cell or on the cell membrane, or is secreted extracellularly. If necessary, the recombinant protein can be separated and purified by various separation methods according to its physical, chemical, and other properties. These methods are well known to those skilled in the art. The examples of these methods comprise, but are not limited to, conventional renaturation treatment, treatment by protein precipitant (such as salt precipitation), centrifugation, cell lysis by osmosis, ultrasonic treatment, super centrifugation, molecular sieve chromatography (gel chromatography), adsorption chromatography, ion exchange chromatography, high performance liquid chromatography (HPLC), and any other liquid chromatography, and the combination thereof.

Antibody-Drug Conjugate (ADC)

The present invention also provides an antibody-drug conjugate (ADC) based on the antibody according to the present invention.

Typically, the antibody-drug conjugate comprises the antibody and an effector molecule, wherein the antibody is conjugated to the effector molecule, and chemical conjugation is preferred. Preferably, the effector molecule is a therapeutically active drug. In addition, the effector molecule may be one or more of a toxic protein, a chemotherapeutic drug, a small-molecule drug or a radionuclide.

The antibody according to present invention and the effector molecule may be coupled by a coupling agent. Examples of the coupling agent may be any one or more of a non-selective coupling agent, a coupling agent utilizing a carboxyl group, a peptide chain, and a coupling agent utilizing a disulfide bond. The non-selective coupling agent refers to a compound that results in a linkage between an effector molecule and an antibody via a covalent bond, such as glutaraldehyde, etc. The coupling agent utilizing a carboxyl group may be any one or more of cis-aconitic anhydride coupling agents (such as cis-aconitic anhydride) and acyl hydrazone coupling agents (the coupling site is acyl hydrazone).

Certain residues on an antibody (such as Cys or Lys, etc.) are used to link a variety of functional groups, including imaging agents (such as chromophores and fluorophores), diagnostic agents (such as MM contrast agents and radio-isotopes), stabilizers (such as poly(ethylene glycol)) and therapeutic agents. An antibody can be conjugated to a functional agent to form a conjugate of the antibody-functional agent. A functional agent (e.g. a drug, a detection reagent, a stabilizer) is conjugated (covalently linked) to an antibody. A functional agent can be linked to an antibody either directly or indirectly via a linker.

Typical conjugation manners suitable for the present invention include both K-Lock and C-Lock conjugation manners. In the K-Lock conjugation manner, a drug molecule is conjugated to the lysine (K) residue in an antibody sequence; in the C-Lock conjugation manner, a drug molecule is coupled to the cysteine (C) residue in an antibody sequence.

Antibodies can be conjugated to drugs to form antibody-drug conjugates (ADCs). Typically, an ADC comprises a linker between a drug and an antibody. The linker can be a degradable or non-degradable linker. Typically, degradable linkers are easily degraded in an intracellular environment, for example, the linker is degraded at the target site, thereby releasing the drug from the antibody. Suitable degradable linkers include, for example, enzyme-degradable linkers, including peptidyl-containing linkers that can be degraded by protease (e.g. lysosomal protease or endosomal protease) in a cell, or sugar linkers, for example, glucuronide-containing linkers that can be degraded by glucuronidase. Peptidyl linkers may include, for example, dipeptides, such as valine-citrulline, phenylalanine-lysine or valine-alanine.

Other suitable degradable linkers include, for example, pH sensitive linkers (e.g. linkers that are hydrolyzed at a pH of below 5.5, such as hydrazone linkers) and linkers that are degraded under reducing conditions (e.g. disulfide-bond linkers). A non-degradable linker typically releases a drug under conditions that the antibody is hydrolyzed by protease.

Prior to linkage to an antibody, a linker has a reactive group capable of reacting with certain amino acid residues, and the linkage is achieved by the reactive group. A thiol-specific reactive group is preferred, and includes, for example, a maleimide compound, a halogenated (e.g. iodo-, bromo- or chloro-substituted) amide; a halogenated (e.g. iodo-, bromo- or chloro-substituted) ester; a halogenated (e.g. iodo-, bromo- or chloro-substituted) methyl ketone, a benzyl halide (e.g. iodide, bromide or chloride); vinyl sulfone, pyridyl disulfide; a mercury derivative such as 3,6-di-(mercurymethyl)dioxane, wherein the counter ion is $CH^3COO^-$, $Cl^-$ or $NO^{3-}$; and polymethylene dimethyl sulfide thiosulfonate. The linker may include, for example, a maleimide linked to an antibody via thiosuccimide.

A drug may be any cytotoxic drug which inhibits cell growth or immunosuppression. In an embodiment, an antibody is linked to a drug via a linker, and the drug has a functional group that can form a bond with the linker. For example, a drug may have an amino group, a carboxyl group, a thiol group, a hydroxyl group, or a ketone group that can form a bond with a linker. When a drug is directly linked to a linker, the drug has a reactive group before being linked to an antibody.

Useful drugs include, for example, anti-tubulin drugs, DNA minor groove binding agents, DNA replication inhibitors, alkylating agents, antibiotics, folic acid antagonists, antimetabolites, chemotherapy sensitizers, topoisomerase inhibitors, vinca alkaloids, etc. Examples of particularly useful cytotoxic drugs include, for example, DNA minor groove binding agents, DNA alkylating agents, and tubulin inhibitors; typical cytotoxic drugs include, for example, auristatins, camptothecins, docamycin/duocarmycins, etoposides, maytansines and maytansinoids (e.g. DM1 and DM4), taxanes, benzodiazepines or benzodiazepine containing drugs (e.g. pyrrolo[1,4]benzodiazepines (PBDs), indolinobenzodiazepines and oxazolidinobenzodiazepines), and vinca alkaloids.

In the present invention, a drug-linker can be used to form an ADC in a simple step. In other embodiments, a bifunctional linker compound can be used to form an ADC in a two-step or multi-step process. For example, a cysteine residue is reacted with the reactive moiety of a linker in a first step, and then the functional group on the linker is reacted with a drug in the subsequent step, so as to form an ADC.

In general, the functional group on a linker is selected so that it can specifically react with the suitable reactive group on a drug moiety. As a non-limiting example, an azide-based moiety can be used to specifically react with the reactive alkynyl group on a drug moiety. The drug is covalently bound to the linker by 1,3-dipolar cycloaddition between the azide and alkynyl group. Other useful functional groups include, for example, ketones and aldehydes (suitable for reacting with hydrazides and alkoxyamines), phosphines (suitable for reacting with azides); isocyanates and isothiocyanates (suitable for reacting with amines and alcohols); and activated esters, for example, N-hydroxysuccinimide esters (suitable for reacting with amines and alcohols). These and other linkage strategies, for example, those described in "Bioconjugation Technology" (2nd Edition (Elsevier)), are well known to those skilled in the art. Those skilled in the art could understand that when a complementary pair of reactive functional groups are selected for a selective reaction between a drug moiety and a linker, each member of the complementary pair can be used for the linker, and can also be used for the drug.

The present invention further provides a method for preparing an ADC, which may further comprise: under conditions sufficient to form an antibody-drug conjugate (ADC), binding an antibody to a drug-linker compound.

In certain embodiments, the method according to the present invention comprises: under conditions sufficient to form an antibody-linker conjugate, binding an antibody to a bifunctional linker compound. In these embodiments, the method according to the present invention further comprises: under conditions sufficient to covalently link the drug moiety to the antibody via a linker, binding the antibody-linker conjugate to the drug moiety.

In some embodiments, an antibody-drug conjugate (ADC) has a formula as follows:

wherein:
Ab is an antibody,
LU is a linker;
D is a drug;
and the subscript p is a value selected from 1 to 10, preferably from 1 to 8.

Drug

As used herein, the term "drug" refers to any compound possessing a desired biological activity and a reactive functional group available for preparing the conjugate of the invention. The desired biological activity includes activity useful in the diagnosis, cure, mitigation, treatment, or prevention of a disease in human or other animal. Thus, so long as it has the needed reactive functional group, the compound involved by the term "drug" include drugs identified in the official national pharmacopeia as well as e.g., official Homeopathic Pharmacopeia of the United States, or official National Formulary, or any supplements thereof. Exemplary drugs are set forth in the Physician's Desk Reference (PDR) and in the Orange Book maintained by the U.S. Food and Drug Administration (FDA). It should be understood that, as new drugs are continually discovered and developed, these drugs shall also be incorporated into the "drug" of the drug conjugates of the present invention.

The drugs useful to constitute the ADC of the present invention include, but are not limited to, cytotoxic agents (such as small molecule cytotoxic drugs).

The term "cytotoxic agents" refer to substances that inhibit or block cell expression activity, cell function and/or result in cell destruction. The term includes radioisotopes, chemotherapeutics, and toxins, such as small-molecular toxins or enzymatically active toxins (including fragments and/or variants thereof) derived from bacteria, fungi, plants or animals. Examples of cytotoxic agents include, but are not limited to: Auristatins (for example, Auristatin E, Auristatin F, MMAE and MMAF), chlortetracycline, metotanol, ricin, ricin A-chain, cobustatin, dokamicin, Dorastatin, adriamycin, daunorubicin, paclitaxel, cisplatin, cc1065, ethidium bromide, mitomycin, etoposide, tenoposide, vincristine, vinblastine, colchicine, dihydroxyanthracnose diketone, actinomycin, diphtheria toxin, *Pseudomonas* exotoxin (PE) A, PE40, abrin, abrin A chain, modeccin A chain, α-Sarcina, gelonin, mitogellin, retstrictocin, phenomycin, enomycin, curicin, crocotin, calicheamicins, *Sapaonaria officinalis* inhibitor, as well as glucocorticoid and other chemotherapy agents, as well as radioisotopes such as $At^{211}$, $I^{131}$, $I^{125}$, $Y^{90}$, $Re^{186}$, $Re^{188}$, $Sm^{153}$, $Bi^{212}$ or $Bi^{213}$, $P^{32}$ and Lu (including $Lu^{177}$). Antibodies can also be conjugated to anticancer prodrug activating enzymes that can convert a prodrug into the active form.

The preferred small molecular drug is a compound with high cytotoxicity, preferably is monomethylauristatin, galactomycin, medenin, and a combination thereof and more preferably is monomethylolastatin-E (MMAE), monomethylolastatin-D (MMAD), monomethylolastatin-F (MMAF), and a combination thereof.

Preferably, the drug is: a cytotoxic drug for cancer therapy; a protein or polypeptide possessing a desired biological activity, such as a toxin, e.g., abrin, ricin A, *pseudomonas* exotoxin, and diphtheria toxin; any other suitable protein, including tumor necrosis factor, α-interferon, β-interferon, neuronal growth factor, platelet derived growth factor, tissue plasminogen activator, and biological response modifier, for example, lymphokine, interleukin-1 (IL-1), interleukin-2 (IL-2), interleukin-6 (IL-6), granulocyte macrophage colony stimulating factor (GM-CSF), granulocyte colony stimulating factor, or any other growth factor.

One preferred drug useful in the present invention is maytansine or maytansinoids. Maytansine inhibits cell proliferation by inhibiting the formation of microtubules from tubulins. Maytansinoids are derivatives of maytansine. Both maytansine and maytansinoids are highly cytotoxic, but they are greatly limited for clinical use in cancer therapy due to poor selectivity for tumors. However, a high cytotoxicity enables them to be attractive drug moieties in ADCs. The structure shown below is deacetyl-maytansine.

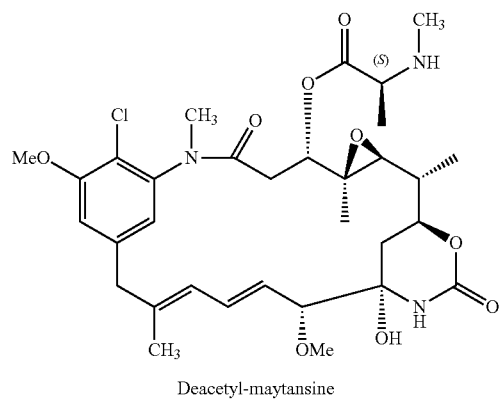

Deacetyl-maytansine

Another preferred drug useful in the present invention is auristatins. Auristatins are synthetic analogues of Dolastatin 10, which is a polypeptide isolated from marine mollusk Aplysia having biological activity. Dolastatin 10 inhibits tubulin polymerization by binding to tubulin at the same domain as anticancer drug vincristine. Dolastitin 10, auristatin PE, and auristatin E are all linear peptides having four amino acids, three of which are unique to the dolastatin class compounds, and a C-terminal amide group. Two representative auristatins, monomethyl auristatin E (MMAE) and monomethyl auristatin F (MMAF), are preferred drug moiety candidates for ADCs.

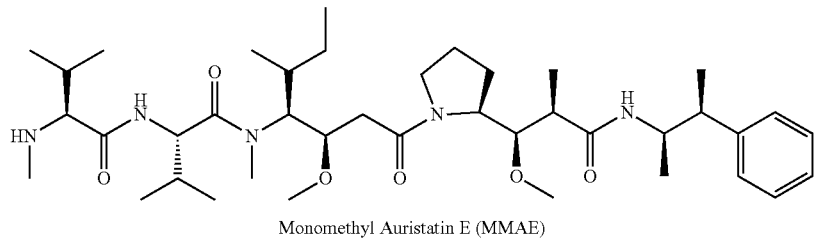

Monomethyl Auristatin E (MMAE)

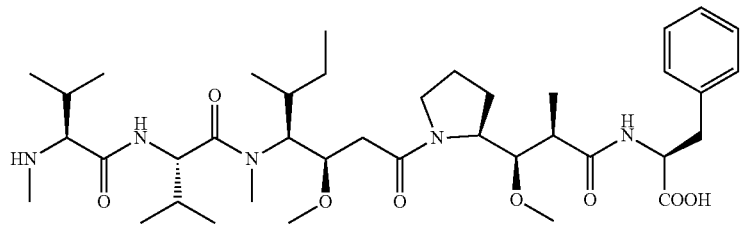

Monomethyl Auristatin F (MMAF)

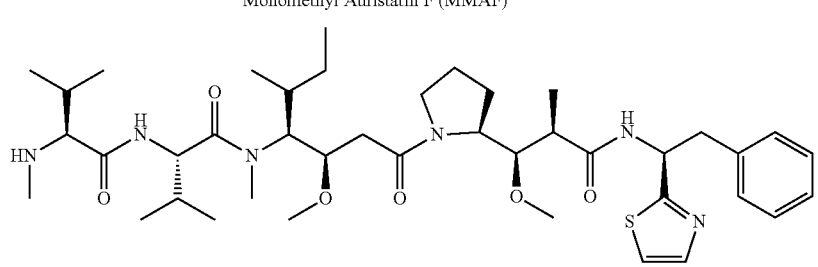

Monomethyl Dolastin 10 (MMAD)

Yet another preferred drug useful in the present invention is pyrrolo [2,1-c][1,4] benzodiazepines (PBDs) or PBD dimers. PBDs are a family of natural products produced by *Streptomyces* species with a unique characteristic of forming non-distortive covalent adducts in DNA minor groove, specifically at purine-guanine-purine sequences. There is a growing interest in using PBDs as part of a small-molecule strategy for targeting and locking DNA sequences and also as novel anticancer and antibacterial agents. The dimer, which is obtained by joining two PBD units together through their C8/C8'-hydroxyl functionality via a flexible alkylene linker, has increased biological activity. PBD dimers are deemed to lead to sequence-selective DNA lesions such as palindromic 5'-Pu-GATC-Py-3' interstrand crosslinks, which mainly account for their biological activity. These compounds have been shown to be highly useful cytotoxic agents and good drug candidates for ADCs.

of coordinating with a linker through an amide bond of the linker, such as through a basic amine (primary or second amine), like the cytotoxins having structures as shown in any of the above D1-D14.

CD73 Antibody-Drug Conjugate

The present invention relates to an antibody-drug conjugate, and more specifically, the present invention relates to a CD73 antibody-drug conjugate with therapeutic applications. The anti-CD73 antibody can be coupled to a chemotherapeutic drug or a small molecule toxin through a linker. The invention also relates to a method for treating mammalian cells or related pathological conditions using the anti-CD73 antibody-drug conjugate.

A novel disubstituted maleimide linker is applied for coupling the CD73-targeting antibody in the present invention. The linker can full/partially cross-couple the reduced cysteine sulfhydryl group of the disulfide bond in the light

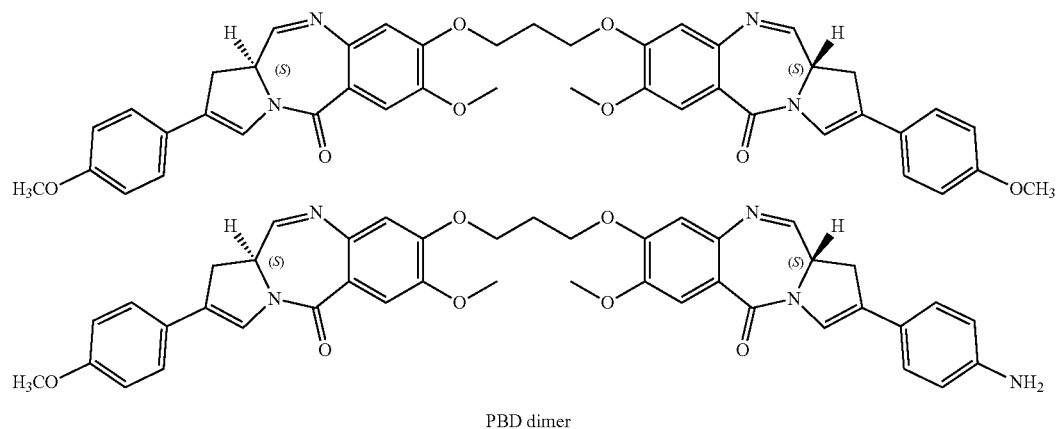

PBD dimer

Still yet another preferred drug useful in the present invention is PNU-159682 derivative. PNU-159682 is a main active metabolite of Nemorubicin in human liver microsomes, and has an activity 3000 times higher than that of MMDX or doxorubicin.

chain-heavy chain and heavy chain-heavy chain of the antibody. Compared with traditional antibody-drug conjugates, the antibody-drug conjugate targeting CD73 obtained by using this coupling method has a narrow drug/antibody ratio (DAR) distribution.

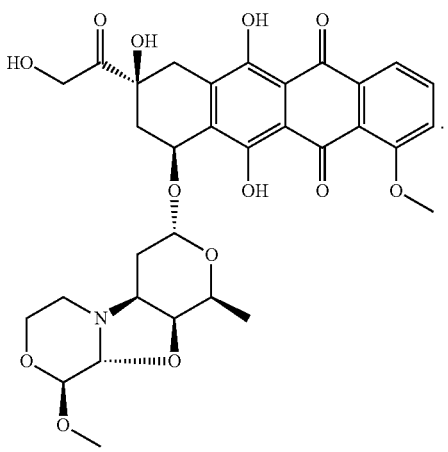

PNU-159682

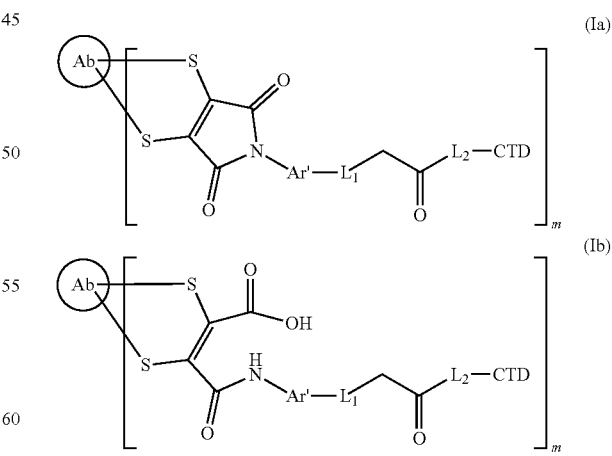

In another aspect, the drugs are not limited to abovementioned categories and include all those useful in ADCs. Especially, the drugs may include cytotoxins that are capable wherein, Ar' is selected from the group consisting of: substituted or unsubstituted C6-C10 arylene, and substituted or unsubstituted 5-12 membered heteroarylene;

$L_1$ is —O(CH$_2$CH$_2$O)$_n$— linked to the Ar' group, wherein n is selected from any integer from 1-20.

$L_2$ is a chemical bond, or AA-PAB structure; wherein AA is a polypeptide fragment consisted of 2-4 amino acids, and PAB is p-aminobenzylcarbamoyl;

CTD is a cytotoxic small molecule drug bonded to $L_2$ through an amide bond.

m is 3.8-4.2;

Ab is an antibody targeting CD73.

The present invention provides a coupling method that couples a small molecule toxin to an antibody targeting CD73 through a specific linker, and greatly improves the tumor cell killing capability of the antibody without changing the affinity of the antibody.

The present invention provides a linker or coupling reagent, which comprises a diarylthio maleimide unit and a coupling group. The diarylthio maleamide unit is used for crosslinking with the interchain sulfhydryl of the antibody (upon reduction), while the coupling group is used to couple with the small molecule drug or a drug-linker unit. Compared to traditional ADCs with mono-dentate linker, the ADCs of the present invention are homogeneous and have stronger stability due to the bidentate binding between the diarylthio maleamide unit and the two sulfur atoms of the opened cysteine-cysteine disulfide bond in the antibody. Therefore, they will have an increased half-life in vivo, a reduced amount of systemically released cytotoxins, and safer drug properties than ADCs with mono-dentate linker.

In another aspect, the drug-linker units can be coupled to antibody via the linkers, producing partially inter-chain crosslinked conjugates. Compared to traditional ADCs, the antibody drug conjugates prepared by the method of the present invention have much narrower DAR distribution, and thus have greatly improved structural and pharmacological homogeneities. The antibody drug conjugates can be used in targeted delivery of drugs to cell populations of interest, for example, tumor cells. The antibody drug conjugates binds specifically to cell surface proteins, and the binding complex will be internalized rapidly into the cells. The drug will be released in an active form and produce effects in cells. The antibody includes chimeric, humanized, or human antibody, antibody fragment that can bind to antigen; or Fc fused protein; or protein. The "drug" is a highly potent drug (see above), and can be polyethylene glycol in some case.

The conjugation product provided by the invention, albeit still a mixture, has a much narrower DAR-distribution, as compared to antibody drug conjugates produced traditionally. The average DAR obtained is close to 4, within an optimized DAR range of 2-4 of ADCs. In addition, the conjugation product does not contain or contain minimal naked antibodies (DAR=0), which are ineffective for cell killing. Also, the conjugation product does not contain heavily conjugated antibodies (DAR=8), which will be cleared more rapidly than those with low DAR values. As a result, the ADC product provided in the invention shows much improved homogeneity.

Linker-Drug Conjugate

In the present invention, the linker-drug conjugate comprises the substituted maleimide linker-drug conjugate as shown in formula Ic or a pharmaceutically acceptable salt or solvent compound thereof;

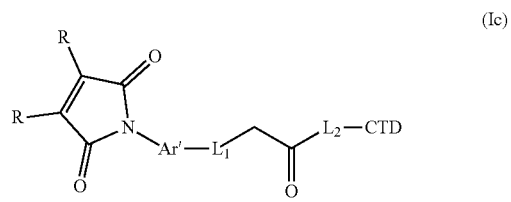

(Ic)

wherein,

R is X or ArS—,

X is selected from the group consisting of halogen, preferably bromine or iodine;

Ar' is selected from the group consisting of: substituted or unsubstituted C6-C10 aryl, substituted or unsubstituted 5-12 membered heteroaryl, substituted or unsubstituted C6-C10 arylene, and substituted or unsubstituted 5-12 membered heteroarylene;

$L_1$ is —O(CH$_2$CH$_2$O)$_n$— linked to the Ar' group, wherein n is selected from any integer from 1-20, preferably any integer from 1-10.

$L_2$ is a chemical bond or AA-PAB structure; wherein AA is a dipeptide or tripeptide or tetrapeptide fragment (i.e., a fragment formed by 2-4 amino acids connected by a peptide bond), and PAB is p-aminobenzylcarbamoyl;

CTD is a cytotoxic small molecule drug bonded to $L_2$ through an amide bond and/or a drug for treating autoimmune diseases and anti-inflammatory.

The compound of formula Ic is selected from the group consisting of:

Compound Ic-1

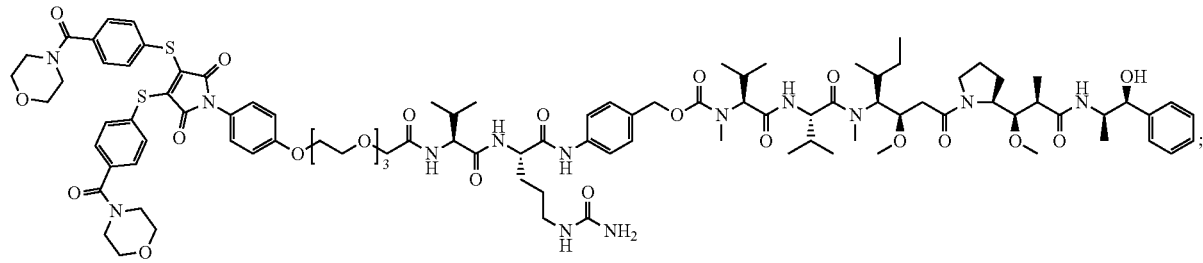

-continued
Compound Ic-2
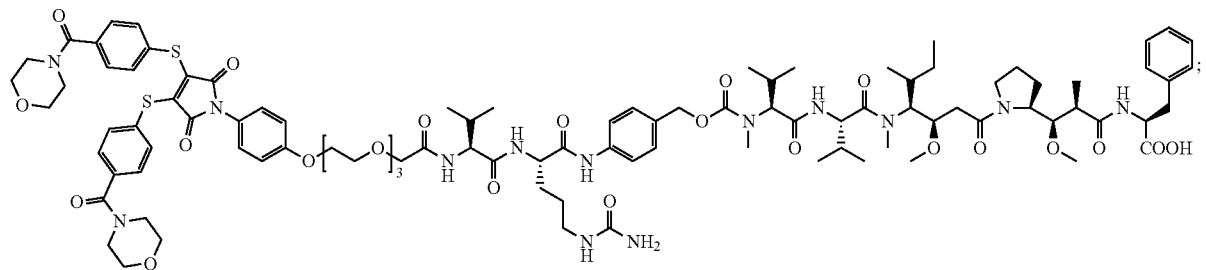
Compound Ic-3
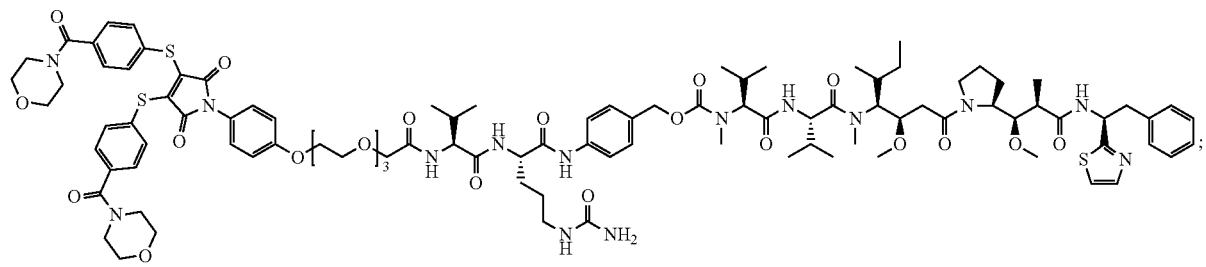
Compound Ic-4
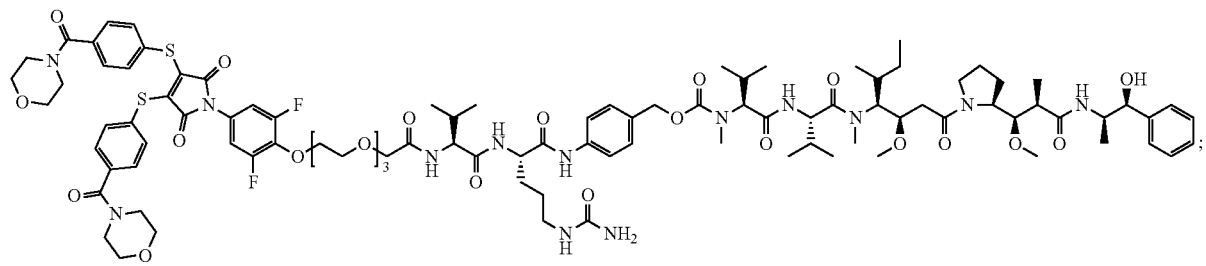
Compound Ic-5
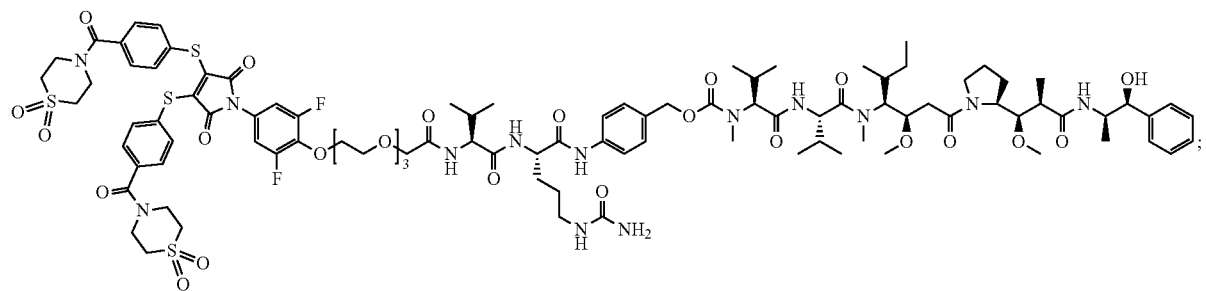
Compound Ic-6
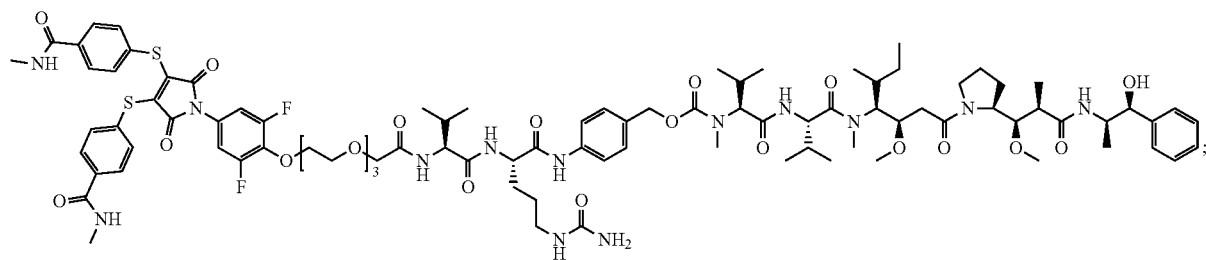

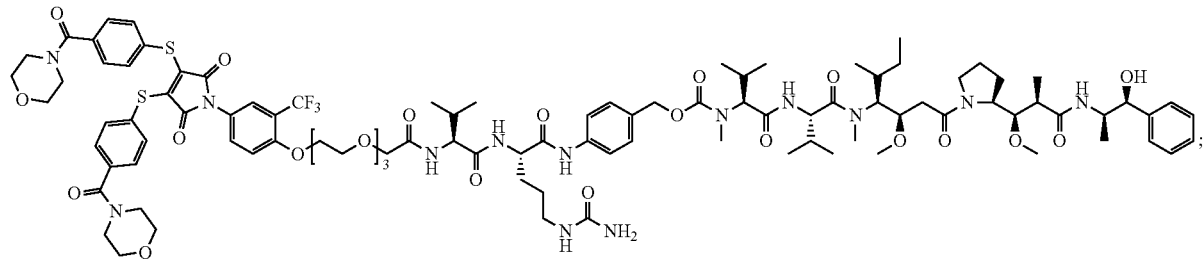

Compound Ic-7

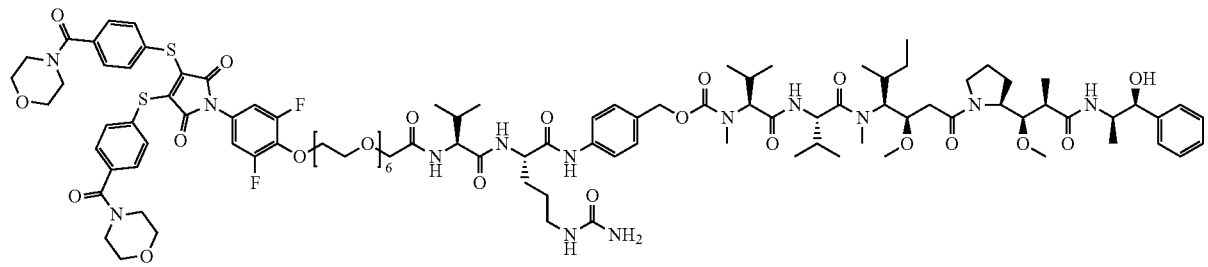

Compound Ic-8 and the like.

Synthesis and Preparation of Compounds as Shown by Formula Ic

The general preparation process of the compound shown by formula Ic is as follows:

Intermediate A is obtained by reacting n-glycol with tert-butyl bromoacetate, then Intermediate A is reacted with a substituted nitrofluorobenzene for aromatic nucleophilic substitution to obtain intermediate B. In addition, Intermediate B can also be obtained by reacting intermediate F protected by p-toluenesulfonate with a substituted nitrofluorophenol. The nitro group in Intermediate B is reduced into amino to obtain Intermediate C, which is then cyclized with 2,3-dibromomaleic anhydride to obtain Intermediate D, which is then substituted with arylthiophenol to obtain linker fragment molecule E. A series of molecules F can be obtained by condensing with a linker carrying dipeptide/tripeptide-PAB cytotoxic drug. The reaction route is as follows:

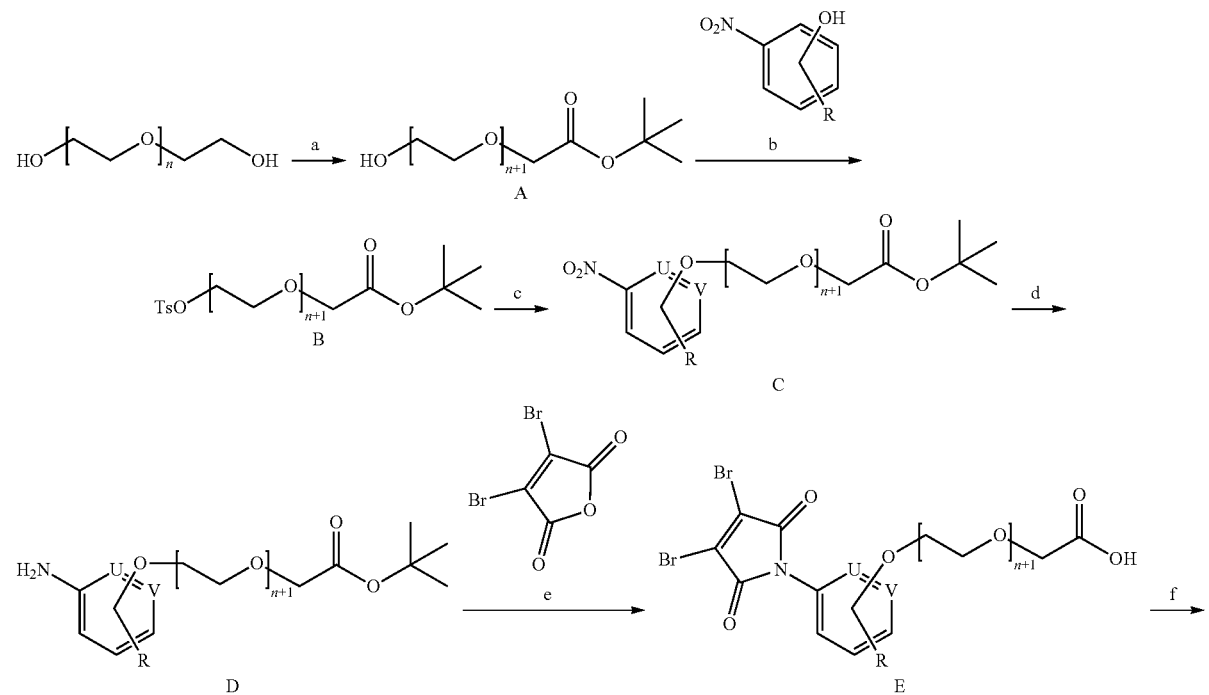

-continued

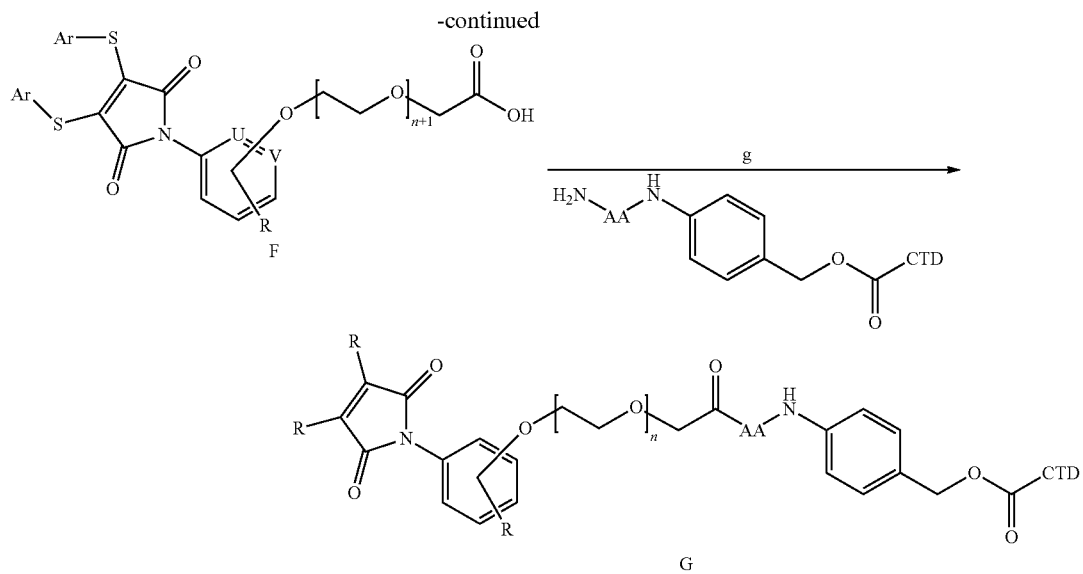

Compound Ic-4 is taken as an example to illustrate the preparation process:

washed once with saturated brine, and dried over anhydrous sodium sulfate and then the solvent was removed via rotary Compound Ic-4

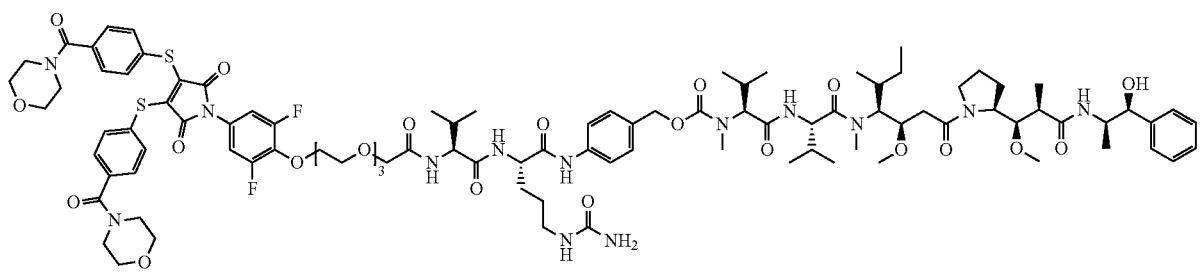

1.1.1 Intermediate A-1 (Step a)

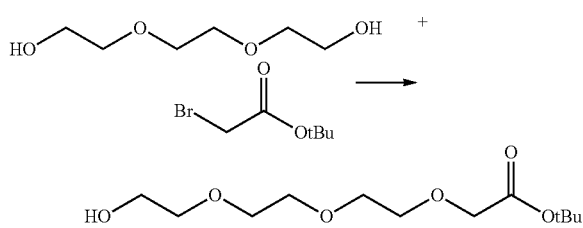

Triethylene glycol (92 g, 613 mmol) was dissolved in tBuOH (200 ml). The obtained solution was placed in ice bath, KOtBu (22.91 g, 204 mmol) was added thereto, and stirred for 30 minutes. Subsequently, tert-butyl bromoacetate (39.8 g, 204 mmol) dissolved in tBuOH (40 ml) was added dropwise under the protection of argon, and the obtained mixture was stirred overnight at room temperature. TLC on the next day indicated that the reaction was completed. Tert-butanol was removed via rotary evaporation. The residue was added into 400 ml of dichloromethane, and the organic phase was washed with 400 ml of water. The obtained aqueous phase was extracted once with 300 ml of dichloromethane. The organic phases were combined and evaporation. The obtained crude was subjected to column chromatography (petroleum ether: ethyl acetate=3:1 to 1:1) to obtain intermediate A-1 (24 g, 44.5% yield), as a yellow oily product.

1.1.2 Intermediate B-1 (Step b)

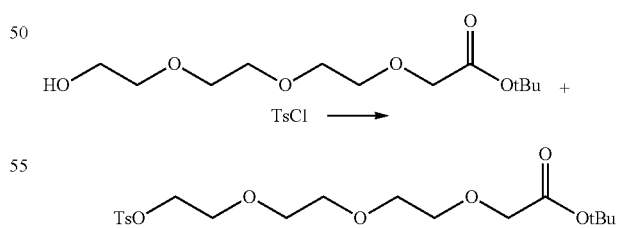

In a 250 ml round bottom flask, intermediate A-1 (4 g, 15.13 mmol), triethylamine (2.53 ml, 18.16 mmol) and dimethylaminopyridine (0.370 g, 3.03 mmol) were dissolved in 100 ml dichloromethane dried with molecular sieve and then stirred. Subsequently, p-toluene sulfonyl chloride (3.17 g, 16.65 mmol) was added in batches in an ice bath, and the obtained reaction mixture was stirred overnight under the protection of argon at room temperature.

Into the reaction system, 100 ml of dichloromethane was added for extraction, and then the organic phase was washed once with 200 ml of 1N diluted hydrochloric acid, twice with 200 ml water and once with 200 ml saturated brine, and dried with anhydrous sodium sulfate, and the solvent in organ phase was removed via rotary evaporation. The residue was isolated by column chromatography, in which the column was packed with 200-300 mesh silica gel and eluted with PE:EA=5:1-2:1. After rotary evaporation, Intermediate B-1 was obtained (2.8 g, 44.2% yield).

1.1.3 Intermediate C-1 (Step c)

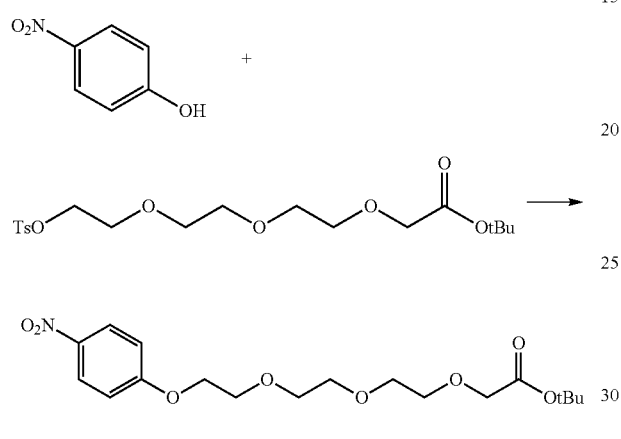

Intermediate B-1 (3 g, 7.19 mmol) and 2,6-difluoro-4-nitrophenol (1 g, 7.19 mmol) were dissolved in 20 ml DMF, $K_2CO_3$ (1.9 g, 14.4 mmol) was added, and the obtained solution was heated to 100 degrees and stirred for 5 hours. The solvent was removed via rotary evaporation. 200 ml of dichloromethane was added for dissolution. The obtained solution was extracted, washed respectively with 200 ml of 1N diluted hydrochloric acid, 200 ml of water and 200 ml of saturated brine, and dried with anhydrous sodium sulfate, and the solvent was removed via rotary evaporation. The residue was isolated by column chromatography, in which the column was packed with 200-300 mesh silica gel and eluted with PE:EA=5:1-3:1. The collected eluent was rotary evaporated off to obtain Intermediate C-1 (2 g, yield 72%).

1.1.4 Intermediate D-1 (Step d)

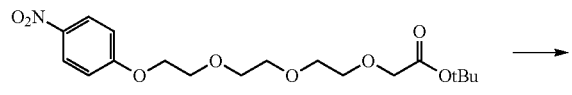

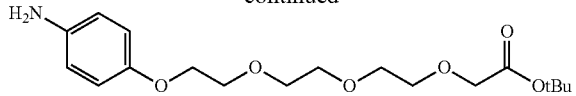

Intermediate B-1 (6 g, 15.57 mmol) was dissolved in 100 ml of dried ethanol and the solution was added into a reaction flask containing 1.2 g of 10% Pd—C. Hydrogenation reaction was performed for 6 hours (1 atm, 38° C.). TLC detected that the reaction was completed. The reaction solution was filtered through diatomaceous earth, the filter cake was rinsed with ethanol, and the filtrate was rotary evaporated off to obtain Intermediate D-1 (4.8 g, 87% yield), as a yellow oily product.

1.1.5 Compound E-1 (Step e)

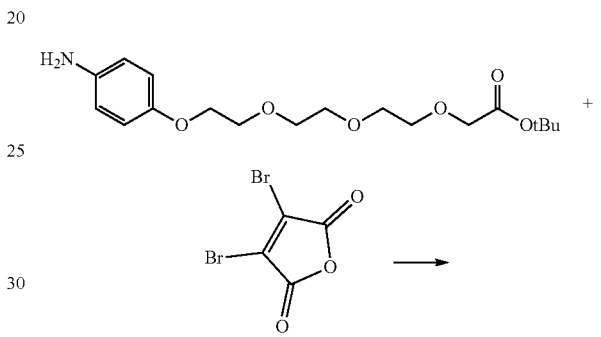

Intermediate D-1 (1.0 g, 2.81 mmol) was weighed and placed into a parallel reaction tube, AcOH (3 ml) was added under nitrogen protection, and stirred to dissolve. Subsequently, 3,4-dibromomaleic anhydride (0.72 g, 2.81 mmol) was slowly added. The obtained solution was heated to 110° C. and stirred overnight under the protection of nitrogen. TLC detected the reaction. The reaction solution was cooled to room temperature, then the solvent was removed via rotary evaporation, and toluene was added and mixture was rotary evaporated off twice to obtain brown oily compound E-1, which was directly used in the next reaction without purification.

1.1.6 Synthesis of Compound F-1 (Step f)

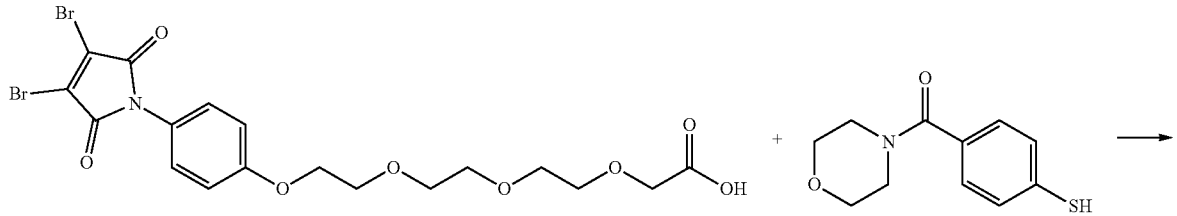

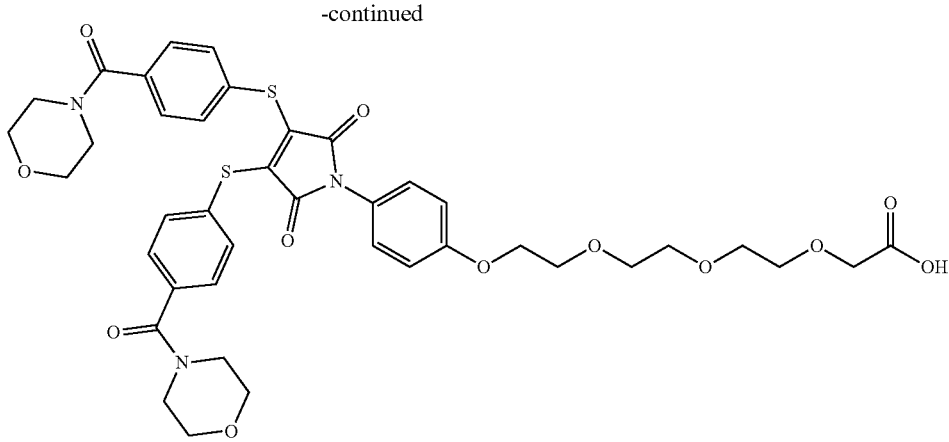

Compound E-1 (2.0 g, 3.72 mmol) was weighed and placed into a 100 ml round-bottomed flask, 30 ml anhydrous dichloromethane was added under nitrogen protection and stirred to dissolve. 4-(N-morpholine formamide) thiophenol (1.66 g, 7.45 mmol) was weighed, added into the reaction solution under nitrogen protection, and dissolved. DIPEA (1.3 mL ml, 7.45 mmol) was slowly added in a condition of ice bath. After the addition, the obtain solution was stirred for 5 minutes, and then the ice bath was removed. The obtained solution was stirred at room temperature for 2 hours under nitrogen protection. TLC detected the completion of the reaction.

The solvent was removed via evaporation under reduced pressure. The residue was isolated and purified by column chromatography (200-300 mesh silica gel), in which the column was packed and rinsed with dichloromethane, and then the polarity was increased slowly by rinsing with methanol of a concentration from 2% to 10%. The solvent in the collected eluent was evaporated off to obtain orange oily product F-1 (2.2 g, 72% yield). LC-MS (M⁺) theoretical value: 821.2, measured value: 821.3 (ESI, M+H⁺).

1.1.7 Synthesis of Compound G-1 (Ic-1) (Step g)

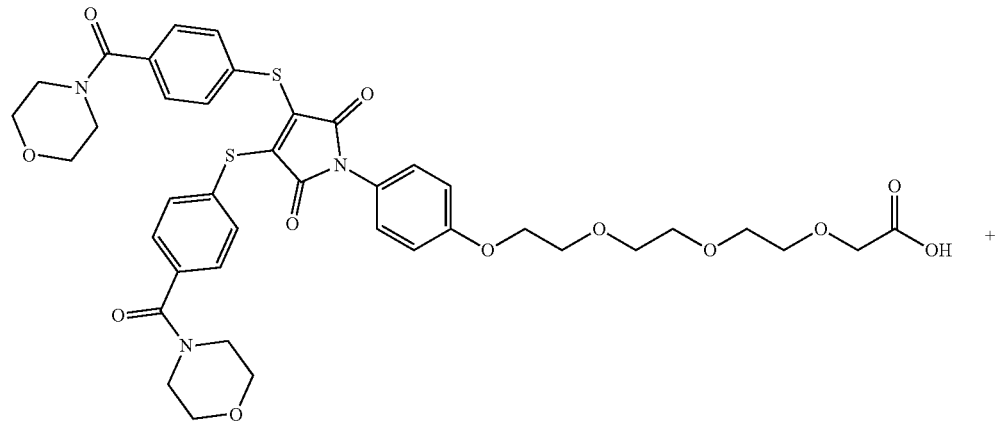

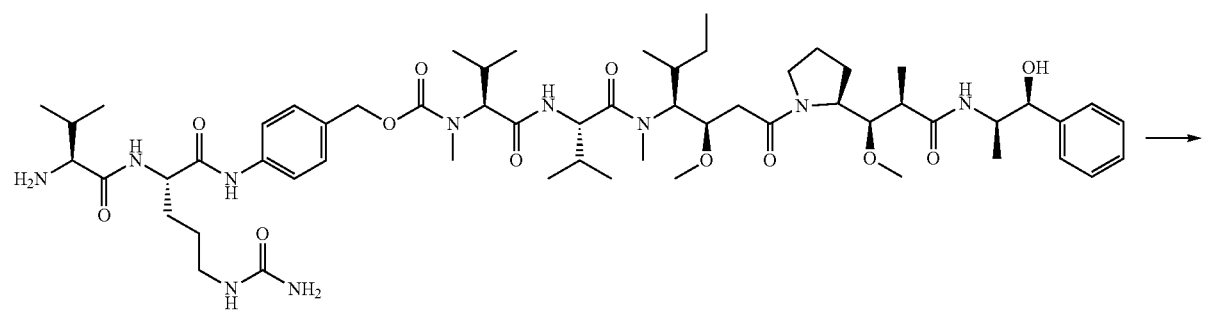

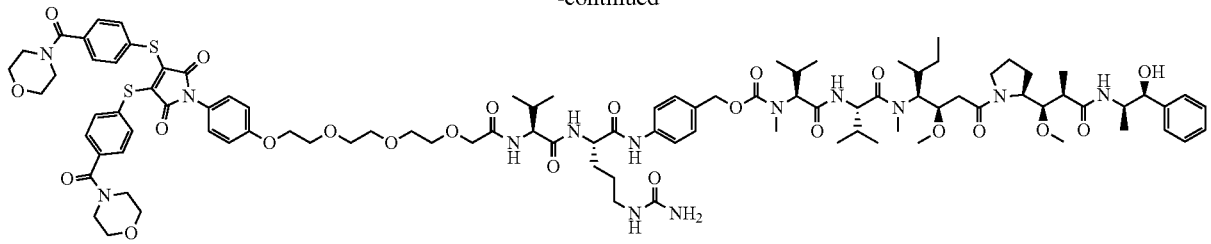

Compound E-9 (300 mg, 0.365 mmol) was weighed and placed into a 100 ml round-bottomed flask, anhydrous DMF (20 mL) was added under nitrogen protection and completely dissolved, and then HATU (166 mg, 0.438 mmol) and DIEA (0.127 ml, 0.730 mmol) were weighed and added successively into the flask. The obtained solution was stirred at room temperature for 15 minutes, then compound VC-PAB-MMAE (416 mg, 0.365 mmol) was added. The obtained solution was stirred at room temperature overnight under nitrogen protection. The reaction was monitored via TLC and HPLC overnight until the raw material F-1 disappeared. The solvent was evaporated off under reduced pressure. The residue was quantitatively analyzed and purified by reverse phase HPLC to obtain the product, as yellow amorphous powder. LC-MS (M$^r$) theoretical value: 1961.9, measured value: 1962.7 (ESI, M+H$^+$).

Preparation of CD73 Antibody-Drug Conjugate

The preparation scheme of the antibody-drug conjugate is shown below. The interchain disulfide bonds in antibody are reduced, resulting in 2n (such as 8) sulfhydryl groups. The substituted maleimide linker-drug conjugate (formula Ic) of the present invention is cross-linked with the reduced sulfhydryl group in antibody, thereby forming the corresponding antibody-drug conjugate, wherein the antibody-drug conjugate exists as one or two of the following forms.

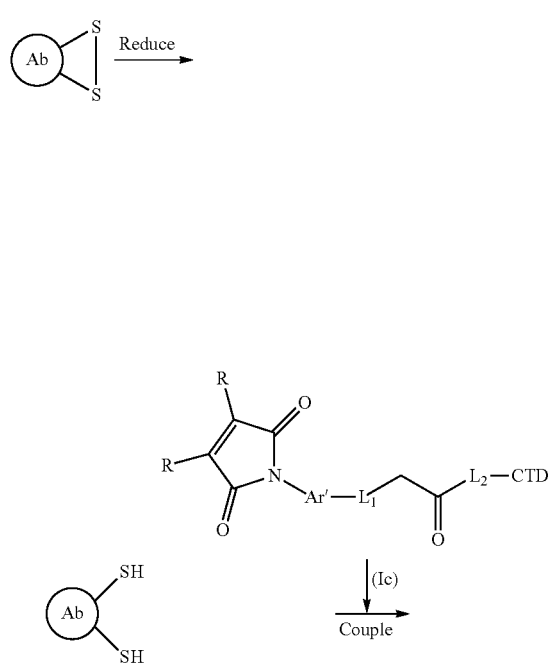

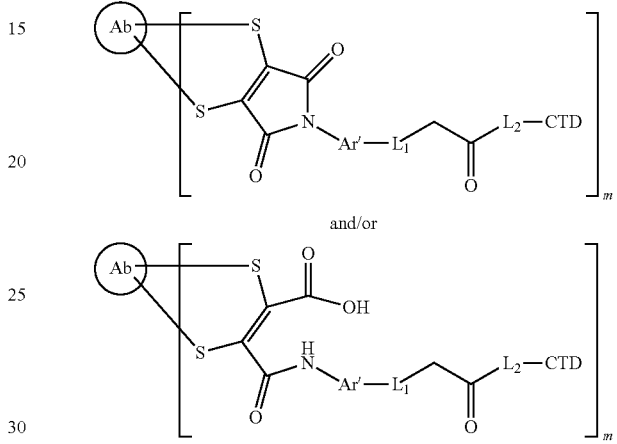

A typical preparation method comprises: diluting the antibody stock solution to 2-10 mg/mL with reaction buffer, adding excess dithiothreitol (DTT) of 140-200 fold molar ratio, or adding excess tris(2-carboxyethyl)phosphine hydrochloride (TCEP) of 6.0-20 fold molar ratio, and stirring the reaction solution at 10-35° C. for 2-48 hours. The reaction buffer herein can be a buffer prepared in the following proportion: 50 mM potassium dihydrogen phosphate-sodium hydroxide (KH$_2$PO$_4$—NaOH)/150 mM sodium chloride (NaCl)/1 mM diethylene triamine penlaacetic acid (DTPA), pH 6-9; 50 mM disodium hydrogen phosphate-citric acid/150 mM sodium chloride (NaCl)/1 mM diethylene triamine penlaacetic acid (DTPA), pH 6-9; 50 mM boric acid-borax/150 mM sodium chloride (NaCl)/1 mM diethylene triamine penlaacetic acid (DTPA), pH 6-9; 50 mM histidine-sodium hydroxide/150 mM sodium chloride (NaCl)/1 mM diethylene triamine penlaacetic acid (DTPA), pH 6-9 and PBS/1 mM diethylene triamine penlaacetic acid (DTPA), pH 6-9.

The above reaction solution is cooled to 0-10° C. If DTT reduction is used, it is necessary to pass through a desalting column or ultrafiltration to remove excess DTT after the reduction reaction is completed. Then the substituted maleimide compounds (10 mg/ml, previously dissolved in acetonitrile (ACN), dimethylsulfoxide (DMSO), dimethylformamide (DMF) or diethylacetamide (DMA)) is added. It should be ensured that the volume ratio of the organic solvent in the reaction solution is no more than 15%. The coupling reaction is performed at 0-37° C. with stirring for 2-4 hours. If TCEP reduction is used, it is unnecessary to remove the remaining TCEP and the substituted maleimide compounds can be directly added for coupling.

The coupling reaction mixture is filtrated and purified by using a desalting column with sodium succinate/NaCl buffer or histidine-acetic acid/sucrose gel, and the peak samples are collected according to UV280 absorption value. Alternatively, ultrafiltration is performed for several times. After filtration and sterilization, the resultant product is stored at low temperature. The preferred temperature is −100 to 60° C., and the pore size of the filter device is preferably 0.15-0.3 microns.

The drug/antibody coupling ratio (DAR) of the obtained antibody-drug conjugate is relatively uniform. When the maleimide linker (linker moiety) with different substitutions of the present invention is used, the uniformity of ADC product is very high (usually, the DAR advantage product (such as DAR is about 4) accounts for at least 60%, at least 70%, at least 80%, at least 90% or higher of all ADCs). For ADCs with certain differences in DAR, if a sample with better uniformity is needed, the following non-limitative methods can be further used for separation and purification: hydrophobic interaction chromatography (HIC), size-exclusion chromatography (SEC), ion exchange chromatography (IEC).

Use for Detection and Kit

The antibody or ADC thereof of the present invention can be used for detection, for example, for detecting samples, thereby providing diagnostic information.

In the present invention, the useful samples include cells, tissue samples and biopsy specimens. The term "biopsy" used in the present invention shall include all kinds of biopsy known to those skilled in the art. Therefore, the biopsy useful in the present invention may include, for example, excision samples of tumors, tissue samples prepared by endoscopic methods or organ puncture or needle biopsy.

The samples used in the present invention include fixed or preserved cell or tissue samples.

The present invention also provides a kit comprising the antibody (or fragment thereof) of the present invention. In a preferred embodiment of the present invention, the kit further comprises a container, an instruction for use, buffer, and the like. In a preferred embodiment, the antibody of the present invention can be immobilized on a detection plate.

Application

The present invention further provides use of the antibody of the present invention, for example, for preparation of a diagnostic agent, or for preparation of a medicine for preventing and/or treating a CD73-related disease. The CD73-related disease includes tumorigenesis, tumor growth and/or metastasis, a tumor resistance-related disease, inflammation, a metabolism-related disease, etc.

Use of the antibody, ADC or CAR-T according to the present invention includes but is not limited to:
  (i) diagnosis, prevention and/or treatment of tumorigenesis, tumor growth and/or metastasis, particularly, for a tumor with CD73 high expression; wherein the tumor includes (but is not limited to): breast cancer (e.g. triple negative breast cancer), lung cancer (such as non-small cell lung cancer), pancreatic cancer, malignant glioma, gastric cancer, liver cancer, esophageal cancer, kidney cancer, colorectal cancer, bladder cancer, prostate cancer, endometrial cancer, ovarian cancer, cervical cancer, leukemia, bone marrow cancer, angiosarcoma, etc.; preferably triple negative breast cancer, non-small cell lung cancer, pancreatic cancer, malignant glioma; and more preferably triple negative breast cancer and/or non-small cell lung cancer;
  (ii) diagnosis, prevention and/or treatment of an autoimmune disease; wherein the autoimmune disease includes (but are not limited to): systemic lupus erythematosus, rheumatoid arthritis, ulcerative colitis, type I diabetes, psoriasis, multiple sclerosis;
  (iii) diagnosis, prevention and/or treatment of inflammation; wherein the inflammation includes (but is not limited to): rheumatic arthritis, osteoarthritis, ankylosing spondylitis, gout, Lytle syndrome, psoriasis arthritis, infectious arthritis, tuberculous arthritis, viral arthritis, fungal arthritis, glomerular Nephritis, systemic lupus erythematosus, Crohn's disease, ulcerative colitis, acute lung injury, chronic obstructive pulmonary disease, and idiopathic pulmonary fibrosis;
  (iv) diagnosis, prevention and/or treatment of a metabolism-related disease, wherein the metabolism-related disease includes (but is not limited to): diabetes, diet-induced obesity, adipose inflammation.

Pharmaceutical Composition

The invention further provides a composition. In the preferred examples, the composition is a pharmaceutical composition comprising the antibody, or an active fragment, a fusion protein or an ADC thereof, or a corresponding CAR-T cell, and a pharmaceutically acceptable carrier. In general, these substances may be formulated in a non-toxic, inert and pharmaceutically acceptable aqueous carrier medium, wherein the pH is generally about 5-8, preferably, pH is about 6-8, although the pH value may be varied depending on the nature of the substances to be formulated and the condition to be treated. The formulated pharmaceutical composition may be administered by conventional routes, including (but not limited to): intratumoral, intraperitoneal, intravenous, or topical administration.

The antibody of the present invention can also be used for cell therapy by expressing the nucleotide sequence in a cell, for example, the antibody is used for chimeric antigen receptor T cell immunotherapy (CAR-T) and the like.

The pharmaceutical composition of the present invention can be directly used for binding to CD73 protein molecule, and thus can be used for preventing and treating diseases such as tumors. In addition, other therapeutic agents can also be used simultaneously.

The pharmaceutical composition according to the present invention comprises a safe and effective amount (e.g. 0.001-99 wt %, preferably 0.01-90 wt %, preferably 0.1-80 wt %) of the monoclonal antibody according to the present invention (or a conjugate thereof) and a pharmaceutically acceptable carrier or excipient. Such carriers include, but are not limited to, saline, buffer solution, glucose, water, glycerin, ethanol or the combination thereof. The pharmaceutical preparation should be matched to the method of administration. The pharmaceutical composition of the present invention can be prepared in the form of injection, for example, prepared by a conventional method using physiological saline or an aqueous solution containing glucose and other adjuvants. Pharmaceutical compositions such as injections and solutions are preferably prepared under sterile conditions. The dosage of active ingredient is therapeutically effective amount, for example from about 1 microgram per kilogram body weight to about 5 milligrams per kilogram body weight per day. Further, the polypeptide of the present invention can also be used in combination with the other therapeutic agents.

When a pharmaceutical composition is used, a safe and effective amount of the immunoconjugate is administered to a mammal, wherein the safe and effective amount is usually at least about 10 micrograms per kilogram of body weight, and in most cases does not exceed about 50 mg/kg body weight, preferably the dose is about 10 micrograms/kg body weight to about 20 mg/kg body weight. Of course, the particular dose should also depend on various factors, such as the route of administration, patient healthy status, which are well within the skills of an experienced physician.

As for the ADC, the antibody-drug conjugate provided by the present invention can target a specific cell population and bind to a specific protein (antigen) on cell surface, thereby releasing the drug into the cell in an active form through endocytosis or drug infiltration of the conjugate. Thus, the antibody-drug conjugate of the invention can be used to treat diseases of interest, and the antibody-drug conjugate mentioned above can be administered to a subject (e.g., a human) by a suitable route in a therapeutically effective amount. A subject in need of treatment can be a patient at risk of having or suspected of having a condition associated with the activity or amount of expression of a particular antigen. Such patients can be identified by routine physical examination.

When the antibody drug conjugate as described herein is used as the therapeutic agent, it can be delivered by methods conventional in the art. For example, it can be introduced into cells using liposomes, hydrogels, cyclodextrins, biodegradable nanocapsules, or bioadhesive microspheres. Alternatively, nucleic acids or vectors can be delivered in situ by direct injection or by use of an infusion pump.

The Main Advantages of the Present Invention Include:

(A) The antibody of the present invention has excellent biological activity and specificity, and has a high affinity (the $EC_{50}$ determined by ELISA is 0.016-0.038 nM), and has inhibitory activity on CD73 enzyme function (the $IC_{50}$ determined by enzymatic activity is 0.025-0.039 nM). In addition, the antibody has a good binding affinity for CD73 of tumor cells (the $EC_{50}$ determined by FACS is 0.35-2.5 nM), inhibits the function of tumor CD73 enzyme ($IC_{50}$ value is 0.2 nM-0.6 nM), and can be used as a therapeutic antibody targeting CD73.

(b) The humanized antibody of the present invention has not only activity comparable to that of murine antibody, but also lower immunogenicity.

(c) Both the antibody and ADC of the present invention have significant anti-tumor activity in vivo, but have no visible toxic and side effects on mammals such as model mice.

(d) The antibody of the present invention has a significant protective effect on proliferation of human lymphocytes, can effectively reverse the inhibition of adenosine monophosphate (AMP) on the proliferation of T lymphocytes and promote the expression and secretion of INF-γ, wherein $EC_{50}$ is 0.01-0.08 nM.

(e) The antibody-drug conjugate (ADC) of the present invention has excellent CD73-dependent anti-tumor activity. That is, it has no obvious toxic and side effects on cells with normal or low expression of CD73, but has extremely high killing activity on tumor cells with high expression of CD73, and $IC_{50}$ determined by cell proliferation inhibition test is 0.02 nM-0.05 nM.

(f) The antibody-drug conjugate (ADC) of the present invention has no obvious toxic and side effects on the proliferation of normal human T lymphocytes, and $IC_{50}$ determined by cell proliferation inhibition test is >100 nM.

(g) The antibody-drug conjugate (ADC) of the present invention does not exhibit high or unexpected toxic and side effects on mammals such as cynomolgus monkey, and has potential prospects for clinical drug application.

(h) The novel linker provided by the present invention can couple with a CD73-targeting antibody through a simple chemical method, and the DAR distribution of the CD73 antibody-drug conjugate obtained by using the linker is very narrow as compared with conventional coupling way. Therefore, the resulting product has high homogeneity. The obtained cross-linked product has a single distribution (with a DAR of 4) which accounts for more than 80%. Compared with traditional cVC-PAB cross-linked product, the cross-linked product has improved or comparable inhibitory activity on tumor cell proliferation in vitro, the biological activity, safety and other proprietary properties.

(i) The disulfide bond linkage based on maleimide of the present invention has better stability. The introduction of substituent at Ar' position can adjust the reaction rate of maleimide ring opening hydrolysis and slow down the secondary hydrolysis of cyclization of ring opened maleimide, and sulfhydryl exchange and secondary hydrolysis of cyclization after ring opening are less likely to occur, which further strengthens the stability of the CD73 antibody-drug conjugate in vitro and in vivo.

The present invention will be further illustrated below with reference to the specific examples. It is to be understood that these examples are for illustrative purposes only and are not intended to limit the scope of the invention. For the experimental methods in the following examples, in which the specific conditions are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified. Unless indicated otherwise, parts and percentage are weight parts and weight percentage. The cell strain is a conventional commercially available product or purchased from ATCC, and the plasmids are all commercially available products.

Example 1 Discovery and Preparation of Monoclonal Antibodies Targeting Human CD73

Steps (1), Preparation of Hybridoma Cells:

First, the extracellular domain of human CD73 protein (CD73-ECD) was prepared as an antigen. By referring to NCBI: NP 002517.1 amino acid at positions 27 to 547, C-terminus polyhistidine-tagged antigen was obtained using gene cloning technology and mammalian vector expression system, the specific amino acid sequence was as follows (SEQ ID NO. 48):

WELTILHTNDVHSRLEQTSEDSSKCVNASRCMGGVARLFTKVQQIRRAEP

NVLLLDAGDQYQGTIWFTVYKGAEVAHFMNALRYDAMALGNHEFDNGVEG

LIEPLLKEAKFPILSANIKAKGPLASQISGLYLPYKVLPVGDEVVGIVGY

TSKETPFLSNPGTNLVFEDEITALQPEVDKLKTLNVNKIIALGHSGFEMD

KLIAQKVRGVDVVVGGHSNTFLYTGNPPSKEVPAGKYPFIVTSDDGRKVP

VVQAYAFGKYLGYLKIEFDERGNVISSHGNPILLNSSIPEDPSIKADINK

WRIKLDNYSTQELGKTIVYLDGSSQSCRFRECNMGNLICDAMINNNLRHT

DEMFWNHVSMCILNGGGIRSPIDERNNGTITWENLAAVLPFGGTFDLVQL

KGSTLKKAFEHSVHRYGQSTGEFLQVGGIHVVYDLSRKPGDRVVKLDVLC

TKCRVPSYDPLKMDEVYKVILPNFLANGGDGFQMIKDELLRHDSGDQDIN

VVSTYISKMKVIYPAVEGRIKAHHHHHHHHHH

Balb/c mice were immunized with the above-prepared CD73 extracellular domain protein, and the CD73 extracellular domain protein was used in an amount of 50 m/mouse to prepare immunized splenocytes. Murine myeloma cells (SP2/0) and feeder cells were prepared at an appropriate time for fusion.

After the above three kinds of cells were prepared, the fusion of splenocytes with SP2/0 cells was mediated by PEG. PEG was then removed, and the resultant cells were re-suspended in HAT complete medium containing feeder cells, and were seeded and cultured in a 96-well plate. Positive wells were screened by ELISA/FACS. Finally, the cells in the positive wells were subjected to clonal culture by using limited dilution method, and the cells, which had a high titer, were in a good morphology and grew in a monoclonal manner, were screened by ELISA or FASCS. The cells were further subjected to subcloning screening until the positive cloning rate was 100% for three consecutive screening. Then, the cell line was subjected to amplification and library construction.

Step (2), Purification of Murine Monoclonal Antibody Targeting Human CD73:

The hybridoma cells selected in step (1) were expanded and cultured in a roller bottle for 14 days, then the cell culture supernatant was collected and filtered through a 0.22 μm filter membrane. Subsequently, the obtained culture supernatant was added to the pre-balanced Protein A resin column at a constant rate, and the column was equilibrated with 0.1M Tris-HCl (pH=8.0, containing 1.5M NaCl). Then the balance column was eluted with 0.1M sodium citrate buffer, and the eluate was collected and quantified, and subjected to SDS-PAGE electrophoresis, SEC-HPLC and endotoxin detection. The purified antibodies obtained were subpackaged and stored at −80° C. for later use.

Steps (3), Detection of Biological Activity and Specificity of the Murine Monoclonal Antibody Targeting Human CD73:

After repeated screening, the biological activity and target specificity of the selected 5 hybridoma monoclonal antibodies were determined. As shown in FIG. 1A, the culture supernatant of the monoclonal cell was detected by a Fluorescence Activated Cell Sorter (FACS). All 5 antibodies could specifically bind to human MDA-MB-231 cells with CD73 high expression (CD73-P), but had no obvious binding activity to MDA-MB-453 cells with CD73 low expression (CD73-N). Subsequently, the purified antibody sample was used for serial dilution and FACS detection. As shown in FIG. 1B, mAb001, mAb002, mAb003, mAb004, and mAb005 had excellent binding affinity to MDA-MB-231 cells. Their $EC_{50}$ detected by FACS were 1.24 nM, 0.65 nM, 10.7 nM, 4.69 nM, and 26.07 nM, respectively.

Example 2 Antibody Sequencing and Identification of Complementarity Determining Region (CDR)

Based on their excellent specificity and affinity, mAb001, mAb002, and mAb004 were preferentially selected for antibody sequencing and identification. Primers were designed to amplify heavy chain (VH) and light chain (VL) variable region fragments by conventional PCR technology (see FIG. 2). The fragments were cloned into vector and sequenced. Using routine sequencing and Kabat database analysis, the following amino acid sequences of heavy chain variable region (VH) and light chain variable region (VL), and the information of complementarity determining region (CDR) were obtained (The amino acid sequence of CDR-1/2/3 were shown by underline).

amino acid sequence of heavy chain variable region (VH) of mAb001
SEQ ID NO. 7
QVQLQQSGPELVKPGASVRISCKTSGYTFT<u>NYYIY</u>WVKQRPGQGLEWIGW<u>IYPGNLNI</u>KYNEKFKGKSTLTADKSSSTAFMQLSSLTSEDSAVYFCAR<u>DDNYAWFAY</u>WGQGTLVTVSS amino acid sequence of heavy chain variable region (VH) of mAb002
SEQ ID NO. 16
QVQLQQPGAELVKPGASVRLSCKASGYTLT<u>SYWMH</u>WVKKRPGQGLEWIGE<u>INPSNGRSN</u>YNEKFKSKATLTVDRSSSTVYMQLGSLTSEDSAVYYCAR<u>RGVSGNYFDY</u>WGQGTTLTVSS amino acid sequence of heavy chain variable region (VH) of mAb004
SEQ ID NO. 27
EVQLQQSGPELVKPGASVKIPCKASGYTFT<u>DYNMD</u>WVKQSHGKSLEWIGD<u>INPNNGGS</u>VYNQKFKGKATLTVDKSSSTAYMELRSLTSEDTAVYYCGR<u>ITGTGYWSFDV</u>WGTGTTVTVSP amino acid sequence of light chain variable region (VL) of mAb001
SEQ ID NO. 8
DIVMTQSHKFMSTSIGDRVSITC<u>KASQDVSTAVA</u>WYQQKPGQSPKLLIYW<u>TNTRHT</u>GVPDRFTGNTSGTEHTLTISSVQAEDLALYYC<u>QQHYSTPFT</u>FGSGTTLEIK amino acid sequence of light chain variable region (VL) of mAb002
SEQ ID NO. 19
DIKMTQSPSSMYASLGERVTMTC<u>KASQDINTYLS</u>WFQQKPGKSPKTLIYR<u>SNILVDG</u>VPSRFSGSRSGQDYYLTITSLEYEDMGIYYC<u>LQYDEFPYT</u>FGGGTKLELK amino acid sequence of light chain variable region (VL) of mAb004
SEQ ID NO. 30
DIQMTQSPASLSVSVGETVTITC<u>RASENIYSNLA</u>WYQQKQGKSPQLLVYG<u>ATNLAEG</u>VPSRFSGSGLGTQYSLKISSLQSEDFGSYYC<u>QHFWGIPWT</u>FGGGTKLEIK Example 3 Preparation of Human-Mouse Chimeric Antibody and Point Mutation of Chimeric Antibody Using gene recombination technology, 3 sets of variable region sequences (see SEQ ID NO. 7, SEQ ID NO. 16, SEQ ID NO. 27, SEQ ID NO. 8, SEQ ID NO. 19, and SEQ ID NO. 30) were cloned into a vector containing recombinant heave chain constant region and Kappa chain constant region of human IgG1. The vector was confirmed to be correct by sequencing, and then the constructed chimeric antibodies were expressed and purified using transfection technology and mammalian expression system (FreeStyle™ 293T cells) (see FIG. 3). The obtained human-mouse chimeric antibodies were numbered mAb001c, mAb002c, and mAb004c.

The variable region sequences of the antibody contain several unfavorable amino acids, which were modified by point mutations. The amino acid sequences of the heavy chain variable region (VH) and light chain variable region (VL) after point mutations are as follows (The amino acid sequences of CDRs are shown by underline).

mAb001-VL-SGS
SEQ ID NO. 9
DIVMTQSHKFMSTSIGDRVSITC<u>KASQDVSTAVAWYQQKPGQSPKLLIYW</u>
<u>TNTRHT</u>GVPDRFTGSGSGTEHTLTISSVQAEDLALYYC<u>QQHYSTPFT</u>FGS
GTTLEIK mAb002-VH-QG
SEQ ID NO. 17
QVQLQQPGAELVKPGASVRLSCKASGYTLT<u>SYWMH</u>WVKKRPGQGLEWIGE
<u>INPSQGRSNYNEKFKS</u>KATLTVDRSSSTVYMQLGSLTSEDSAVYYCAR<u>RG</u>
<u>VSGNYFDY</u>WGQGTTLTVSS mAb002-VH-NA
SEQ ID NO. 18
QVQLQQPGAELVKPGASVRLSCKASGYTLT<u>SYWMH</u>WVKKRPGQGLEWIGE
<u>INPSNARSNYNEKFKS</u>KATLTVDRSSSTVYMQLGSLTSEDSAVYYCAR<u>RG</u>
<u>VSGNYFDY</u>WGQGTTLTVSS mAb002-VL-SG
SEQ ID NO. 20
DIKMTQSPSSMYASLGERVTMTC<u>KASQDINTYLSWFQQKPGKSPKTLIYR</u>
<u>SNILVS</u>GVPSRFSGSRSGQDYYLTITSLEYEDMGIYYC<u>LQYDEFPYT</u>FGG
GTKLELK mAb004-VH-QG
SEQ ID NO. 28
EVQLQQSGPELVKPGASVKIPCKASGYTFT<u>DYNMD</u>WVKQSHGKSLEWIGD
<u>INPNQGGSVYNQKFKG</u>KATLTVDKSSSTAYMELRSLTSEDTAVYYCGR<u>IT</u>
<u>GTGYWSFDV</u>WGTGTTVTVSP mAb004-VH-NA
SEQ ID NO. 29
EVQLQQSGPELVKPGASVKIPCKASGYTFT<u>DYNMD</u>WVKQSHGKSLEWIGD
<u>INPNNAGSVYNQKFKG</u>KATLTVDKSSSTAYMELRSLTSEDTAVYYCGR<u>IT</u>
<u>GTGYWSFDV</u>WGTGTTVTVSP

The point mutation (PTM) was obtained by matching the above-mentioned point mutation template, and then cloned into the hIgG1 vector to obtain the corresponding chimeric antibody mutant with the point mutation.

The numbers of the human-mouse chimeric antibodies and the antibody mutants mentioned above, and the numbers of the heavy and light chains of the antibodies are summarized in Table-1.

TABLE 1

Human-mouse chimeric antibodies and the mutants thereof

| Antibody name | VH SEQ ID NO: | VL SEQ ID NO: |
|---|---|---|
| mAb001c | 7 | 8 |
| mAb001c-VK-SGS | 7 | 9 |
| mAb002c | 16 | 19 |
| mAb002c-VH-QG | 17 | 19 |
| mAb002c-VH-NA | 18 | 19 |
| mAb002c-VK-SG | 16 | 20 |
| mAb002c-VH-QG, VK-SG | 17 | 20 |
| mAb004c | 27 | 30 |
| mAb004c-VH-QG | 28 | 30 |
| mAb004c-VH-NA | 29 | 30 |

Example 4 ELISA Determination of the Affinity of Chimeric Antibodies to Human CD73 Antigen The extracellular domain of CD73 protein (CD73-ECD) was diluted to 1 μg/mL with the coating solution, and coated onto ELISA plate with 100 μL/well at 4° C. overnight. The excess antigen was washed off. The plate was blocked with 1% BSA at room temperature for 2 h, then each monoclonal antibody in a 3-fold dilution was added at 100 μL/well. The plate was incubated at room temperature for 1 h; the unbound antibody was washed off, and appropriate concentration of anti-mouse secondary antibody labeled with horseradish peroxidase was added at 100 μL/well. The plate was incubated at room temperature for 0.5 h. The unbound secondary antibody was washed off. TMB substrate was added and reacted for about 15 minutes. 1N HCl was added at 50 μL/well to stop the color reaction. Then the absorbance was measured at 450 nm and the obtained data was analyzed.

Figure 4:
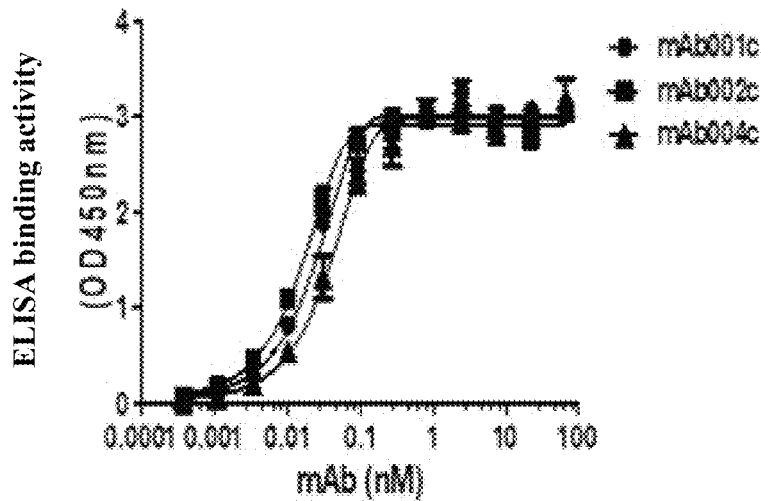
FIG. 4 shows the binding affinity ($EC_{50}$) of human-mouse chimeric antibodies mAb001c, mAb002c, and mAb004c to CD73-ECD detected by ELISA.

The detection results are shown in FIG. 4. mAb001c, mAb002c, and mAb004c had strong affinity to CD73-ECD, and $EC_{50}$ was 0.024 nM, 0.016 nM, and 0.038 nM, respectively.

Figure 13:
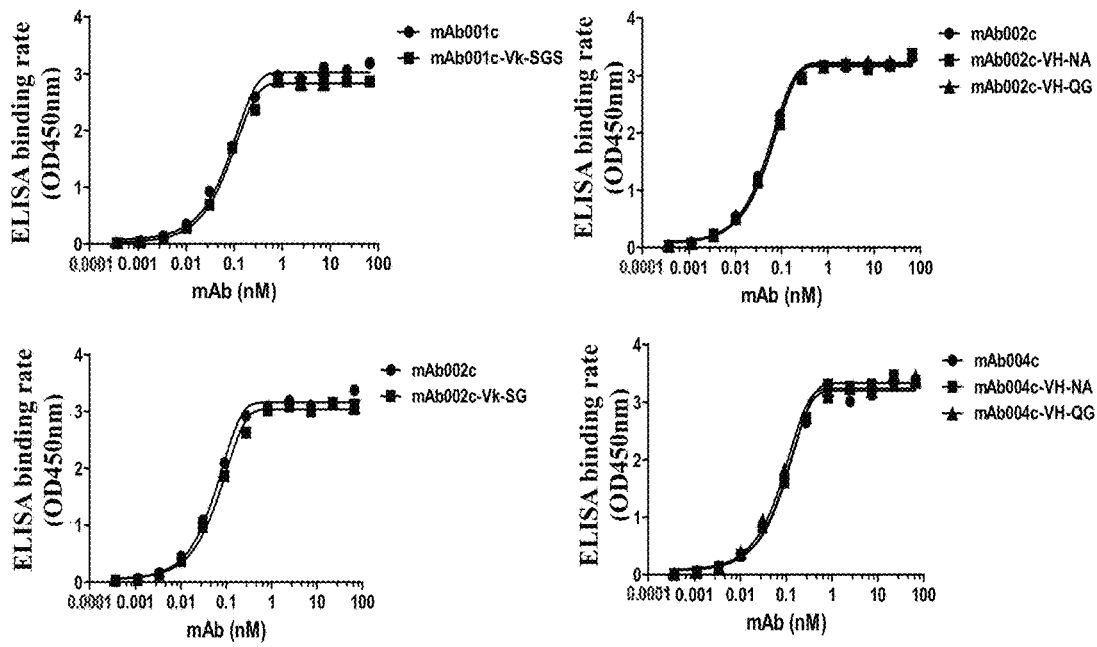
FIG. 13 shows the binding affinity ($EC_{50}$) of a series of mAb001c-point mutants, mAb002c-point mutants, and mAb004c-point mutants to CD73-ECD as detected by ELISA.

The detection results are shown in FIG. 13. The $EC_{50}$ values detected by ELISA of the mAb001c/mAb002c/mAb004c mutants were 0.05 nM-0.093 nM.

Example 5 Determination of the Inhibitory Activity of the Chimeric Antibodies on the Catalytic Function of Recombinant Human CD73

The human recombinant CD73 enzyme (CD73 extracellular domain) was diluted to 0.1 μg/mL with antigen diluent, and spread evenly on a 96-well low-adsorption culture plate at 25 μL/well. 50 μL of CD73 antibody diluted in a 3-fold gradient from 2 nM to 0.0009 nM was added to the culture plate, and the mixture was mixed well (final concentrations were 1 nM-0.00045 nM). The culture plate was incubated at 37° C. for 1 h, and then 25 μL of mixed solution containing 1.2 mM AMP and 0.4 mM ATP was added, and the culture plate was incubated at 37° C. for 1 h. 50 μL of the above reaction solution was added to another 96-well blank plate, 50 μL of CellTiter-Glo reagent was added to each well, and the mixture was mix well and reacted for 3-5 min in the dark. The fluorescence signal intensity was detected with a microplate reader.

Figure 5:
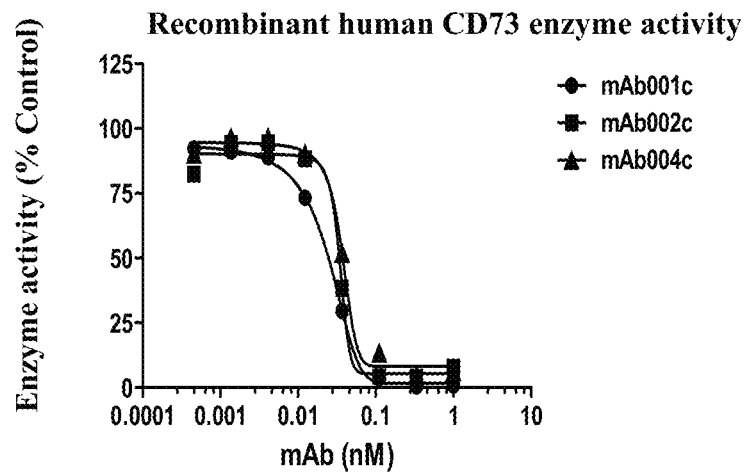
FIG. 5 shows the inhibitory activity ($IC_{50}$) of mAb001c, mAb002c, and mAb004c on the catalytic function of recombinant human CD73.

The detection results are shown in FIG. 5. All of mAb001c, mAb002c, and mAb004c had significant inhibitory activity on the hydrolysis of AMP by recombinant CD73 protease, and $IC_{50}$ were 0.025 nM, 0.031 nM, and 0.039 nM, respectively.

Figure 16:
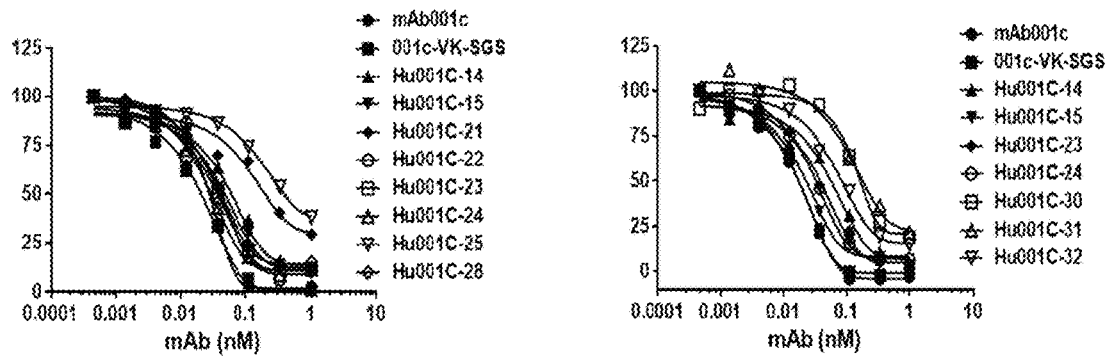
FIG. 16 shows the detected inhibitory activity ($IC_{50}$) of a series of mAb001c humanized antibodies (Hu001c-14 to 15, Hu001c-21 to 28, and Hu001c-30 to 32) on the catalytic function of recombinant human CD73.

The detection results are shown in FIG. 16. The $IC_{50}$ of mAb001c-Vk-SGS was 0.02 nM.

Figure 17:
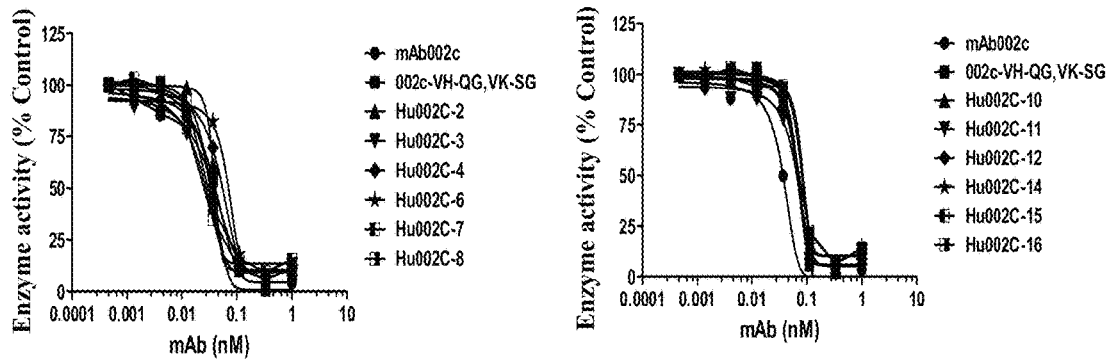
FIG. 17 shows the detected inhibitory activity ($IC_{50}$) of a series of mAb002c humanized antibodies (Hu002c-2 to 16) on the catalytic function of recombinant human CD73.

The detection results are shown in FIG. 17. The $IC_{50}$ of mAb002c-VH-QG/VK-SG were 0.038 nM and 0.06 nM.

Example 6 Specific Binding of Chimeric Antibodies to CD73 on the Surface of Tumor Cells CD73-high-expression triple negative breast cancer cells MDA-MB-231, non-small cell lung cancer cells NCI-H1299, Calu-1, glioma cells U87MG and pancreatic cancer cells SW1990, and CD73-low-expression breast cancer cells MDA-MB-453 and non-small cell lung cancer cell NCI-H460 were used to detect the binding of chimeric antibody to CD73 on the cell surface. $3\times10^5$ tumor cells were mixed well with the antibody (final concentration was 5 μg/mL), and then incubated at 4° C. for 1 h. The cells were washed twice with PBS to remove the unbound primary antibody. Then the target cells were incubated with PE-labeled secondary antibody at 4° C. for 30 minutes. The cells were washed twice with PBS to remove the unbound secondary antibody. Finally, the cells were resuspended in 200 μL PBS and the binding rate was detected with a Fluorescence Activated Cell Sorter (FACS).

Figure 6:
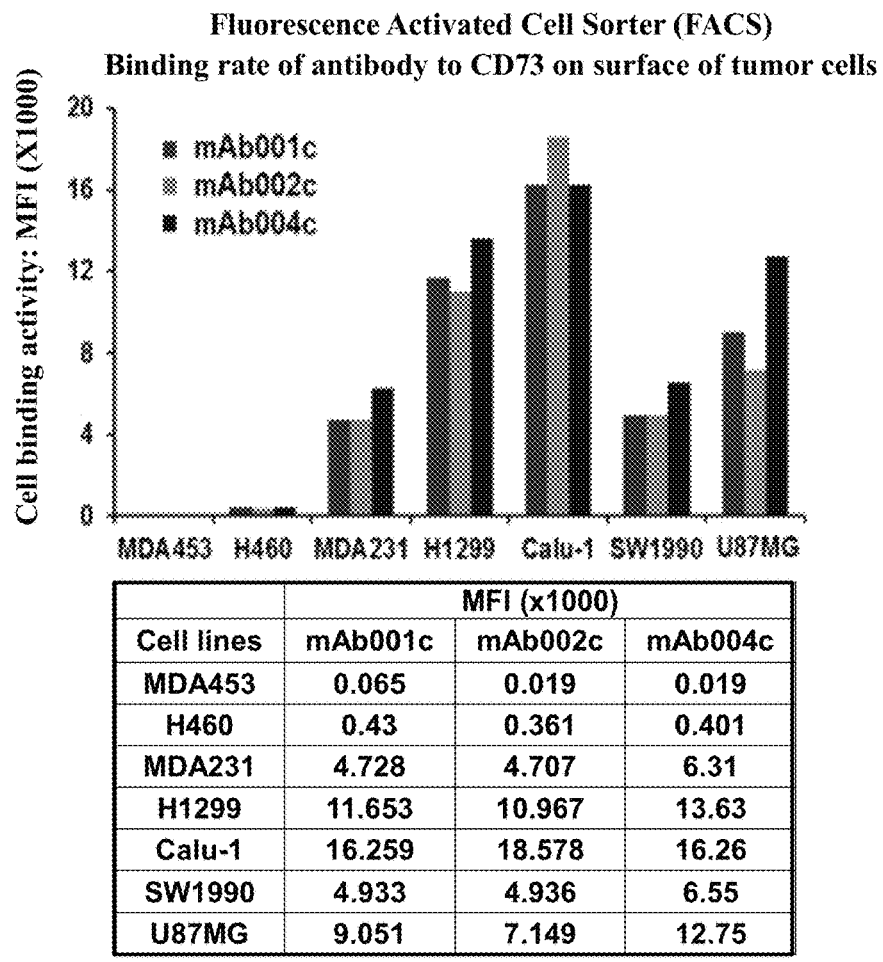
FIG. 6 shows the binding rate (MFI) of mAb001c, mAb002c, and mAb004c to CD73 receptors on the surface of breast cancer MDA-MB-453, MDA-MB-231, lung cancer NCI-H460, NCI-H1299, Calu-6, pancreatic cancer SW1990, and glioma U87MG cells, detected by Fluorescence Activated Cell Sorter (FACS). $3 \times 10^5$ cells were mixed with 5 µg/mL antibody in this experiment, and detected after incubation for 1 hour.

The detection results are shown in FIG. 6. The chimeric antibody could specifically recognize and bind tumor cells with CD73 high expression. The order of fluorescence intensity of binding rate were Calu-1, NCI-H1299, U87MG, SW1990, MDA-MB-231, and CD73 low expression tumor cells MDA-MB-453 and NCI-H460 showed very weak binding fluorescence intensity. Comparing the binding rate (MFI) of Calu-1 and MDA-MB-453 to the antibody, the difference in binding rate for mAb001c was 250 times, for mAb002c was 978 times, and for mAb004c was 856 times.

Example 7 CD73 Protein Level on the Surface of Tumor Cells was Closely Related to its Enzyme Activity CD73-high-expression (U87MG, Calu-1, NCI-H1299) and CD73-low-expression (MDA-MB-453) cell lines were used to study the correlation between the amount of CD73 protein on the cell surface and enzyme activity. Firstly, 100 μL of solution containing each cell line mentioned above wherein the number of cells was diluted from 20,000 to 625 by a double gradient, was spread evenly on a 96-well cell culture plate. After culturing at 37° C. for 16 hours, the plate was washed 3 times with serum-free medium to remove residual serum. 50 μL of 300 μM AMP was slowly added, mixed well, and incubated at 37° C. for 3 h. 250_, of culture medium supernatant was carefully taken out and placed in another 96-well blank plate. 250_, of 100 μM ATP was added and mixed well. 50 μL of CellTiter-Glo reagent was added to each well, mixed well and reacted for 3 to 5 minutes in the dark. The intensity of the fluorescence signal was detected with a microplate reader.

Figure 7:
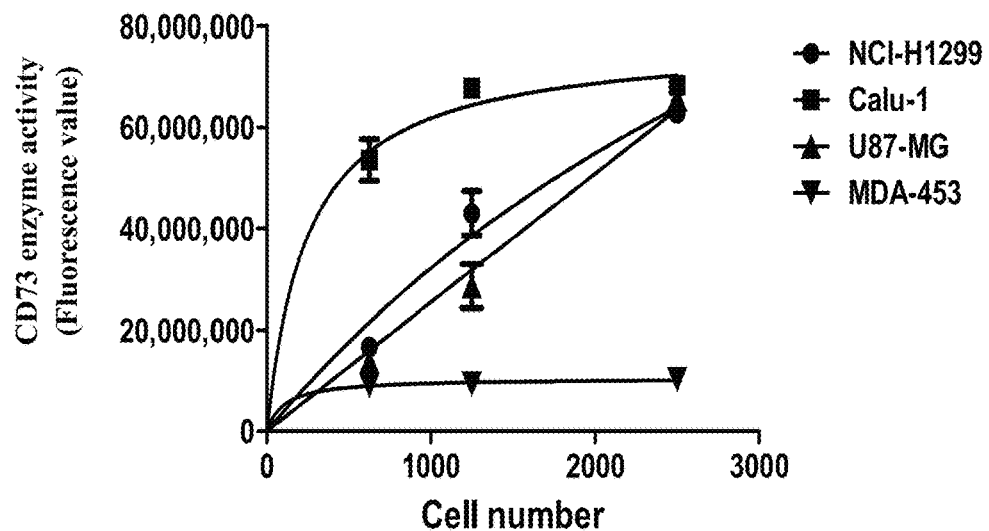
FIG. 7 shows that CD73 protein level on the surface of tumor cells is closely related to its enzyme activity. CD73-high expression cell lines (U87MG, Calu-1, and NCI-H1299) and CD73-low expression cell line (MDA-MB-453) were indicated with adenosine monophosphate (AMP) in a cell number as shown for 3 hours, then the enzyme activity was determined.

The results are shown in FIG. 7. Within the linear range of the test, CD73-low-expression MDA-MB-453 cells produced only a very low levels (background level) of enzyme activity, while the three CD73-high-expression cells all showed high enzyme activity, thus confirming that the level of CD73 protein on the surface of tumor cells was closely related to its enzymatic activity.

Example 8 Determination of the Binding Affinity of Chimeric Antibodies to CD73 on Surface of Tumor Cells CD73-high-expression triple negative breast cancer cells MDA-MB-231 and non-small cell lung cancer cells NCI-H1299 were used as target cells. 100 μL of the test antibody diluted in a 3-fold gradient from 200 nM to 0.091 nM was used as primary antibody, and mixed with 1×10⁵ MDA-MB-231 suspended in 100 μL RPMI-1640 serum-free medium, respectively. Alternatively, 100 μL of mAb001c, mAb002c, mAb004c diluted in a 3-fold gradient from 100 nM to 0.046 nM were used as primary antibodies and mixed with 1×10⁵ NCI-H1299 cells suspended in 100 μL RPMI-1640 serum-free medium. Then the obtained solutions were incubated at 4° C. for 1 h, the cells were washed twice with PBS to remove unbound primary antibody, and the target cells were incubated with 200 μL PE-labeled secondary antibody (2 μg/mL) at 4° C. for 30 min. The cells were washed twice with PBS to remove unbound secondary antibody. Finally, the cells were resuspended in 200 μL PBS, and the binding affinities of the test antibodies to CD73 on the cell surface were determined by a flow cytometer.

Figure 8:
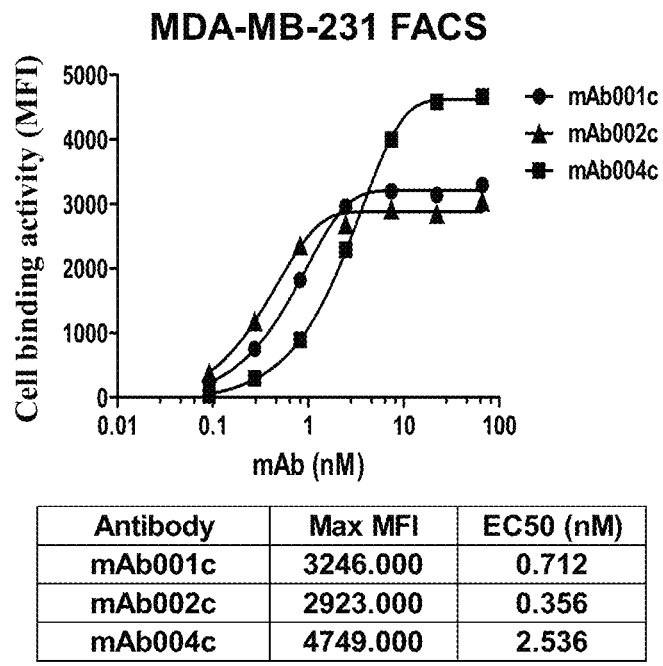
FIG. 8 shows the detected binding affinity ($EC_{50}$) of mAb001c, mAb002c, and mAb004c to CD73 on the surface of MDA-MB-231 cells. In this experiment, $1 \times 10^5$ cells were mixed with the antibody of a concentration gradient as shown, and detected after incubation for 1 hour.

The detection results are shown in FIG. 8. mAb001c, mAb002c, and mAb004c had excellent binding affinity to MDA-MB-231, and $EC_{50}$ were 0.7 nM, 0.36 nM, and 2.5 nM, respectively.

Figure 9:
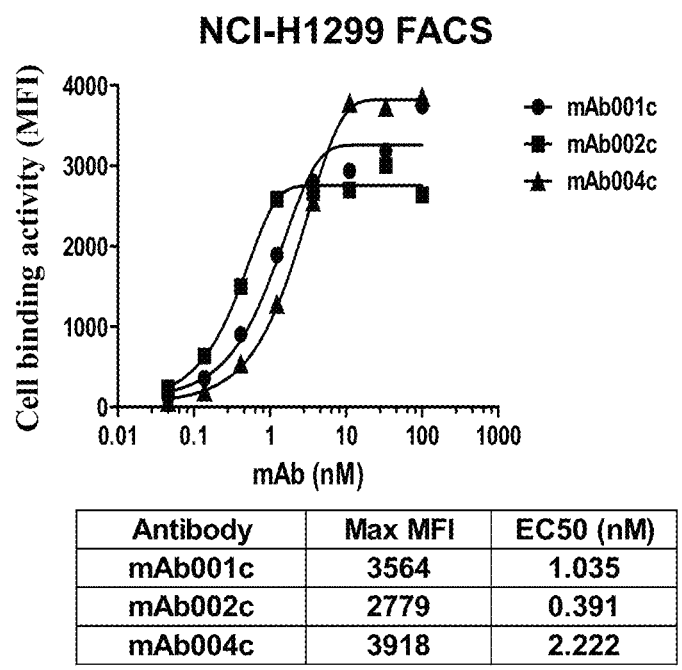
FIG. 9 shows the detected binding affinity ($EC_{50}$) of mAb001c, mAb002c, and mAb004c to CD73 on the surface of NCI-H1299 cells. In this experiment, $1 \times 10^5$ cells were mixed with the antibody of a concentration gradient as shown, and detected after incubation for 1 hour.

The detection results are shown in FIG. 9. mAb001c, mAb002c, and mAb004c also had excellent binding affinity to NCI-H1299, and $EC_{50}$ were 1.0 nM, 0.39 nM, and 2.2 nM, respectively.

Figure 18:
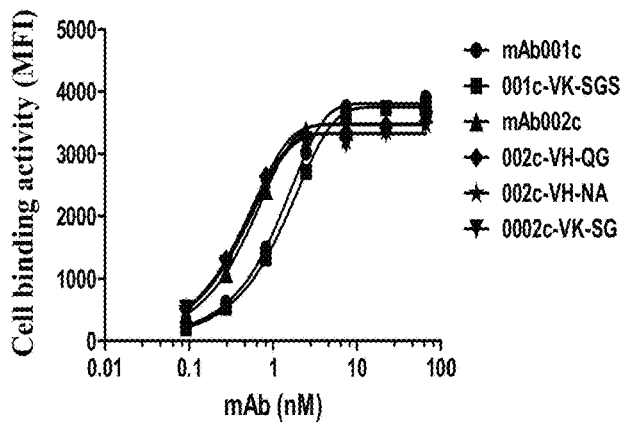
FIG. 18 shows the binding affinity ($EC_{50}$) of a series of mAb001c mutants and a series of mAb002c mutants to CD73 on the surface of MDA-MB-231 cells as detected by FACS. In this experiment, $1 \times 10^5$ cells were mixed with the antibody of a concentration gradient as shown, and detected after incubation for 1 hour.

The detection results are shown in FIG. 18. The derivative mutants of mAb001c/mAb002c also had excellent binding affinity to MDA-MB-231, and the $EC_{50}$ value of mAb001c-VK-SGS was 1.39 nM; the $EC_{50}$ value of mAb002c-VH-QG/NA was 0.43 nM; the $EC_{50}$ value of mAb002c-VK-SG was 0.46 nM.

In summary, the above results indicated that the monoclonal antibodies of the present example could target CD73 of human tumor cells.

Example 9 Effect of Chimeric Antibodies on the Catalytic Function of CD73 Enzyme on the Surface of Tumor Cells The CD73-high-expression triple negative breast cancer cells MDA-MB-231, non-small cell lung cancer cells NCI-H1299 and Calu-1 were used as target cells. An appropriate number of tumor cells (confirmed by pre-experiment) were spread on a 96-well plate. After culturing at 37° C. for 16 hours, the cells were washed 3 times with serum-free RPMI-1640 medium, and 50 μL of the test antibody diluted in a 3-fold gradient from 200 nM to 0.091 nM was added to a 96-well plate. After incubating at 37° C. for 30 min, 25 μL of 0.9 mM AMP was added and incubated at 37° C. with 5% $CO_2$ for 3 h (the final antibody concentrations were 133.3 nM-0.06 nM). 25 μL of the above culture supernatant was taken out and added to another 96-well blank plate, 25 μL of 0.1 mM ATP was added and mixed well. 50 μL of CellTiter-Glo reagent was added to each well, mixed well and reacted for 3 to 5 minutes in the dark. The intensity of the fluorescence signal was detected with a microplate reader.

Figure 10:
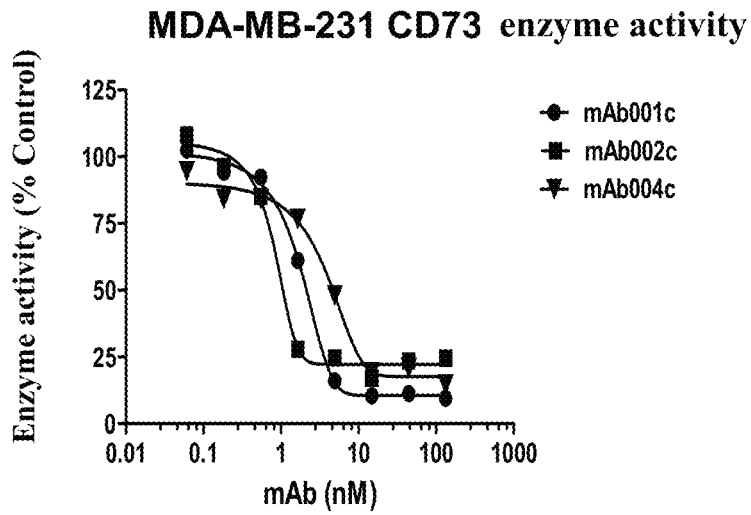
FIG. 10 shows the detected inhibitory activity ($IC_{50}$) of mAb001c, mAb002c, and mAb004c on the catalytic function of CD73 on the surface of MDA-MB-231 cells.

The detection results are shown in FIG. 10. mAb001c, mAb002c, and mAb004c could significantly inhibit the function of CD73 on the surface of MDA-MB-231 cells to catalyze the hydrolysis of AMP. $IC_{50}$ values were 1.858 nM, 0.791 nM, and 4.164 nM, respectively.

Figure 11:
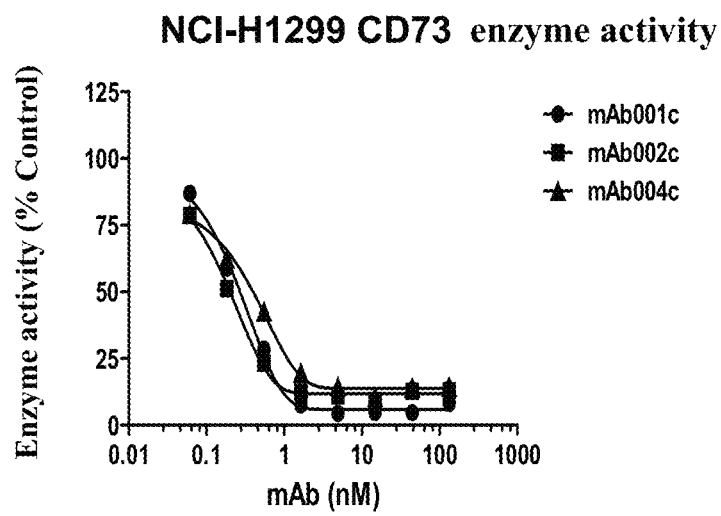
FIG. 11 shows the detected inhibitory activity ($IC_{50}$) of mAb001c, mAb002c, and mAb004c on the catalytic function of CD73 on the surface of NCI-H1299 cells.

The detection results are shown in FIG. 11. mAb001c, mAb002c, and mAb004c could inhibit the function of CD73 on the surface of NCI-H1299 cells to catalyze the hydrolysis of AMP. $IC_{50}$ value were 0.236 nM, 0.191 nM, and 0.385 nM, respectively.

Figure 12:
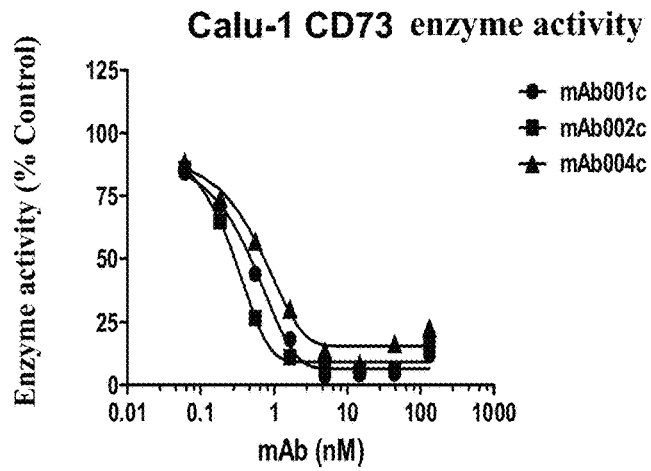
FIG. 12 shows the detected inhibitory activity ($IC_{50}$) of mAb001c, mAb002c, and mAb004c on the catalytic function of CD73 on the surface of Calu-1 cells.

The detection results are shown in FIG. 12. mAb001c, mAb002c, and mAb004c could inhibit the function of CD73 on the surface of Calu-1 cells to catalyze the hydrolysis of AMP. $IC_{50}$ values were 0.506 nM, 0.281 nM, and 0.630 nM, respectively.

Example 10 Preparation of Humanized Antibody

The humanized templates that best matched mAb001c and mAb002c non-CDR regions were searched and selected in the Germline database, and then the CDR regions of the antibody were transplanted to the selected humanized templates, and the CDR regions of the human template were replaced, and then the obtained sequences were recombined with IgG1 constant region. Meanwhile, based on the three-dimensional structure of the murine antibody, the embedded residues, the residues that directly interacted with the CDR regions, and the residues that had an important influence on the conformation of VL and VH were back mutated.

Specifically, the humanization of mAb001c obtained 7 humanized heavy chain variable regions (SEQ ID NO. 31, SEQ ID NO. 32, SEQ ID NO. 33, SEQ ID NO. 34, SEQ ID NO. 35, SEQ ID NO. 45, and SEQ ID NO. 46), and 3 humanized light chain variable regions (SEQ ID NO. 36, SEQ ID NO. 37, and SEQ ID NO. 47).

mAb001-VH_HuG.3
SEQ ID NO. 31
QVQLVQSGAEVKKPGASVKVSCKTSGYTFTNYYIYWVRQAPGQRLEWMGW
IYPGNLNIKYNEKFKGRVTITADTSASTAYMELSSLRSEDTAVYYCARDD
NYAWFAYWGQGTLVTVSS mAb001-VH_HuG.5
SEQ ID NO. 32
QVQLVQSGAEVKKPGASVKVSCKASGYTFTNYYIYWVRQAPGQRLEWIGW
IYPGNLNIKYNEKFKGRVTITADKSASTAYMELSSLRSEDTAVYYCARDD
NYAWFAYWGQGTLVTVSS mAb001-VH_HuG.6
SEQ ID NO. 33
QVQLVQSGAEVKKPGASVKVSCKASGYTFTNYYIYWVKQRPGQRLEWIGW
IYPGNLNIKYNEKFKGRVTITADKSASTAYMELSSLRSEDTAVYYCARDD
NYAWFAYWGQGTLVTVSS mAb001-VH_HuG.7
SEQ ID NO. 34
QVQLVQSGAEVKKPGASVKVSCKASGYTFTNYYIYWVKQRPGQGLEWIGW
IYPGNLNIKYNEKFKGRVTITADKSASTAYMELSSLRSEDTAVYYCARDD
NYAWFAYWGQGTLVTVSS mAb001-VH_HuG.8
SEQ ID NO. 35
QVQLVQSGAEVKKPGASVKVSCKTSGYTFTNYYIYWVKQRPGQGLEWIGW
IYPGNLNIKYNEKFKGRVTITADKSASTAYMELSSLRSEDTAVYYCARDD
NYAWFAYWGQGTLVTVSS mAb001-VH_HuG.9
SEQ ID NO. 45
QVQLVQSGAEVKKPGASVKVSCKASGYTFTNYYIYWVRQAPGQRLEWIGW
IYPGNLNIKYNEKFKGRSTLTADKSASTAYMELSSLRSEDTAVYYCARDD
NYAWFAYWGQGTLVTVSS mAb001-VH_HuG.10
SEQ ID NO. 46
QVQLVQSGAEVKKPGASVKVSCKASGYTFTNYYIYWVKQRPGQRLEWIGW
IYPGNLNIKYNEKFKGRSTLTADKSASTAYMELSSLRSEDTAVYYCARDD
NYAWFAYWGQGTLVTVSS mAb001-VK_HuG.1
SEQ ID NO. 36
DIQMTQSPSSLSASVGDRVTITCKASQDVSTAVAWYQQKPGKAPKLLIYW
TNTRHTGVPSRFSGSGSGTDHTLTISSLQPEDFATYYCQQHYSTPFTFGQ
GTKLEIK mAb001-VK_HuG.2
SEQ ID NO. 37
DIQMTQSPSSLSASVGDRVTITCKASQDVSTAVAWYQQKPGKSPKLLIYW
TNTRHTGVPSRFSGSGSGTDHTLTISSLQPEDFATYYCQQHYSTPFTFGQ
GTKLEIK mAb001-VK_HuG.0
SEQ ID NO. 47
DIQMTQSPSSLSASVGDRVTITCKASQDVSTAVAWYQQKPGKAPKLLIYW
TNTRHTGVPSRFSGSGSGTDFTLTISSLQPEDFATYYCQQHYSTPFTFGQ
GTKLEIK

Specifically, the humanization of mAb002c obtained 4 humanized heavy chain variable regions (SEQ ID NO. 38, SEQ ID NO. 39, SEQ ID NO. 40, and SEQ ID NO. 41) and 3 humanized light chains variable regions (SEQ ID NO. 42, SEQ ID NO. 43, and SEQ ID NO. 44).

mAb002-VH_HuG0
SEQ ID NO. 38
QVQLVQSGAEVKKPGASVKVSCKASGYTLTSYWMHWVRQAPGQGLEWMGE
INPSQGRSNYNEKFKSRVTMTRDTSTSTVYMELSSLRSEDTAVYYCARRG
VSGNYFDYWGQGTLVTVSS mAb002-VH_HuG1
SEQ ID NO. 39
QVQLVQSGAEVKKPGASVKVSCKASGYTLTSYWMHWVRQAPGQGLEWIGE
INPSQGRSNYNEKFKSRVTLTVDRSTSTVYMELSSLRSEDTAVYYCARRG
VSGNYFDYWGQGTLVTVSS mAb002-VH_HuG2
SEQ ID NO. 40
QVQLVQSGAEVKKPGASVKVSCKASGYTLTSYWMHWVRQAPGQGLEWIGE
INPSQGRSNYNEKFKSKVTLTVDRSTSTVYMELSSLRSEDTAVYYCARRG
VSGNYFDYWGQGTLVTVSS mAb002-VH_HuG3
SEQ ID NO. 41
QVQLVQSGAEVKKPGASVKVSCKASGYTLTSYWMHWVKKAPGQGLEWIGE
INPSQGRSNYNEKFKSKVTLTVDRSTSTVYMELSSLRSEDTAVYYCARRG
VSGNYFDYWGQGTLVTVSS mAb002-VK_HuG1
SEQ ID NO. 42
DIQMTQSPSSLSASVGDRVTITCKASQDINTYLSWFQQKPGKAPKSLIYR
SNILVSGVPSRFSGSGSGQDYTLTISSLQPEDFATYYCLQYDEFPYTFGQ
GTKLEIK mAb002-VK_HuG2
SEQ ID NO. 43
DIQMTQSPSSLSASVGDRVTITCKASQDINTYLSWFQQKPGKSPKSLIYR
SNILVSGVPSRFSGSGSGQDYTLTISSLQPEDFATYYCLQYDEFPYTFGG
GTKLEIK mAb002-VK_HuG3
SEQ ID NO. 44
DIQMTQSPSSLSASVGDRVTITCKASQDINTYLSWFQQKPGKSPKSLIYR
SNILVSGVPSRFSGSGSGQDYTLTISSLQPEDFAIYYCLQYDEFPYTFGG
GTKLEIK

The designed humanized variable region sequence was cloned into a vector containing human IgG1 heavy chain constant region and Kappa chain constant region by using gene recombination technology. The vector was confirmed to be correct by sequencing, and then the constructed humanized antibodies were expressed using transfection technology and mammalian expression system (FreeStyle™ 293T cells). These humanized heavy and light chains were combined and expressed, respectively. Finally, the mAb001c-series obtained 11 humanized antibodies, and the mAb002-series obtained 12 humanized antibodies. The corresponding heavy and light chain combinations of each antibody are shown in following Table-2.

TABLE 2

Humanized antibodies

| Antibody name | VH SEQ ID NO: | VL SEQ ID NO: |
|---|---|---|
| Hu001c-14 | 31 | 36 |
| Hu001c-15 | 31 | 37 |
| Hu001c-21 | 32 | 36 |
| Hu001c-22 | 33 | 36 |
| Hu001c-23 | 34 | 36 |
| Hu001c-24 | 35 | 36 |
| Hu001c-25 | 32 | 37 |
| Hu001c-28 | 35 | 37 |
| Hu001c-30 | 46 | 47 |
| Hu001c-31 | 45 | 36 |
| Hu001c-32 | 46 | 36 |
| Hu002c-2 | 38 | 42 |
| Hu002c-3 | 38 | 43 |
| Hu002c-4 | 38 | 44 |
| Hu002c-6 | 39 | 42 |
| Hu002c-7 | 39 | 43 |
| Hu002c-8 | 39 | 44 |
| Hu002c-10 | 40 | 42 |
| Hu002c-11 | 40 | 43 |
| Hu002c-12 | 40 | 44 |
| Hu002c-14 | 41 | 42 |
| Hu002c-15 | 41 | 43 |
| Hu002c-16 | 41 | 44 |

Example 11 Affinity of Humanized Antibody to CD73

The humanized antibodies in Table 2 were serially diluted, and their affinity to CD73 protein was determined by ELISA. The experimental method was referred to Example 4.

Figure 14:
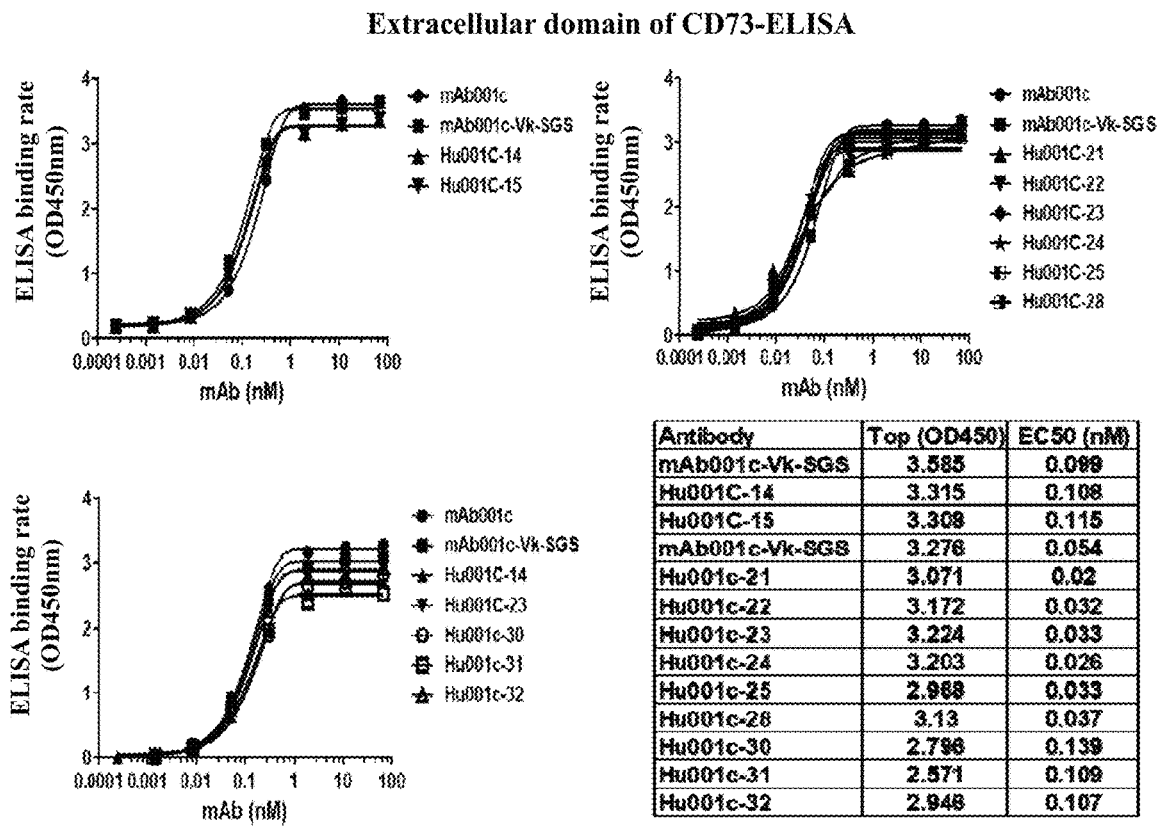
FIG. 14 shows the binding affinity ($EC_{50}$) of a series of mAb001c humanized antibodies (Hu001c-14 to 15, Hu001c-21 to 28, and Hu001c-30 to 32) to CD73-ECD as detected by ELISA.
Figure 15:
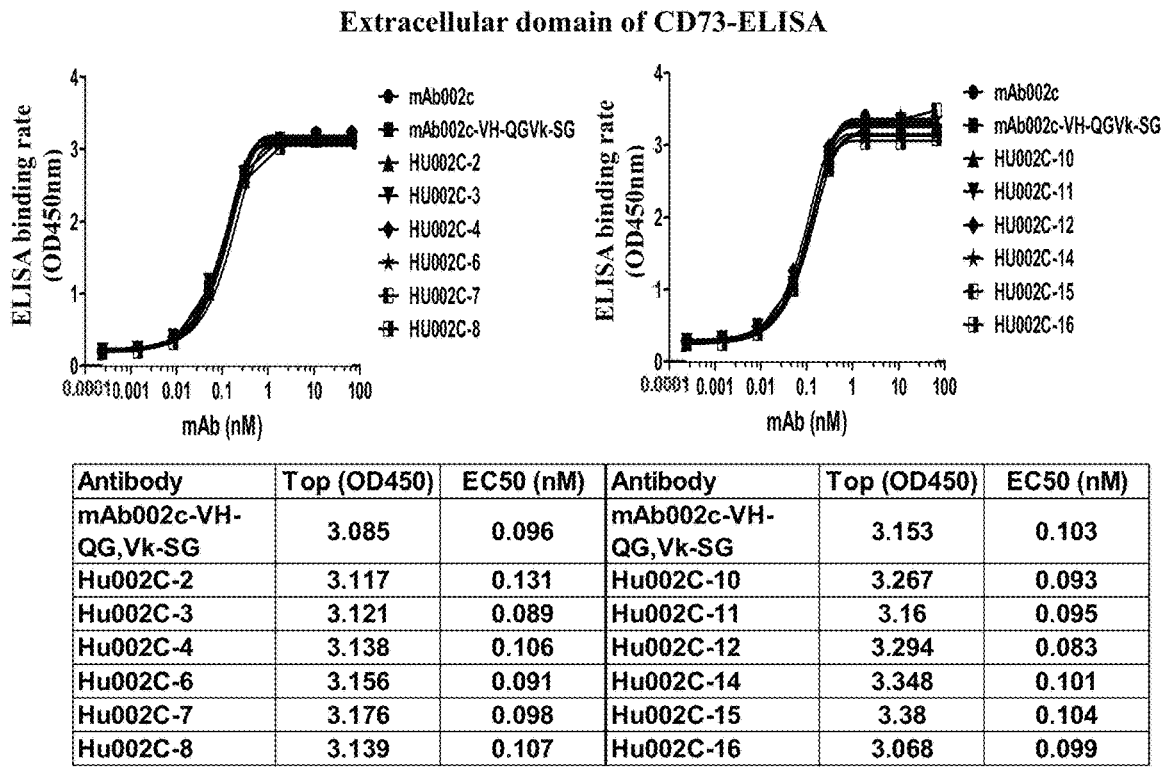
FIG. 15 shows the binding affinity ($EC_{50}$) of a series of mAb002c humanized antibodies (Hu002c-2 to 16) to CD73-ECD as detected by ELISA.

Experimental results are shown in FIG. 14 and FIG. 15. The two groups of humanized antibodies had strong binding affinity to CD73 protein, and the $EC_{50}$ values were 0.02 nM-0.13 nM.

Example 12 Inhibition of Humanized Antibody on Human CD73 Enzyme Function

The humanized antibodies in Table 2 were serially diluted, and the effect of the antibodies on the enzyme activity of recombinant CD73 was determined according to the method of Example 5.

Experimental results are shown in FIG. 16 and FIG. 17. The two groups of humanized antibodies had strong inhibitory effect on CD73 enzyme, and the $IC_{50}$ values were 0.02 nM-0.3 nM.

Example 13 Binding of Humanized Antibody to Tumor Cell CD73

The affinity of the humanized antibodies in Table 2 to CD73 on the surface of MDA-MB-231 and NCI-H1299 lung cancer cells was measured by flow cytometer, and the experimental method was referred to Example 6.

Figure 19:
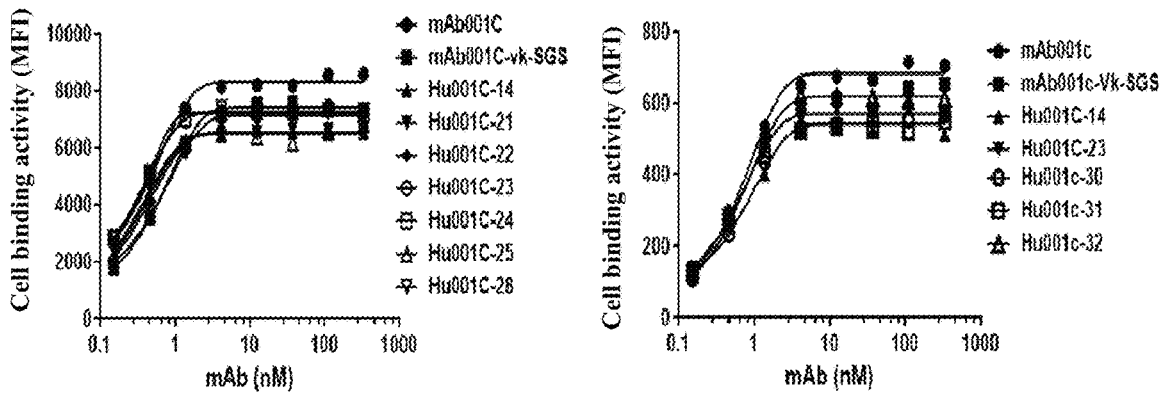
FIG. 19 shows the binding affinity ($EC_{50}$) of a series of mAb001c humanized antibodies (Hu001c-14, Hu001c-22 to 28, and Hu001c-30 to 32) to CD73 on the surface of MDA-MB-231 cells as detected by FACS. In this experiment, $1 \times 10^5$ cells were mixed with the antibody of a concentration gradient as shown, and detected after incubation for 1 hour.
Figure 21:
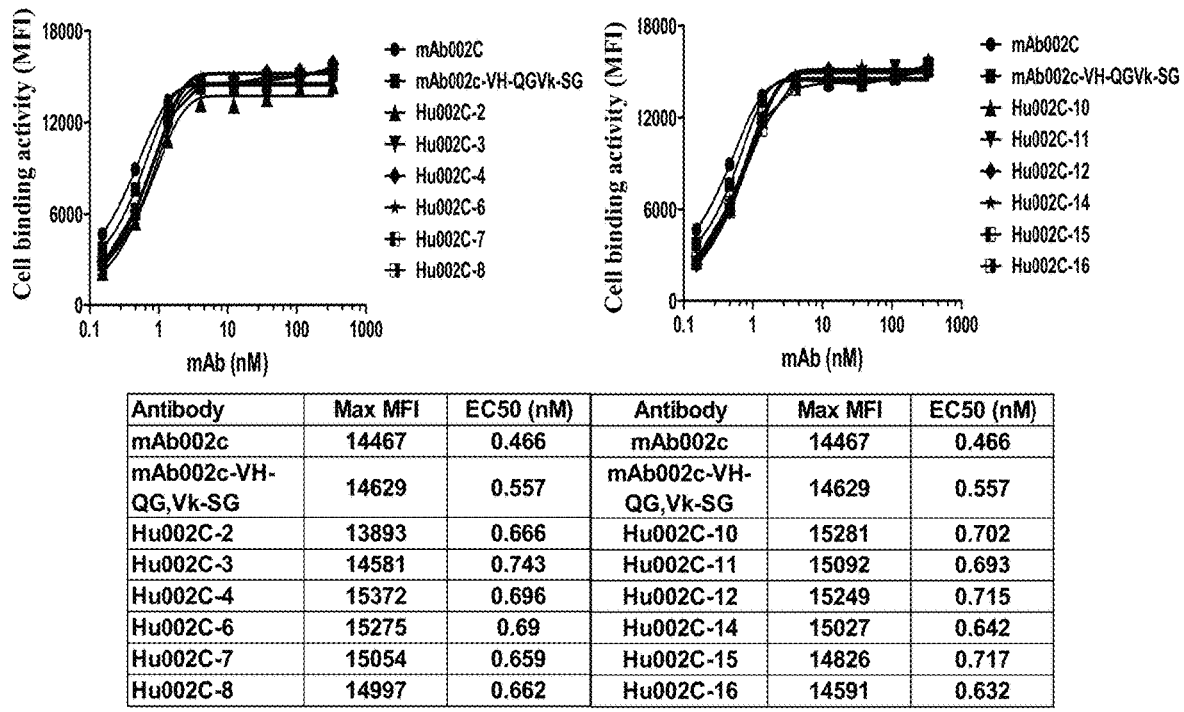
FIG. 21 shows the binding affinity ($EC_{50}$) of a series of mAb002c humanized antibodies (Hu002c-2 to 16) to CD73 on the surface of MDA-MB-231 cells as detected by FACS. In this experiment, $1 \times 10^5$ cells were mixed with the antibody of a concentration gradient as shown, and detected after incubation for 1 hour.

Experimental results are shown in FIG. 19 and FIG. 21. The two groups of humanized antibodies had high affinity for CD73 on the surface of MDA-MB-231 cells, and the $EC_{50}$ values were 0.2 nM-0.8 nM.

Figure 20:
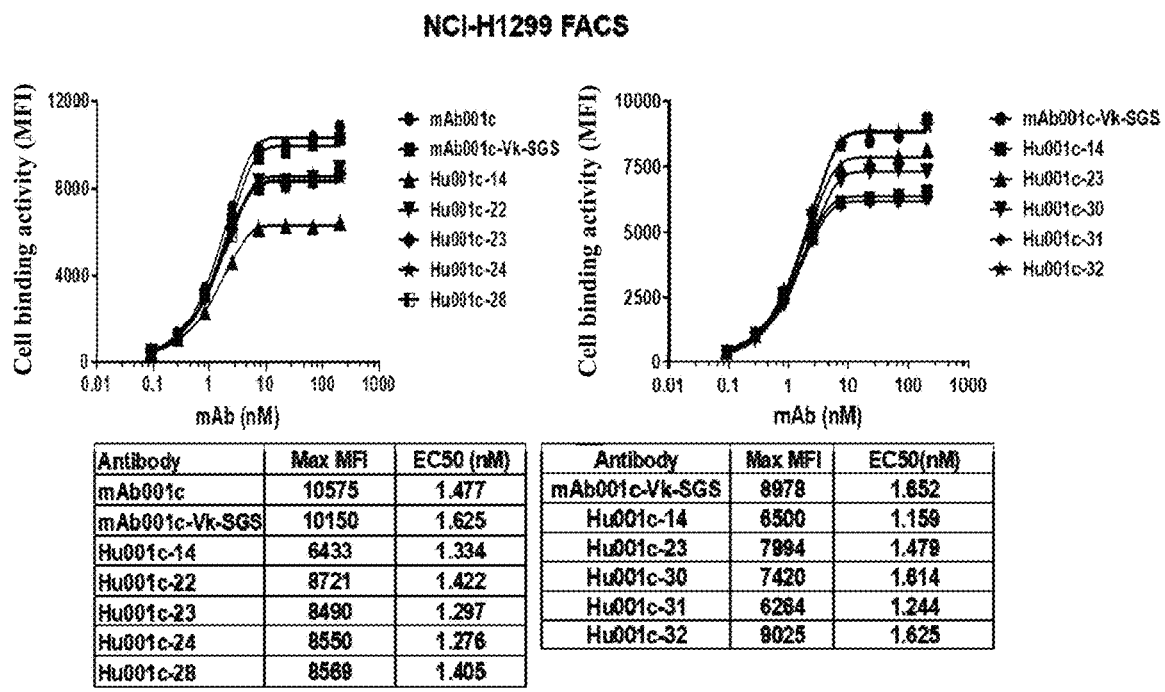
FIG. 20 shows the binding affinity ($EC_{50}$) of a series of mAb001c humanized antibodies (Hu001c-14, Hu001c-22 to 28, and Hu001c-30 to 32) to CD73 on the surface of NCI-H1299 cells as detected by FACS. In this experiment, $1 \times 10^5$ cells were mixed with the antibody of a concentration gradient as shown, and detected after incubation for 1 hour.
Figure 22:
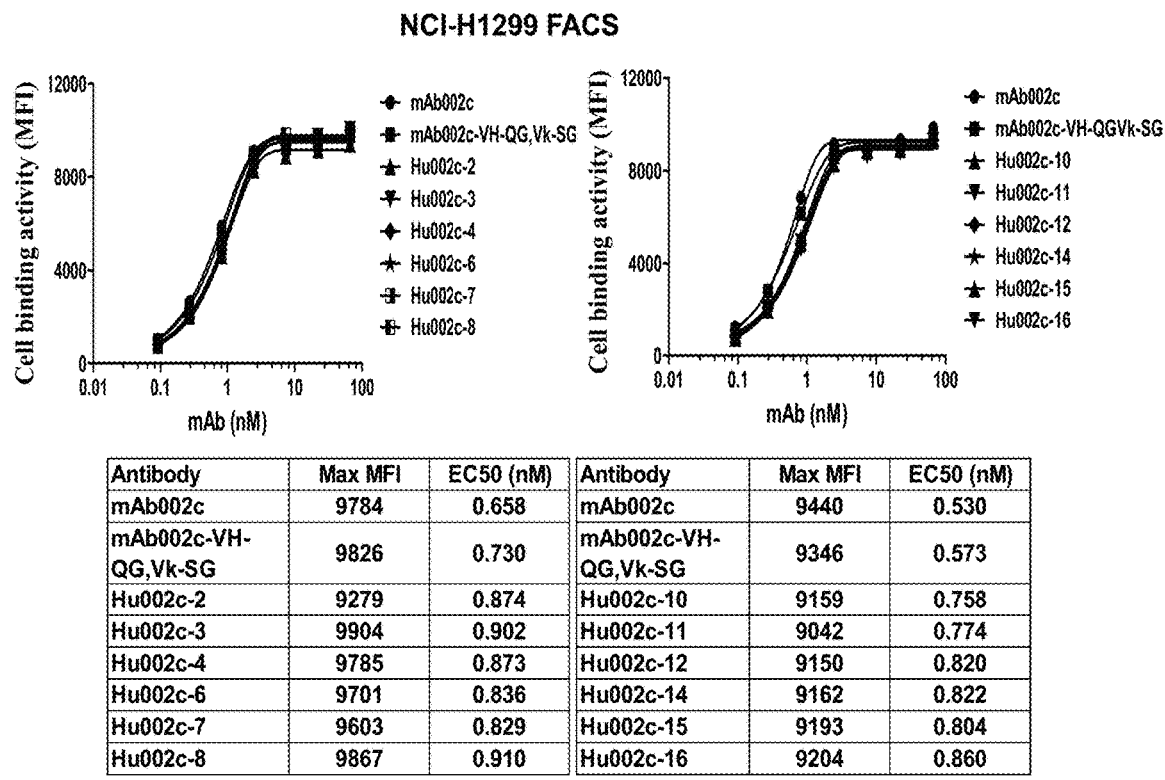
FIG. 22 shows the binding affinity ($EC_{50}$) of a series of mAb002c humanized antibodies (Hu002c-2 to 16) to CD73 on the surface of NCI-H1299 cells as detected by FACS. In this experiment, $1 \times 10^5$ cells were mixed with the antibody of a concentration gradient as shown, and detected after incubation for 1 hour.

Experimental results are shown in FIG. 20 and FIG. 22. The two groups of humanized antibodies had high affinity for CD73 on the surface of NCI-H1299 cells, and the $EC_{50}$ values were 0.3 nM-1.4 nM.

Example 14 Inhibitory Activity of Humanized Antibody on Tumor Cell CD73 Enzyme Function The effect of the humanized antibodies in Table 2 on the function of CD73 enzyme on the surface of NCI-H1299 cells was determined, and the experimental method was referred to Example 8.

Figure 23:
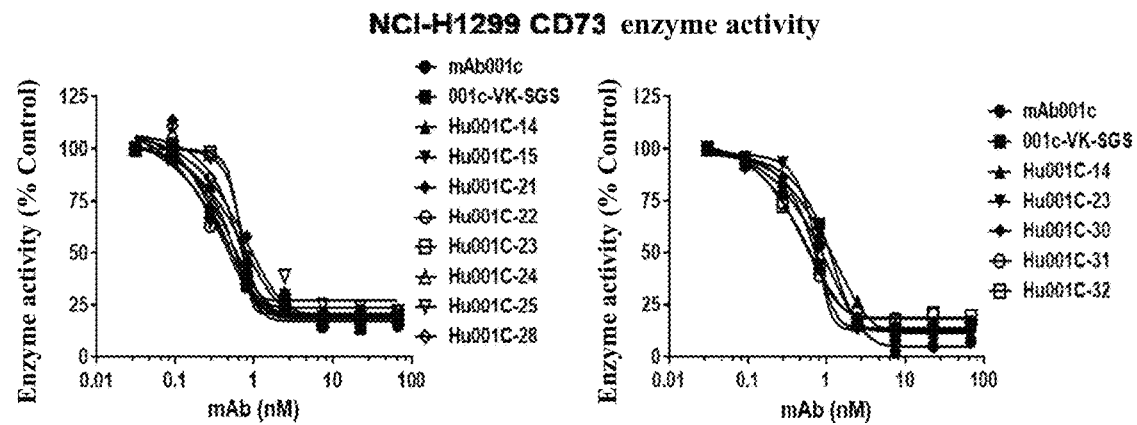
FIG. 23 shows the detected inhibitory activity ($IC_{50}$) of a series of mAb001c humanized antibodies (Hu001c-14 to 15, Hu001c-21 to 28, and Hu001c-30 to 32) on the catalytic function of CD73 on the surface of NCI-H1299 cells.
Figure 24:
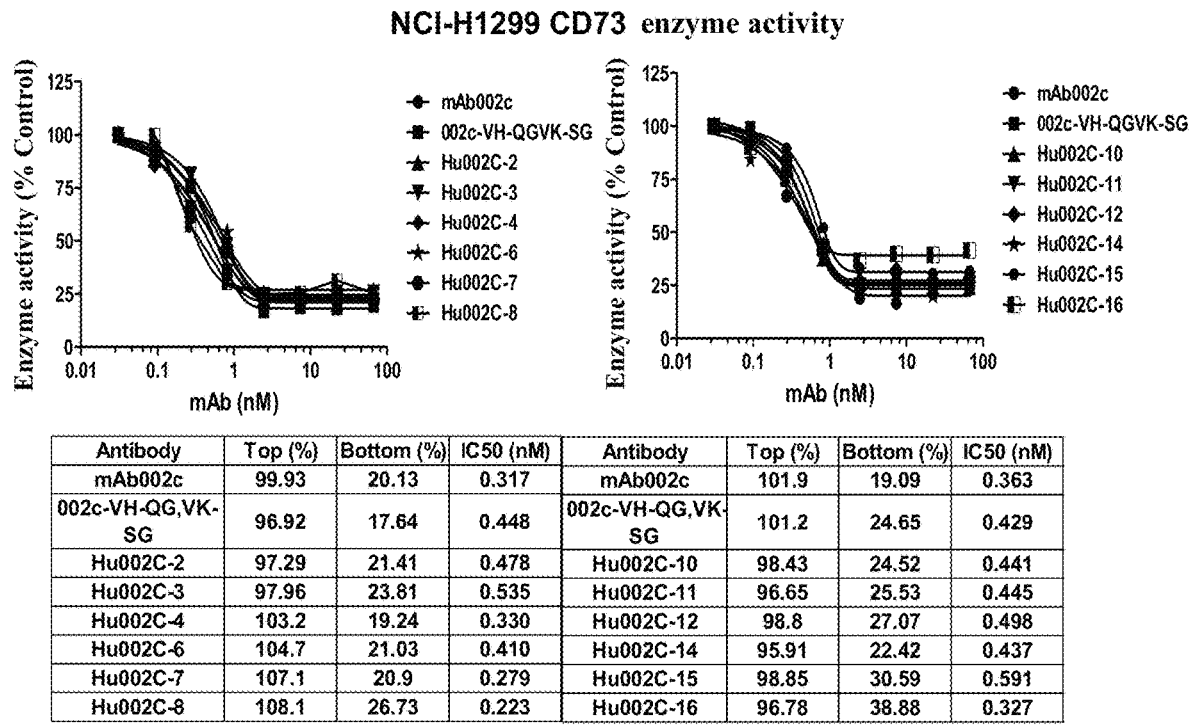
FIG. 24 shows the detected inhibitory activity ($IC_{50}$) of a series of mAb002c humanized antibodies (Hu002c-2 to 16) on the catalytic function of CD73 on the surface of NCI-H1299 cells.

Experimental results are shown in FIG. 23 and FIG. 24. The two groups of humanized antibodies had high inhibitory activity on the CD73 enzyme on the surface of NCI-H1299 cells, and the $IC_{50}$ values were 0.2 nM-0.6 nM.

Example 15 Binding of CD73 Chimeric Antibody to Tumor Cells LED to Internalization into Intracellular Lysosome MDA-MB-231 cells of 50% density were spread in a laser confocal culture dish, cultured at 37° C. for 16 hours, and then 5 μg/mL anti-CD73 antibody was added. The cells were incubated at 37° C. for 4 hours or 4° C. for 1 hour, washed three times with PBS to remove the antibodies unbound to the cells, and immobilized with 4% paraformaldehyde at room temperature for 30 minutes. The cells were washed three times with PBS and permeabilized with 0.4% Triton X-100 for 10 minutes. The cells were washed three times with PBS, the Lamp-2 (rabbit anti-human) antibody was added and incubated at 37° C. for 1 hour to mark the position of cell lysosome. The unbound antibodies were washed off with PBS, and R-PE-labeled goat anti-human and Alexa Fluor 488-labeled donkey anti-rabbit secondary antibodies were added and incubated at 37° C. for 30 min. The unbound secondary antibodies were washed off, the cells were stained with DAPI for 10 minutes to mark the position of the nucleus, and the antibody endocytosis situation was observed with a laser confocal microscope (20×).

Figure 25:
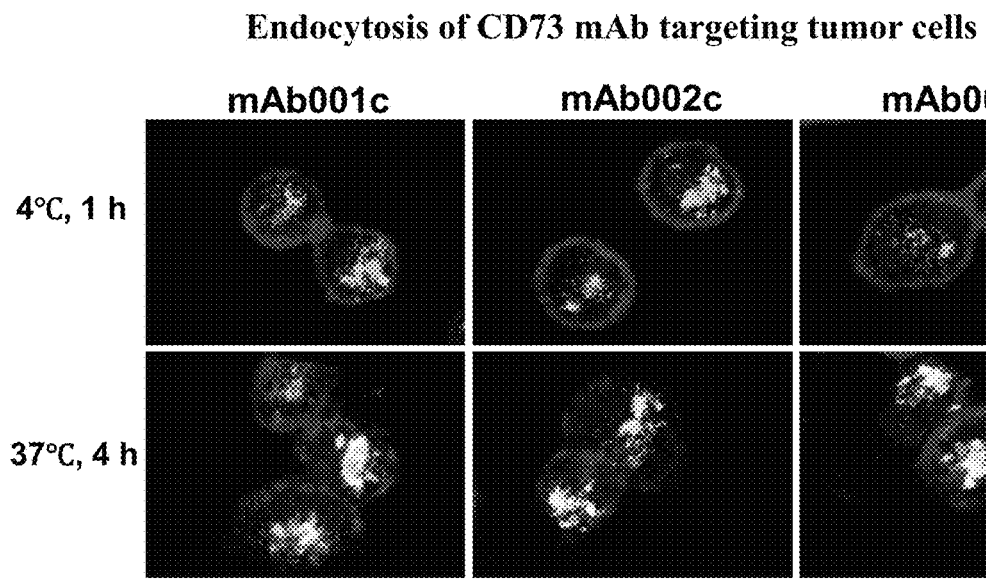
FIG. 25 shows that the binding of mAb001c, mAb002c, and mAb004c to MDA-MB-231 cells results in internalization into intracellular lysosome. The antibodies (5 µg/mL) were incubated with the cells at 4° C. for 1 hour, or at 37° C. for 4 hours, and then placed under a laser scanning confocal microscope to observe the results.

The results are shown in FIG. 25. All mAb001c, mAb002c, and mAb004c could be quickly and largely endocytosed by MDA-MB-231 cells into lysosome. The results indicate that the antibody of the present invention is suitable for preparing antibody-drug conjugates (ADC), suggesting that CD73-ADC will have good ADC drug properties and showing prospects as broad-spectrum and highly specific drugs for treatment of CD73-positive tumors.

Example 16 Anti-Tumor Activity of Humanized CD73 Antibody in Nude Mouse Xenograft Model Immunodeficient nude mice (Balb/c, nude) were randomly divided into several groups, and 100 μL of cell suspension containing $5×10^6$ U87MG, or $9×10^6$ NCI-H1299 and 100 μL of the humanized antibody were mixed well (final concentration was 50 μg/tumor), and then 200 μL of cell-antibody mixture was inoculated subcutaneously on the back of nude mice (n=4). hIgG1 was used as a negative control for subtype matching. The inhibitory effect of antibody on the growth of subcutaneous tumor was observed, the body weight and tumor size of nude mice were measured 2-3 times a week, and a tumor growth curve was drawn to evaluate the activity.

Figure 26:
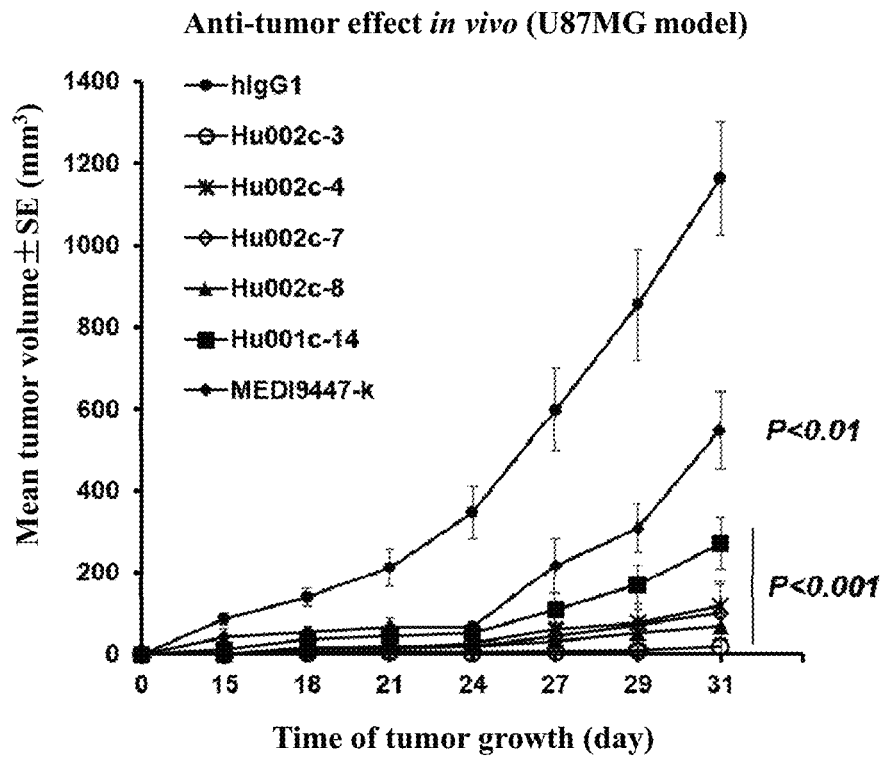
FIG. 26 shows the test of the anti-tumor activity of the humanized CD73 antibodies in vivo. In the experiment in vivo, the U87MG glioma cells with CD73-high expression were mixed with 50 µg antibody and inoculated subcutaneously on the back of nude mice. The observation was performed 2 to 3 times a week to measure tumor volume and mouse body weight.

The results are shown in FIG. 26. The humanized antibody Hu001c-14 and the humanized antibodies Hu002c-3 to 8 could significantly inhibit the growth of U87MG tumor in nude mice.

Figure 27:
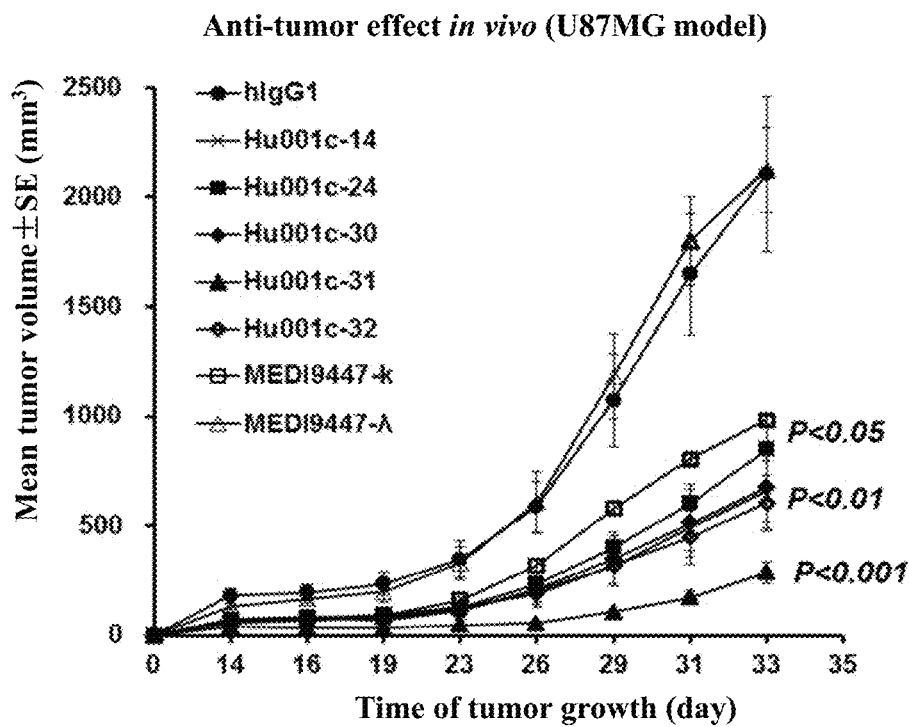
FIG. 27 shows the test of the anti-tumor activity of the humanized CD73 antibodies in vivo. In the experiment in vivo, the U87MG glioma cells were mixed with 50 µg antibody and inoculated subcutaneously on the back of nude mice. The observation was performed 2 to 3 times a week to measure tumor volume and mouse body weight.

The results are shown in FIG. 27. The humanized antibody Hu001c-14 and the humanized antibodies Hu001c-24 to 32 could significantly inhibit the growth of U87MG tumor in nude mice.

Figure 28:
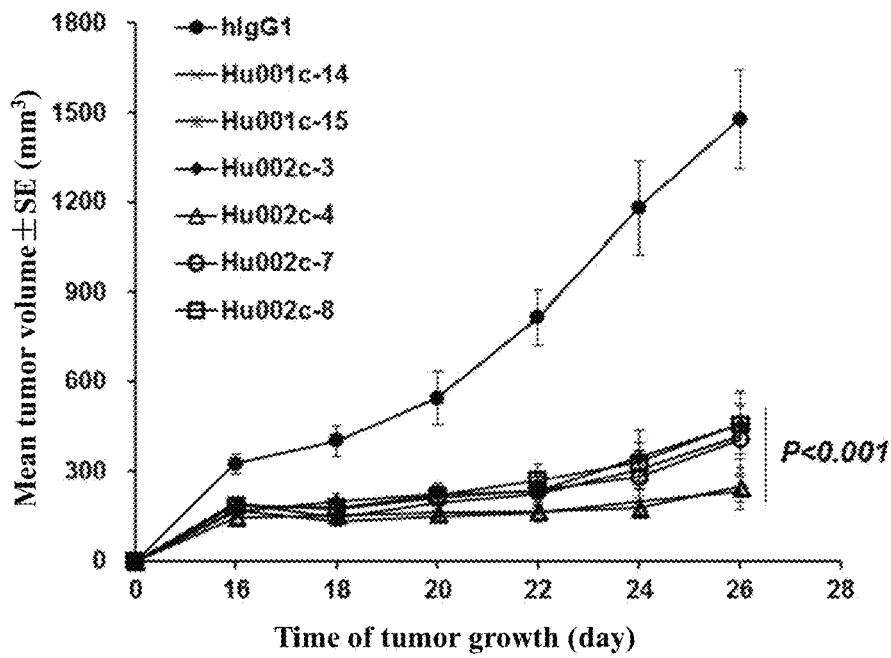
FIG. 28 shows the test of the anti-tumor activity of the humanized CD73 antibodies in vivo. In the experiment in vivo, the NCI-H1299 non-small cell lung cancer cells with CD73-high expression were mixed with 50 µg antibody and inoculated subcutaneously on the back of nude mice. The observation was performed 2 to 3 times a week to measure tumor volume and mouse body weight.

The results are shown in FIG. 28. The humanized antibodies Hu001c-14 to 15 and the humanized antibodies Hu002c-3 to 8 could significantly inhibit the growth of NCI-H1299 tumor in nude mice.

Figure 29:
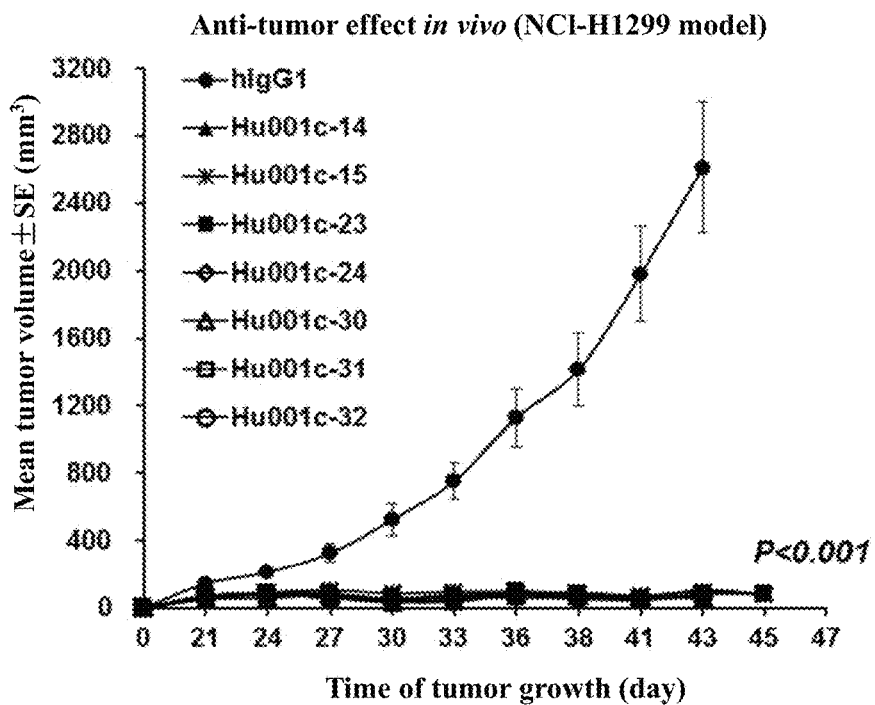
FIG. 29 shows the test of the anti-tumor activity of the humanized CD73 antibodies in vivo. In the experiment in vivo, the NCI-H1299 non-small cell lung cancer cells were mixed with 50 µg antibody and inoculated subcutaneously on the back of nude mice. The observation was performed 2 to 3 times a week to measure tumor volume and mouse body weight.

The results are shown in FIG. 29. The humanized antibodies Hu001c-14 to 15 and the humanized antibodies Hu001c-23 to 32 could significantly inhibit the growth of NCI-H1299 tumor in nude mice.

Example 17 Highly Abnormal Activation of CD73 in Triple Negative Breast

First, the total cell proteins of a variety of breast cell lines with different molecular classification were prepared and accurately quantified, and then the expression level of CD73 protein was detected by Western blot.

Figure 30:
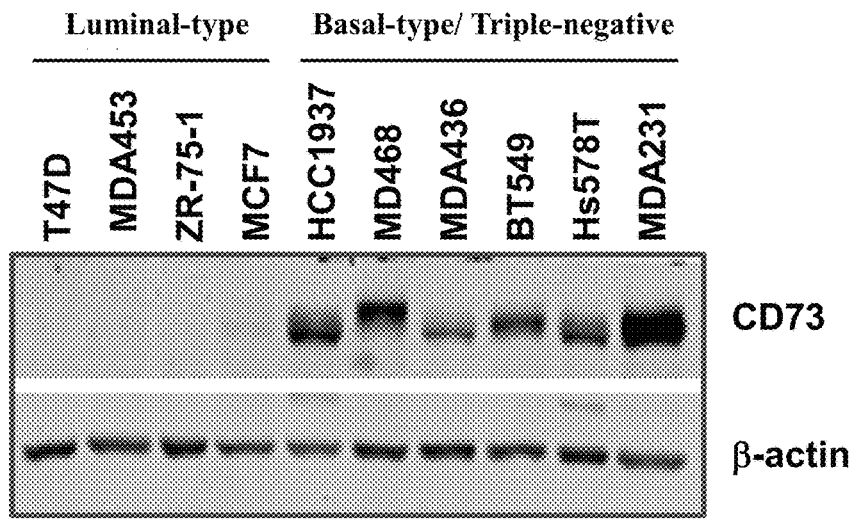
FIG. 30 shows the expression level of CD73 protein in highly invasive, highly metastatic basal-type breast cancer and luminal-type breast cancer cell lines as detected by Western blot.

The results are shown in FIG. 30. CD73 protein was highly abnormally activated and expressed in some highly invasive and highly metastatic basal-type breast cancer (basal-type, mostly clinically manifested as triple negative breast cancer) cell lines. However, CD73 protein was negatively or weakly expressed in the Luminal-type breast cancer (Luminal-type, most clinically manifested as hormone receptor-positive breast cancer) cell lines with relatively low degree of malignancy.

Figure 31:
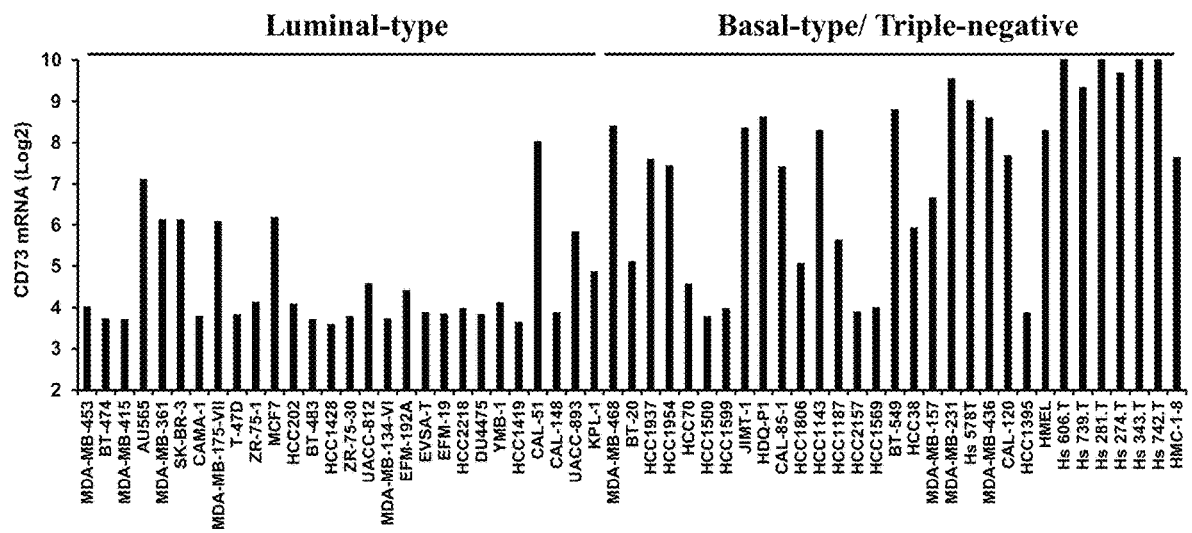
FIG. 31 shows the expression level of CD73 mRNA in the highly invasive and highly metastatic Basal-type vs. Luminal-type breast cancer cell line, based on an analysis of the Cancer Cell Line Encyclopedia (CCLE) database.

Then, the CD73 mRNA expression levels of breast cancer cell lines in the Cancer Cell Line Encyclopedia (CCLE) database were analyzed. The results are shown in FIG. 31. The expression level of CD73 mRNA in the Basal-type breast cancer cell line with high invasion and high metastasis was generally higher than that in the Luminal-type breast cancer cell line and the results has statistical significance. Therefore, the CD73 targeting antibody of the present invention will have a more significant effect in the application of diagnosis, prevention and treatment of triple negative breast cancer.

Example 18 Highly Abnormal Activation and Expression of CD73 in Lung Cancer

First, the total cell proteins of a variety of lung cell lines with different tissue sources and different molecular classification were prepared and accurately quantified, and then the expression level of CD73 protein was detected by Western blot.

Figure 32:
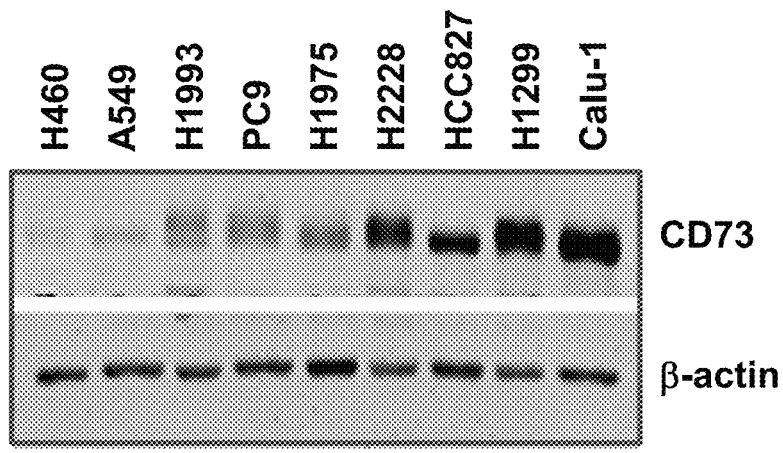
FIG. 32 shows the expression level of CD73 protein in different lung cancer cell lines as detected by Western blot.

The results are as shown in FIG. 32. CD73 protein is abnormally activated and expressed in many non-small cell lung cancer (NSCLC) cell lines.

Figure 33:
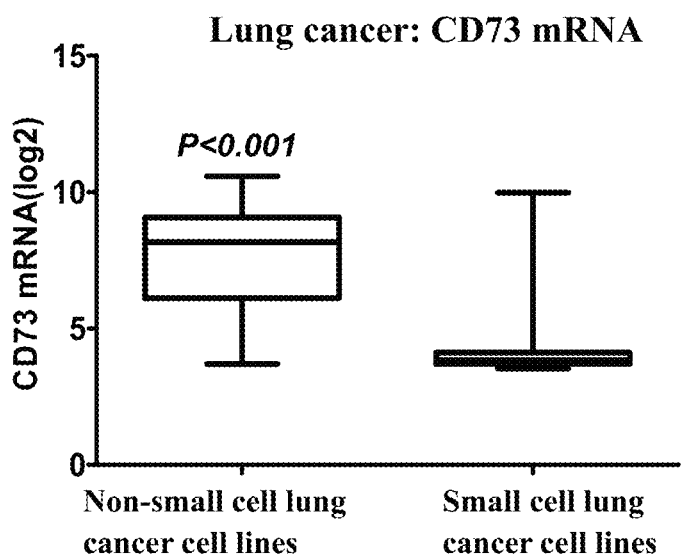
FIG. 33 shows the expression level of CD73 mRNA in non-small cell lung cancer (NSCLC) vs. small cell lung cancer (SCLC) cell lines, based on analysis of the Cancer Cell Line Encyclopedia (CCLE) database.

Then, the CD73 mRNA levels of lung cancer cell lines in the CCLE database were analyzed. The results are shown in FIG. 33. The expression level of CD73 mRNA in non-small cell lung cancer (NSCLC) cell lines was significantly higher than that in small cell lung cancer (SCLC), suggesting that the CD 73 targeting antibody of the present invention have a more significant effect in the application of diagnosis, prevention and treatment of non-small cell lung cancer (NSCLC).

Example 19 Protective Effect of Humanized CD73 Antibody on T Lymphocyte Proliferation and IFN-γ Expression Resuscitation, expansion and sorting of PBMC: first, PBMC was resuscitated and cultured for 3-4 days in a medium containing 500 ng/mL CD3/CD28 antibody and 100 IU/mL IL-2, and then the PBMC was sorted using a sorting kit (Stemcell, Cat #1795) to obtain CD3-positive T lymphocytes.

T cell proliferation test: the T cells obtained by the above sorting were fluorescently labeled, wherein a pre-prepared CFSE (carboxyfluorescein succinimidyl ester) was added into the cell suspension (with a final concentration of 2.5 µM), and the cells were labeled at 37° C. for 5 minutes and washed with PBS for 3 times. Then, the CFSE-labeled T cells were spread into a 96-well plate ($1-2\times10^4$ cells/well), and 50 µL of antibodies diluted in a gradient were added into each well (with a final concentration of 10 nM to 0.0001 nM, n=4), and 50 µL of adenosine monophosphate (AMP, the final concentration was 0.2 mM) was added and mixed well. The culture supernatant was collected after 4-5 days of culture. The number of cells in a fixed volume was read and counted using a Fluorescence Activated Cell Sorter (FACS). By using Flowjo software, the cell proliferation curve was drawn and the $EC_{50}$ value was calculated.

T cell IFN-γ detection: 50 µL/well of T cell culture supernatant was taken to detect the IFN-γ protein concentration by using an ELISA kit (Lianke Biotechnology Co., Ltd., Cat #EK180HS-48) and referring to the technical operation steps provided by the kit.

Figure 34:
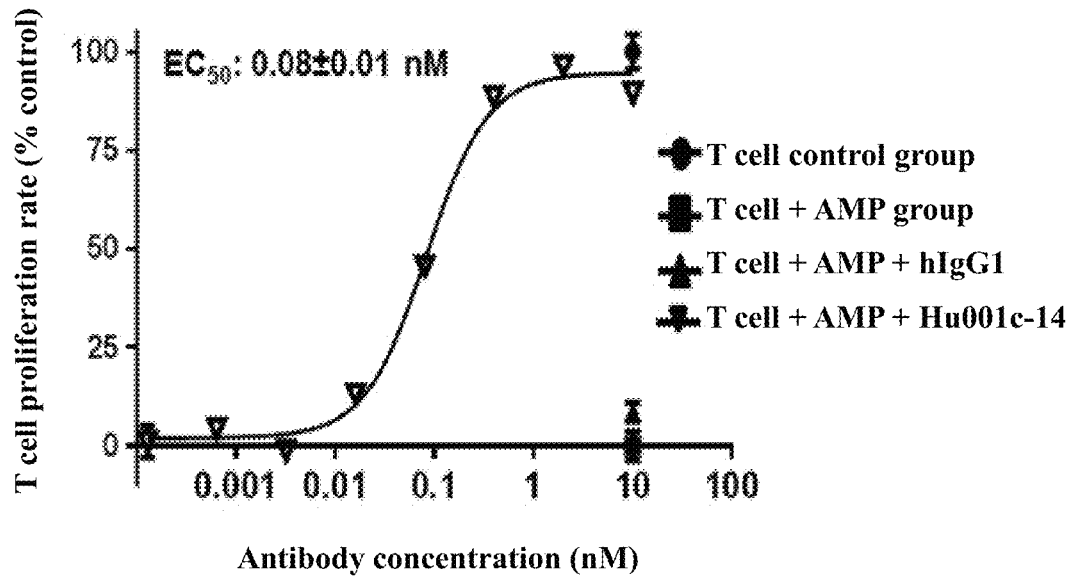
FIG. 34 shows that the humanized antibody Hu001c-14 can effectively reverse the inhibitory effect of adenosine monophosphate (AMP) on the proliferation of human T lymphocytes. CD3$^+$ human T cells obtained by sorting were used in the experiment, and the cell proliferation rate was counted after culturing for 5 days.
Figure 35:
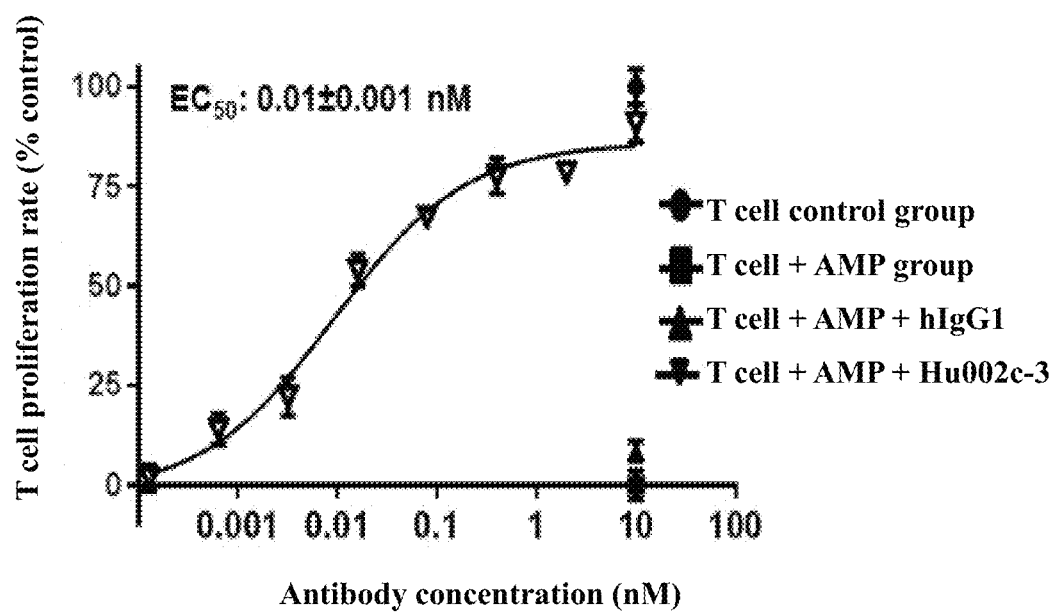
FIG. 35 shows that the humanized antibody Hu002c-3 can effectively reverse the inhibitory effect of AMP on the proliferation of human T lymphocytes. CD3$^+$ human T cells obtained by sorting were used in the experiment, and the cell proliferation rate was counted after culturing for 5 days.

The results are shown in FIG. 34 and FIG. 35. The humanized CD73 antibodies Hu001c-14 and Hu002c-3 had significant proliferation protective effects on human T lymphocytes, and could effectively reverse the inhibition of AMP on the proliferation of T cells, wherein the $EC_{50}$ values were 0.08±0.01 nM and 0.01±0.001 nM, respectively.

Figure 36:
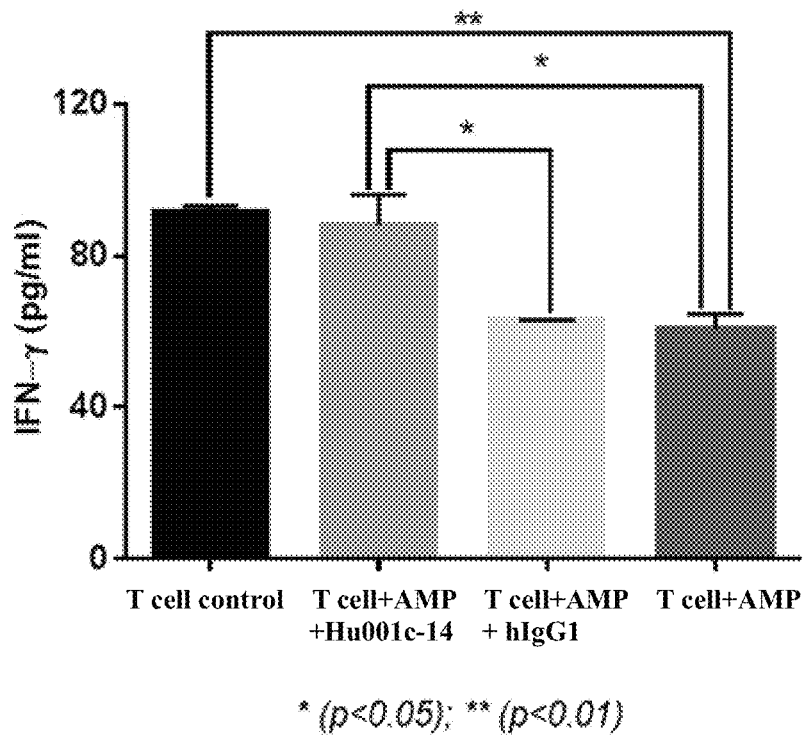
FIG. 36 shows that the humanized antibody Hu001c-14 can effectively reverse the inhibitory effect of AMP on the expression of INF-γ in human T lymphocyte. CD3$^+$ human T cells obtained by sorting were used in the experiment, and the T cell culture supernatant was detected after culturing for 5 days.
Figure 37:
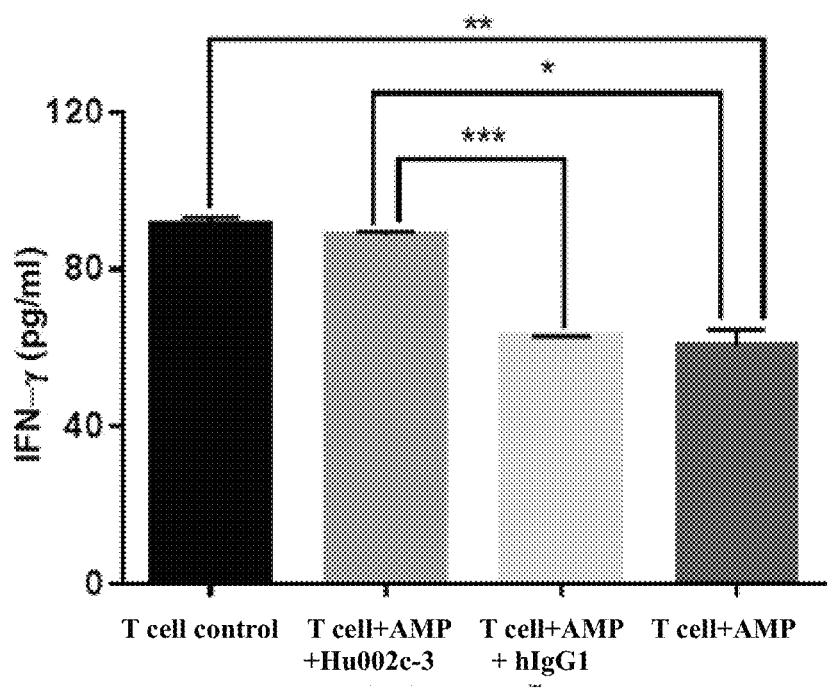
FIG. 37 shows that the humanized antibody Hu002c-3 can effectively reverse the inhibitory effect of AMP on the expression of INF-γ in human T lymphocyte. CD3$^+$ human T cells obtained by sorting were used in the experiment, and the T cell culture supernatant was detected after culturing for 5 days.

The results are shown in FIG. 36 and FIG. 37. The humanized CD73 antibodies Hu001c-14 and Hu002c-3 could effectively reverse the inhibitory effect of AMP on T cell expression/secretion of IFN-γ.

Example 20 Comparison of the CD73 Antibody with Those in the Prior Art

Using the heavy chain and light chain variable region sequences (VH/VL) of the MEDI9447 antibody disclosed in US20160194407, the heavy and light chain variable regions were artificially synthesized and cloned into a vector containing the constant region of human IgG1 heavy chain, a vector containing the constant region of Kappa chain or containing the constant region of Lambda chain, respectively. The obtained vectors were confirmed by sequencing, then expressed and purified in the FreeStyle™ 293T cell system to obtain MEDI9447-κ (which was consistent with the CD73 antibody of the present invention)□ or MEDI9447-λ, respectively. The experimental condition of antibody preparation was kept consistent with those in Example 3 and Example 10.

Heavy chain variable region (VH)
SEQ ID NO. 49
EVQLLESGGGLVQPGGSLRLSCAASGFTFSSYAYSWVRQAPGKGLEWVSA

ISGSGGRTYYADSVKGRFTISRDNSKNTLYLQMNSLRAEDTAVYYCARLG

YGRVDEWGRGTLVTVSS

Light chain variable region (VL)
SEQ ID NO. 50
QSVLTQPPSASGTPGQRVTISCSGSLSNIGRNPVNWYQQLPGTAPKLLIY

LDNLRLSGVPDRFSGSKSGTSASLAISGLQSEDEADYYCATWDDSHPGWT

FGGGTKLTVL

With reference to the methods in Examples 4-8, the ELISA affinity to CD73-ECD protein, the inhibitory activity on recombinant human CD73 enzyme, the binding affinity to tumor cells, and the inhibitory activity on CD73 enzyme of tumor cells of the above prepared MEDI9447-κ as well as the antibodies mAb001c and mAb002c were detected. The results of the study are summarized in Table-3.

TABLE 3

Test activity of antibodies

| Antibody name | MDA-MB-231 CD73 binding $EC_{50}$ (nM) | NCI-H1299 CD73 binding $EC_{50}$ (nM) | MDA-MB-231 CD73 Enzyme Inhibition $IC_{50}$ (nM) | NCI-H1299 CD73 Enzyme Inhibition $IC_{50}$ (nM) | Calu-1 CD73 Enzyme Inhibition $IC_{50}$ (nM) |
|---|---|---|---|---|---|
| mAb001c | 0.712 | 1.035 | 1.858 | 0.236 | 0.506 |
| mAb002c | 0.356 | 0.391 | 0.791 | 0.191 | 0.281 |
| MEDI9447-☐ | 0.752 | 1.272 | 1.099 | 0.388 | 0.527 |

At the same time, the prepared MEDI9447-κ antibody was used in the in vivo anti-tumor activity experiment. The CD73-high-expression U87MG glioma was selected as the in vivo tumor model. The antibody was mixed with $5 \times 10^6$ cells and then inoculated subcutaneously on the back of nude mice (50 μg antibody/tumor). The tumor growth and weight change were observed for 31 days. FIG. 26 shows the tumor growth curve of each group in the in vivo drug efficacy experiment. The anti-tumor activity on day 31 is summarized in Table-4.

TABLE 4

Anti-tumor activity of humanized antibodies in nude mice

| Antibody name | Tumor volume on day 31 ± SE (mm³) | Tumor inhibitory rate (%) | P value (compared to hIgG1) |
|---|---|---|---|
| hIgG1 | 1162.9 ± 137.7 | Control | Control |
| mAb001c | 139.06 ± 22.5 | 88 | <0.001 |
| Hu001c-14 | 271 ± 62.9 | 77 | <0.001 |
| Hu002c-3 | 19.4 ± 15.8 | 98 | <0.001 |
| Hu002c-4 | 119.2 ± 58.2 | 90 | <0.001 |
| Hu002c-7 | 102.3 ± 67.5 | 91 | <0.001 |
| Hu002c-8 | 68.7 ± 33.5 | 94 | <0.001 |
| MEDI9447-κ | 547.9 ± 96.4 | 53 | <0.01 |

Similarly, FIG. 27 shows the tumor growth curve of another group of humanized antibodies in the U87MG glioma in vivo experiment. The anti-tumor activity on day 33 is summarized in Table-5.

TABLE 5

Anti-tumor activity of humanized antibodies in nude mice

| Antibody name | Tumor volume on day 33 ± SE (mm³) | Tumor inhibitory rate (%) | P value (compared to hIgG1) |
|---|---|---|---|
| hIgG1 | 2105.1 ± 356 | Control | Control |
| Hu001c-14 | 660.4 ± 140 | 69 | <0.01 |
| Hu001c-24 | 849.1 ± 160 | 60 | <0.05 |
| Hu001c-30 | 672.9 ± 181 | 68 | <0.05 |
| Hu001c-31 | 287.4 ± 47 | 86 | <0.01 |
| Hu001c-32 | 604.2 ± 123 | 71 | <0.01 |
| MEDI9447-κ | 983.5 ± 17 | 53 | <0.05 |

In summary, the CD73 antibody of the present invention had a high affinity. Compared with those in prior art, the humanized antibodies of the Hu002c-series and Hu001c-series of the present invention had good or better anti-tumor activity in vitro and/or in vivo.

Example 21 Screening of Tumor Cell Lines with CD73 High Expression on the Cell Surface for ADC Drug Efficacy Determination $1 \times 10^5$ tumor cells were mixed well with the antibody mAb001c (final concentration was 10 μg/mL), and then incubated at 4° C. for 1 h. The cells were washed twice with PBS to remove the unbound primary antibody. Then the target cells were incubated with PE-labeled secondary antibody at 4° C. for 30 minutes. The cells were washed twice with PBS to remove the unbound secondary antibody. Finally, the cells were resuspended in 200 μL PBS and the binding rate was detected with a Fluorescence Activated Cell Sorter (FACS).

Figure 38:
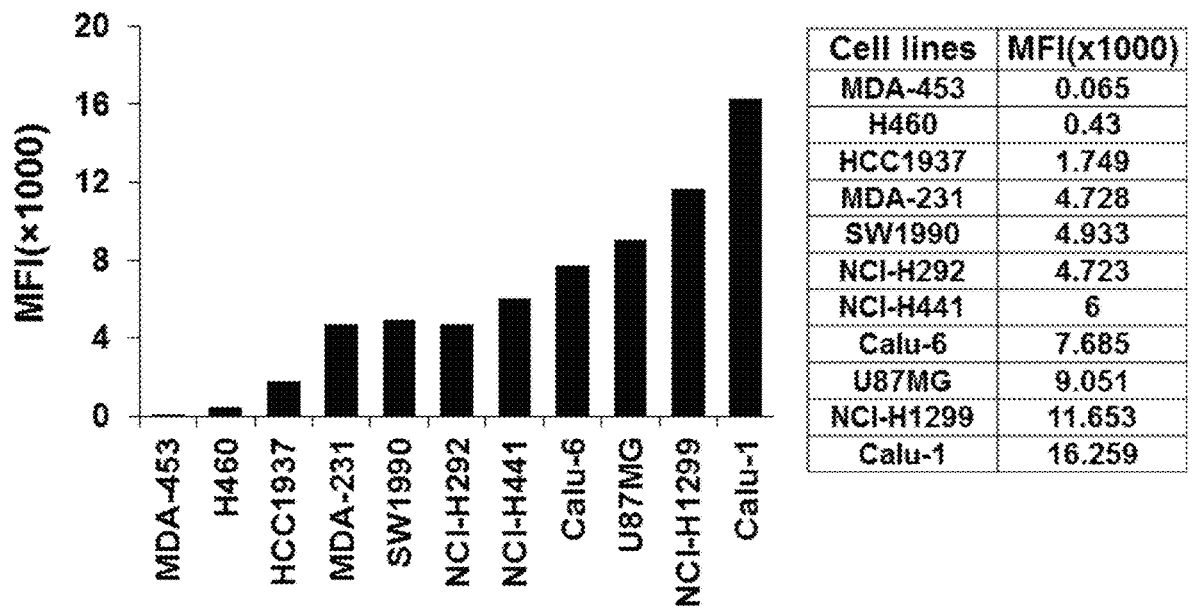
FIG. 38 shows the expression level (MFI) of CD73 receptor on the surface of breast cancer MDA-MB-453, HCC1937, MDA-MB-231, lung cancer NCI-H460, NCI-H292, NCI-H441, Calu-6, NCI-H1299, Calu-1, pancreatic cancer SW1990, glioma U87MG cells as detected by Fluorescence Activated Cell Sorter (FACS). In this experiment, 1×10$^5$ cells were mixed with 10 μg/mL mAb001c and detected after incubation for 1 hour.

The detection results are shown in FIG. 38. mAb001c could specifically recognize and bind CD73-high-expression tumor cells. The order of fluorescence intensity of binding rate was Calu-1, NCI-H1299, U87MG, Calu-6, NCI-H441, NCI-H292, SW1990, and MDA-MB-231. However, CD73-low-expression tumor cells MDA-MB-453 and NCI-H460 showed very weak binding fluorescence intensity.

Example 22 Binding of CD73 Humanized Antibody to Tumor Cells LED to Internalization into Intracellular Lysosome MDA-MB-231 cells of 50% density were spread in a laser confocal culture dish, cultured at 37° C. for 16 hours, and then 5 μg/mL CD73 antibody was added. The cells were incubated at 37° C. for 4 hours or 4° C. for 1 hour, washed three times with PBS to remove the antibodies unbound to the cells, and immobilized with 4% paraformaldehyde at room temperature for 30 minutes. The cells were washed three times with PBS and permeabilized with 0.4% Triton X-100 for 10 minutes. The cells were washed three times with PBS, the Lamp-2 (rabbit anti-human) antibody was added and incubated at 37° C. for 1 hour to mark the position of cell lysosome. The unbound antibodies were washed off with PBS, and R-PE-labeled goat anti-human and Alexa Fluor 488-labeled donkey anti-rabbit secondary antibodies were added and incubated at 37° C. for 30 min. The unbound secondary antibodies were washed off, the cells were stained with DAPI for 10 minutes to mark the position of the nucleus, and then the antibody endocytosis situation was observed with a laser confocal microscope (20×).

Figure 39:
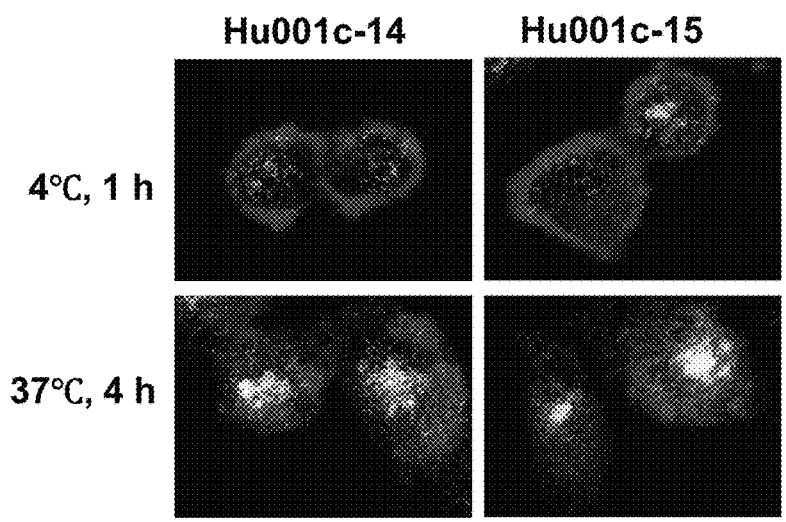
FIG. 39 shows that the binding of humanized CD73 antibodies Hu001c-14 and Hu001c-15 to MDA-MB-231 cells results in internalization into intracellular lysosome. The antibodies (5 μg/mL) were incubated with the cells at 4° C. for 1 hour, or at 37° C. for 4 hours, and then placed under a laser scanning confocal microscope to observe the results.

The results are shown in FIG. 39. Both of Hu001c-14 and Hu001c-15 could be quickly and largely endocytosed by MDA-MB-231 cells into lysosome. The results indicate that the antibody of the present invention is suitable for preparing antibody-drug conjugates (ADC), suggesting that CD73-ADC will have good ADC drug properties and showing prospects as broad-spectrum and highly specific drugs for the treatment of CD73-positive tumors.

Example 23 Preparation of Hu001c14-vcMMAE and Hu001c14-BL20-MMAE

Figure 40:
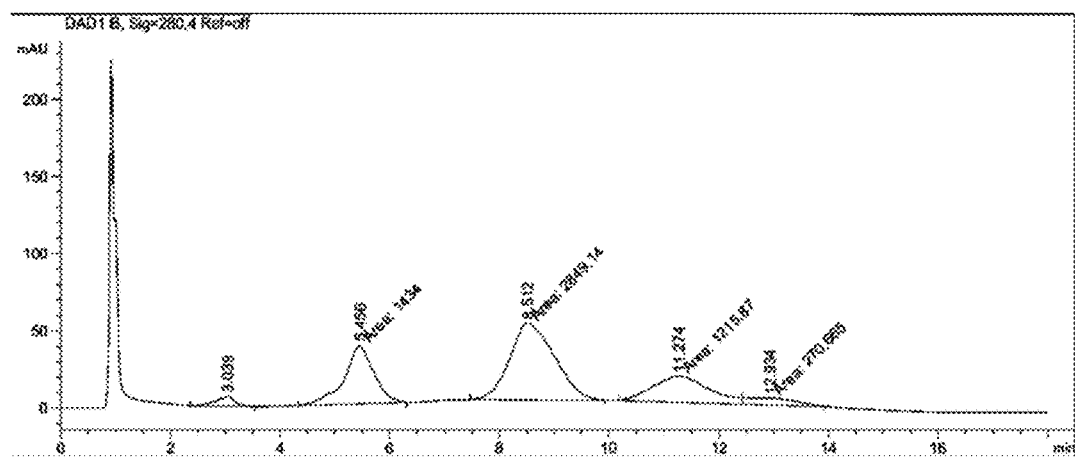
FIG. 40 shows the hydrophobic interaction chromatography (HIC) profile of the antibody-drug conjugate Hu001c14-vcMMAE.
Figure 42:
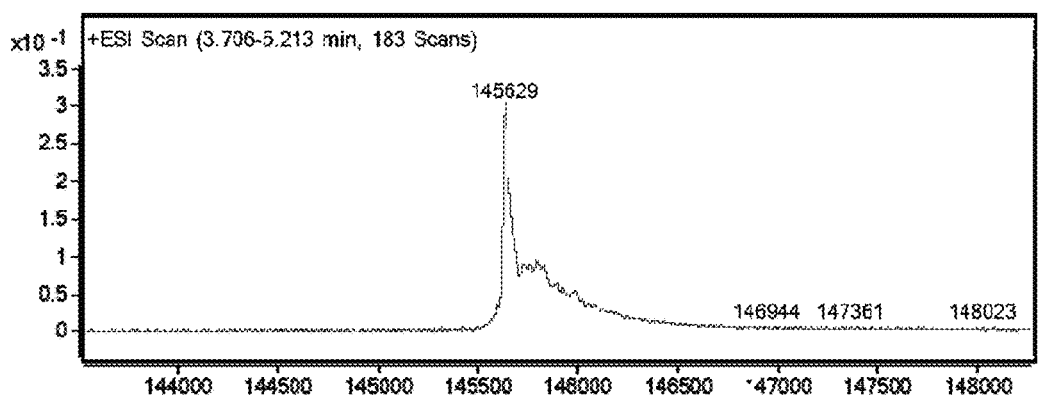
FIG. 42 shows the mass spectrum profile of monoclonal antibody Hu001c-14.
Figure 43:
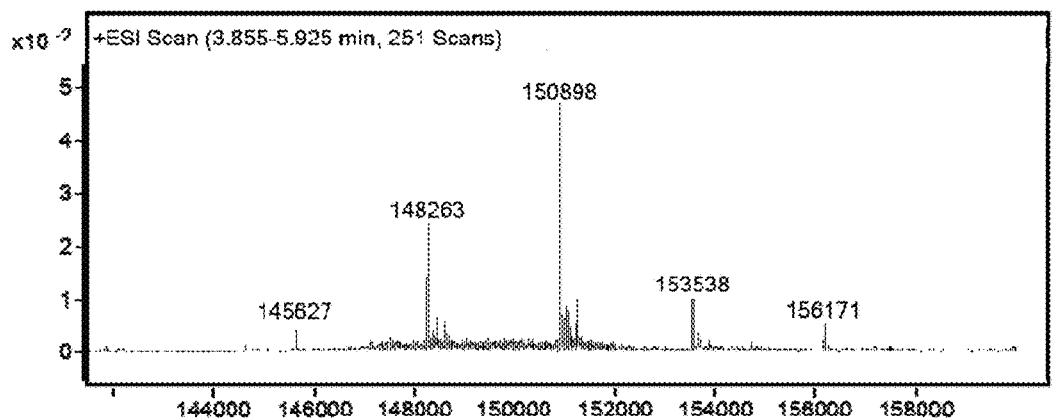
FIG. 43 shows the mass spectrum profile of the antibody-drug conjugate Hu001c14-vcMMAE.

PBS/EDTA (pH=7.4) buffer was added into the stock solution of humanized antibody Hu001c-14 targeting CD73 to make the concentration at 20 mg/ml, and the antibody was reduced with 2.6 eq of TCEP at 25° C. for 2 hours. The obtained solution was cooled on ice, added with 6.0 eq of mc-VC-PAB-MMAE (purchased from Shanghai Haoyuan Chemical Co., LTD, pre-dissolved in DMA) without purification, and reacted for 1 hour at 0° C. Then cysteine was added to stop the reaction. The excess small molecules were removed using a G25 desalting column, and the obtained product was placed into 20 mM citrate-sodium citrate/6% sucrose buffer (pH 6.6), sterilized through a filter device of 0.22 micron pore and preserved at −80° C. The obtained antibody conjugate was named Hu001c14-vcMMAE. The mass spectrum graph of humanized antibody Hu001c-14 (FIG. 42) and the HIC and mass spectrum graph of its antibody conjugate Hu001c14-vcMMAE (FIG. 40 and FIG. 43) all showed that the antibody was conjugated to form antibody conjugate Hu001c14-vcMMAE. The molecular weight of the conjugate was consistent with the expected value, and the average DAR value was about 4.0.

Figure 41:
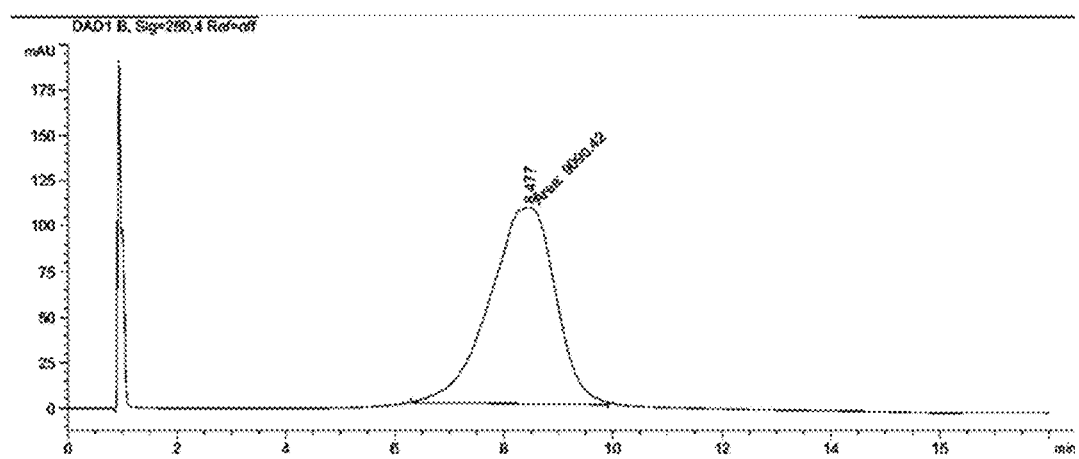
FIG. 41 shows the hydrophobic interaction chromatography (HIC) profile of the antibody-drug conjugate Hu001c14-BL20-MMAE.
Figure 44:
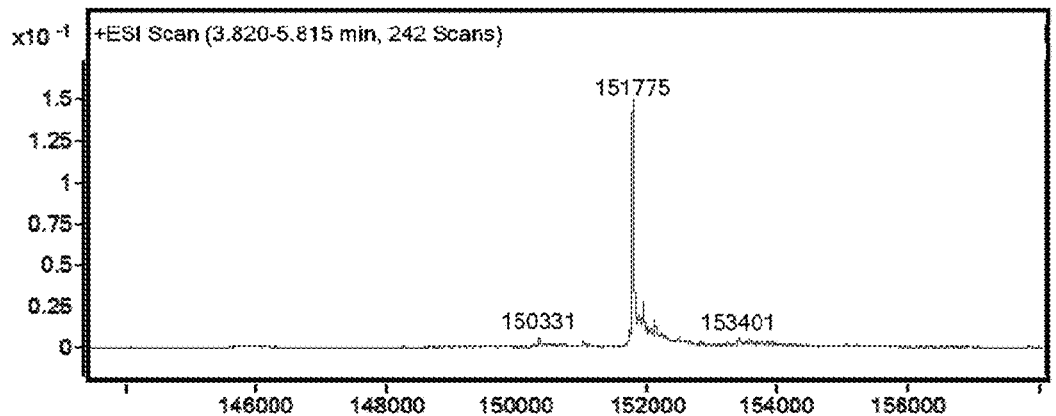
FIG. 44 shows the mass spectrum profile of the antibody-drug conjugate Hu001c14-BL20-MMAE.

The stock solution of humanized antibody Hu001c-14 was placed into 50 mM sodium dihydrogen phosphate-disodium hydrogen phosphate ($NaH_2PO_4$—$Na_2HPO_4$)/150 mM sodium chloride (NaCl)/2 mM ethylenediaminetetraacetic acid (EDTA) reaction buffer (pH 7.0), to make the concentration at 10 mg/mL. Tris(2-carboxyethyl)phosphine hydrochloride (TCEP) in a 10-fold excess molar ratio was added, and the reaction solution was stirring at 25° C. for 4 hours. The above reaction solution was cooled to 20° C. An appropriate amount of diethylacetamide (DMA) was added, and then Compound Ic-4 (10 mg/ml, pre-dissolved in DMA) in a 6-fold excess molar ratio was added and, ensuring that the volume of DMA in the reaction system did not exceed 10%. The obtained solution was stirring at 20° C. for 2.0 hours for coupling. The coupling reaction mixture was filtrated and purified by a desalting column with pH 7.5 Tris-hydrochloric acid/sucrose gel filtration, and peak samples were collected according to the UV280 absorption value. Then the peak samples were sterilized by a filter device of 0.22 micron pore, preserved at −80° C. The obtained antibody conjugate was named Hu001c14-BL20-MMAE. The mass spectrum graph of humanized antibody Hu001c-14 (FIG. 42) and the HIC and mass spectrum graph of its antibody conjugate Hu001c14-BL20-MMAE (FIG. 41 and FIG. 44) all showed that the antibody Hu001c-14 was conjugated to form antibody conjugate Hu001c14-BL20-MMAE. The molecular weight of the conjugate was consistent with the expected value, and the DAR value was about 4.0.

Example 24 Preparation of Hu001c15-vcMMAE and Hu001c15-BL20-MMAE

Figure 45:
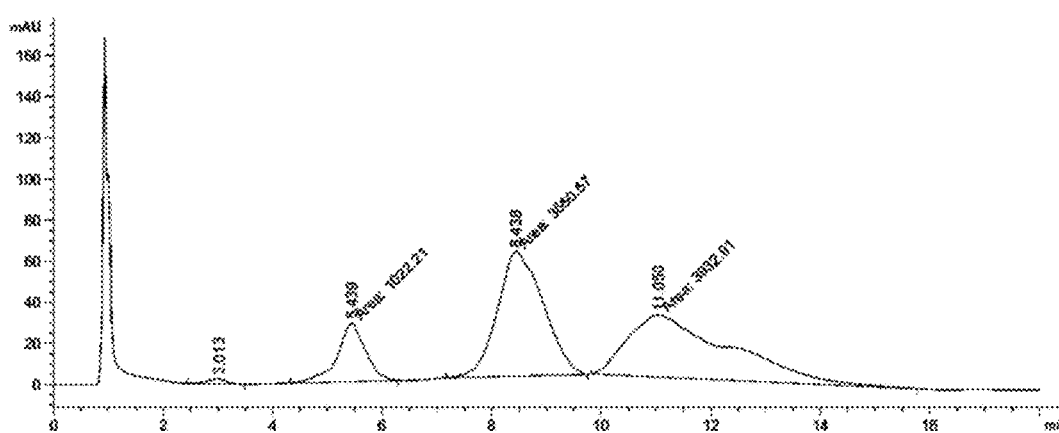
FIG. 45 shows the hydrophobic interaction chromatography (HIC) profile of the antibody-drug conjugate Hu001c15-vcMMAE.
Figure 47:
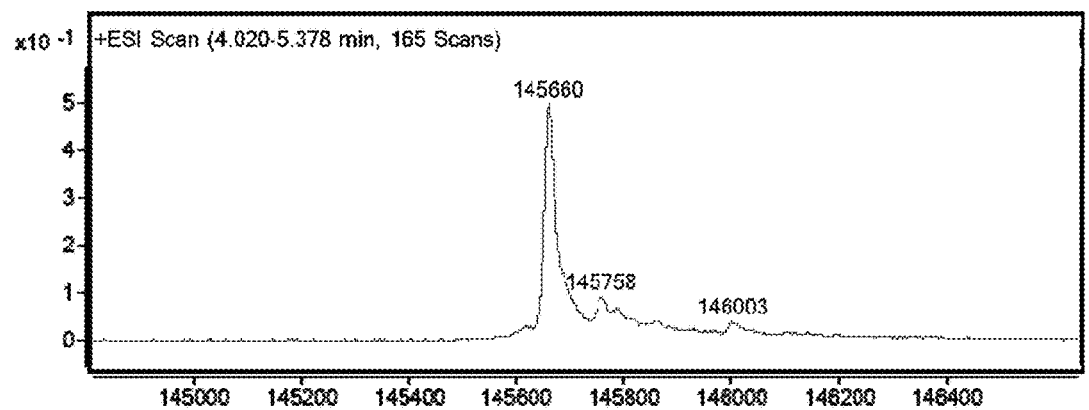
FIG. 47 shows the mass spectrum profile of monoclonal antibody Hu001c-15.
Figure 48:
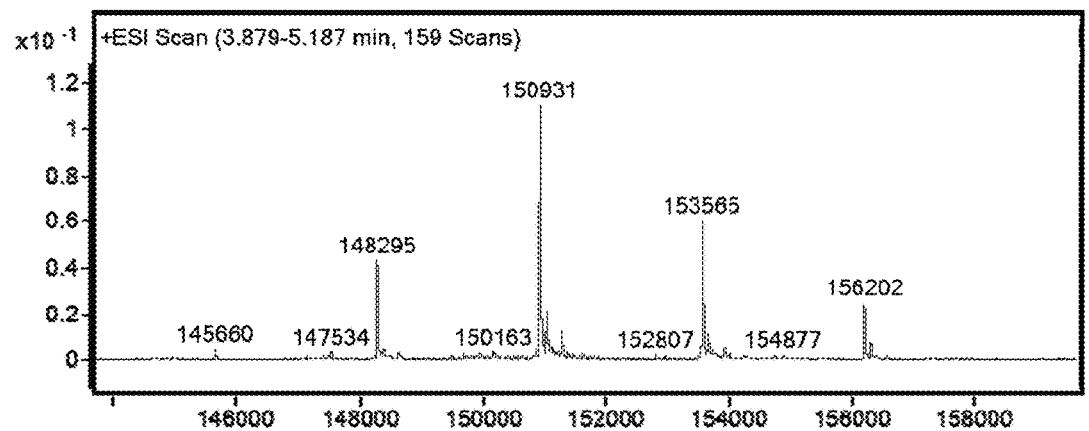
FIG. 48 shows the mass spectrum profile of the antibody-drug conjugate Hu001c15-vcMMAE.

PBS/EDTA (pH=7.4) buffer was added into the stock solution of humanized antibody Hu001c-15 targeting CD73 to make the concentration at 20 mg/ml, and the antibody was reduced with 2.6 eq of TCEP at 25° C. for 2 hours. The obtained solution was cooled on ice, added with 6.0 eq of mc-VC-PAB-MMAE (purchased from Shanghai Haoyuan Chemical Co., LTD, pre-dissolved in DMA) without purification, and reacted for 1 hour at 0° C. Then cysteine was added to stop the reaction. The excess small molecules were removed using a G25 desalting column, and the obtained product was placed into 20 mM citrate-sodium citrate/6% sucrose buffer (pH 6.6), sterilized through a filter device of 0.22 micron pore and preserved at −80° C. The obtained antibody conjugate was named Hu001c15-vcMMAE. The mass spectrum graph of antibody Hu001c-15 (FIG. 47) and the HIC and mass spectrum graph of its antibody conjugate Hu001c15-vcMMAE (FIG. 45 and FIG. 48) all showed that the antibody Hu001c-15 was conjugated to form antibody conjugate Hu001c15-vcMMAE. The molecular weight of the conjugate was consistent with the expected value, and the average DAR value was about 4.0.

Figure 46:
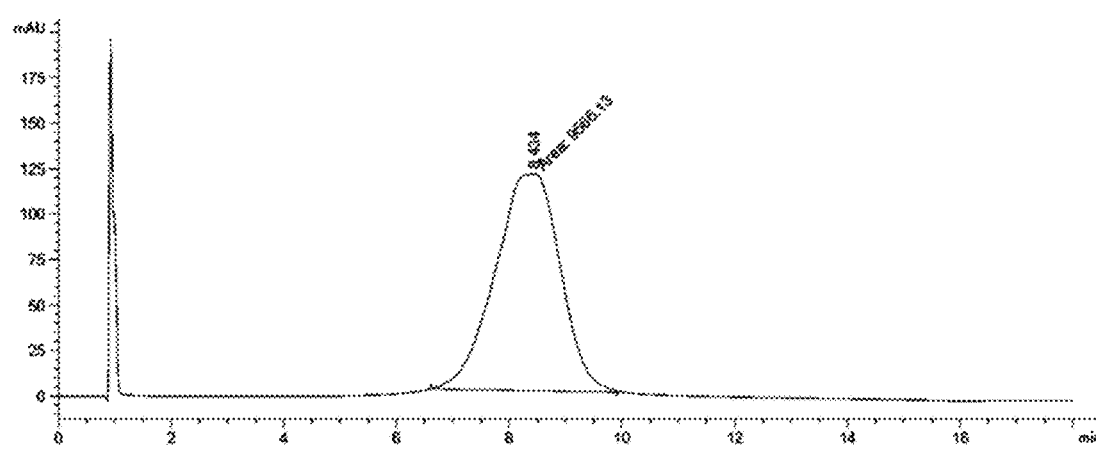
FIG. 46 shows the hydrophobic interaction chromatography (HIC) profile of the antibody-drug conjugate Hu001c15-BL20-MMAE.
Figure 49:
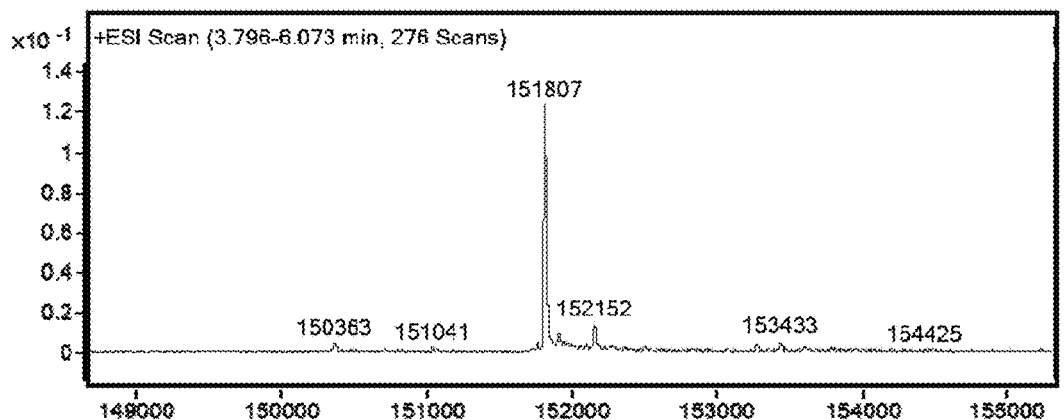
FIG. 49 shows the mass spectrum profile of the antibody-drug conjugate Hu001c15-BL20-MMAE.

The stock solution of antibody Hu001c-15 was placed into 50 mM sodium dihydrogen phosphate-disodium hydrogen phosphate ($NaH_2PO_4$—$Na_2HPO_4$)/150 mM sodium chloride (NaCl)/2 mM ethylenediaminetetraacetic acid (EDTA) reaction buffer (pH 7.0), to make the concentration at 10 mg/mL. Tris(2-carboxyethyl)phosphine hydrochloride (TCEP) in a 10-fold excess molar ratio was added, and the reaction solution was stirring at 25° C. for 4 hours. The above reaction solution was cooled to 20° C. An appropriate amount of diethylacetamide (DMA) was added, and then Compound Ic-4 (10 mg/ml, pre-dissolved in DMA) in a 6-fold excess molar ratio was added, ensuring that the volume of DMA in the reaction system did not exceed 10%. The obtained solution was stirring at 20° C. for 2.0 hours for coupling. The coupling reaction mixture was filtrated and purified by a desalting column with pH 7.5 Tris-hydrochloric acid/sucrose gel filtration, and peak samples were collected according to the UV280 absorption value. Then the peak samples were sterilized by a filter device of 0.22 micron pore, preserved at −80° C. The obtained antibody conjugate was named Hu001c15-BL20-MMAE. The mass spectrum graph of antibody Hu001c-15 (FIG. 47) and the HIC and mass spectrum graph of its antibody conjugate Hu001c15-BL20-MMAE (FIG. 46 and FIG. 49) all showed that the antibody Hu001c-15 was conjugated to form antibody conjugate Hu001c15-BL20-MMAE. The molecular 6 weight of the conjugate was consistent with the expected value, and the DAR value was about 4.0.

Example 25 In Vitro Anti-Tumor Activity of CD73 Antibody-Drug Conjugate (CD73-ADC) Against CD73-High-Expression Tumor Cells The cell lines used in this example were purchased from the American Type Culture Collection (ATCC) or the Cell Bank of the Chinese Academy of Sciences, and were cultured according to the corresponding instructions, including: MDA-MB-453, Calu-1, U87MG, Calu-6, NCI-H441, NCI-H292, MDA-MB-231, PC9, HCC827, and NCI-H1975. The above-mentioned cells in a logarithmic growth phase were inoculated respectively into a 96-well cell culture plate at a density of 800-2500 cells per well (depending on the growth rate of different cells) and 150 µL/well, the cells were cultured at 37° C., 5% $CO_2$ for about 5-12 hours, and then CD73-ADCs of different concentrations were added, respectively (for each drug concentration, 2-4 multiple wells, and the corresponding solvent control well and blank control well were set). After 5-6 days of interaction (according to the cell growth rate, ensuring enough cell division), the culture medium was poured off, MTS reaction solution (purchased from Promega, cat #G3581) was added at 100 µL/well, and reacted at 37° C. until the expected color appeared. The cell viability of each group was determined (OD490 nm), and the cell survival rate was calculated according to the following formula: survival rate=(OD administration−OD blank)/(ODcontrol−ODblank)×100%. The above data were analyzed with GraphPad Prism 5 software, and the $IC_{50}$ values of the above CD73 antibody-drug conjugate on different cell lines were calculated, respectively.

The in vitro anti-tumor activity results of four preferred humanized CD73-ADCs: Hu001c14-BL20-MMAE, Hu001c14-vcMMAE, Hu001c15-BL20-MMAE, and Hu001c15-vcMMAE are shown in FIG. 50 to FIG. 59, respectively.

Figure 50:
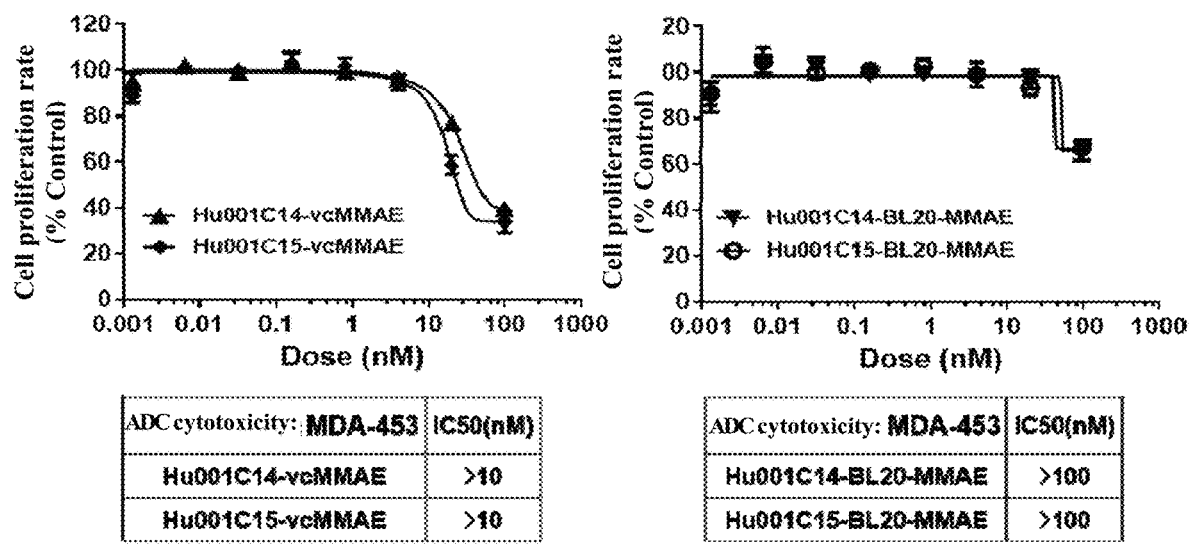
FIG. 50 shows the detection result of the inhibitory activity of the CD73 antibody-drug conjugate on the proliferation of breast cancer cell MDA-MB-453.
Figure 51:
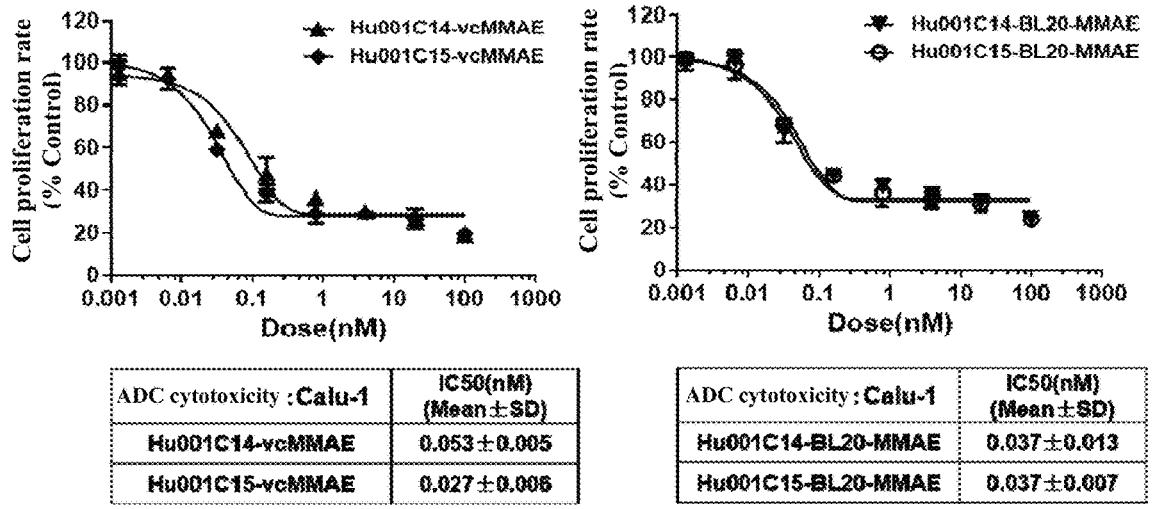
FIG. 51 shows the detection result of the inhibitory activity of the CD73 antibody-drug conjugate on the proliferation of lung cancer cell Calu-1.
Figure 52:
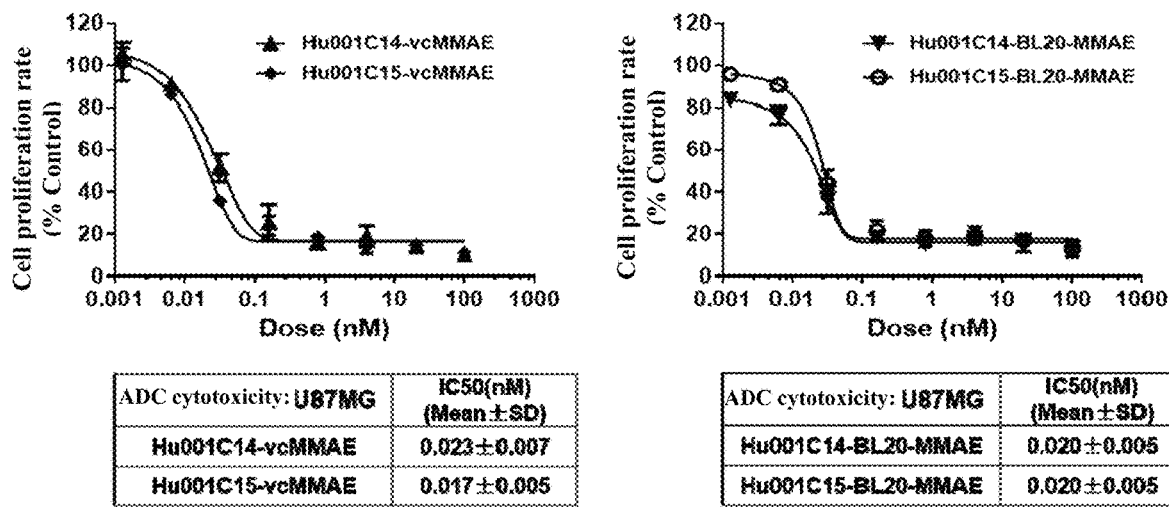
FIG. 52 shows the detection result of the inhibitory activity of the CD73 antibody-drug conjugate on the proliferation of glioma cell U87MG.
Figure 53:
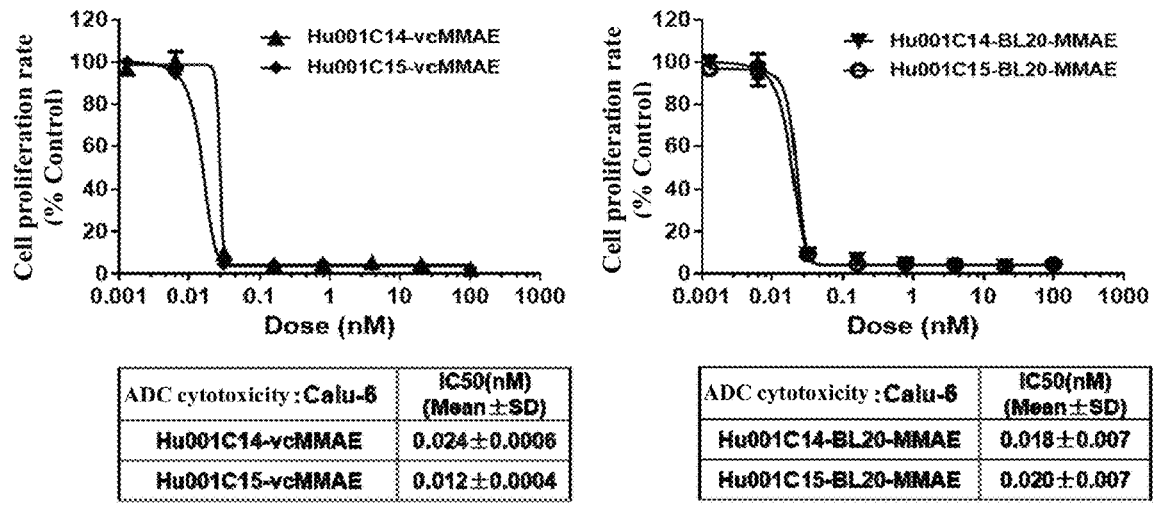
FIG. 53 shows the detection result of the inhibitory activity of the CD73 antibody-drug conjugate on the proliferation of lung cancer cell Calu-6.
Figure 54:
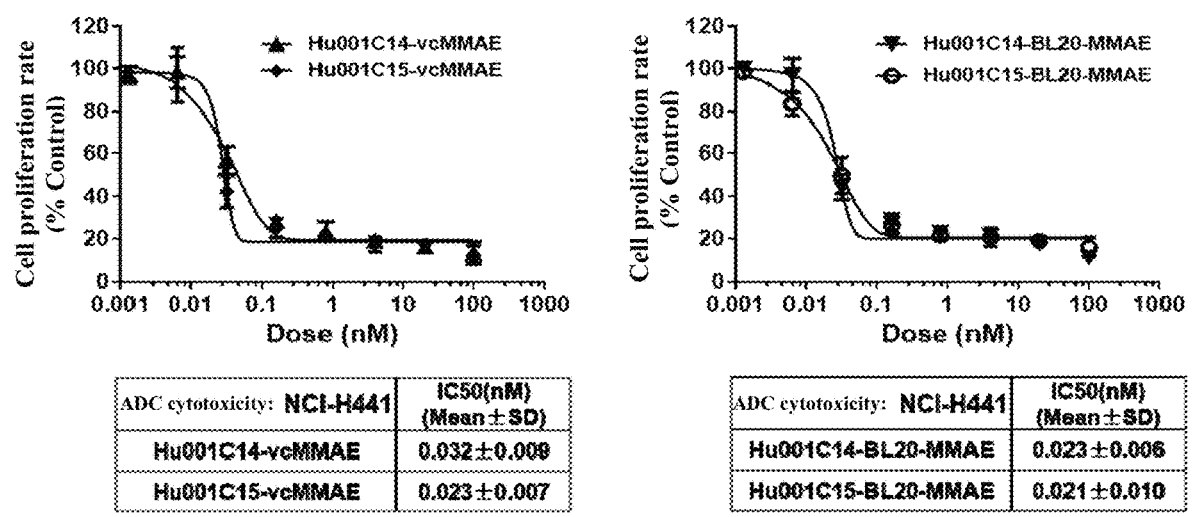
FIG. 54 shows the detection result of the inhibitory activity of the CD73 antibody-drug conjugate on the proliferation of lung cancer cell NCI-H441.
Figure 55:
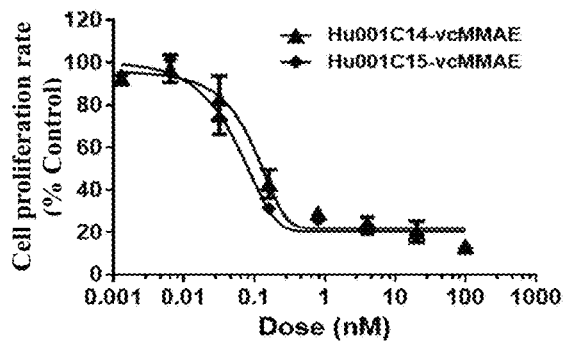
FIG. 55 shows the detection result of the inhibitory activity of the CD73 antibody-drug conjugate on the proliferation of lung cancer cell NCI-H292.
Figure 55:
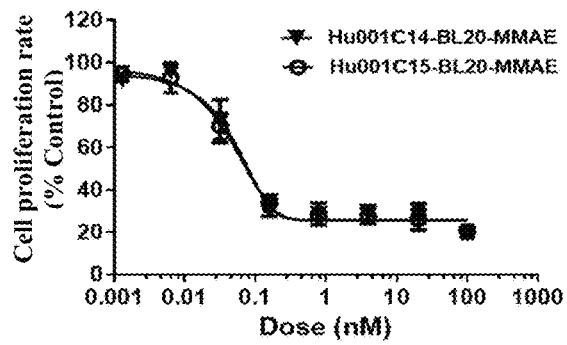
Figure 56:
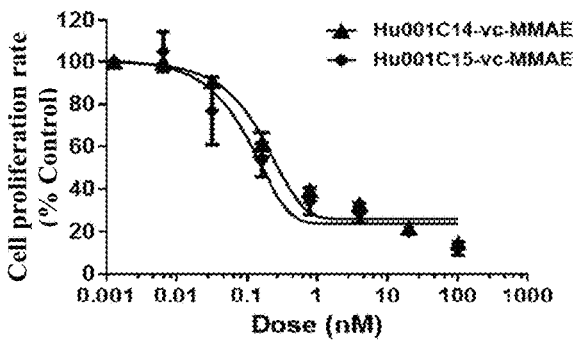
FIG. 56 shows the detection result of the inhibitory activity of the CD73 antibody-drug conjugate on the proliferation of triple negative breast cancer cell MDA-MB-231.
Figure 56:
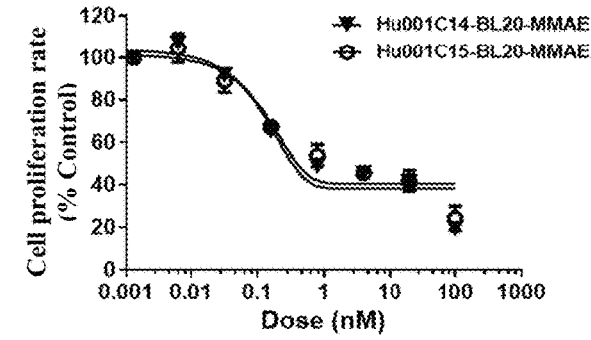
Figure 57:
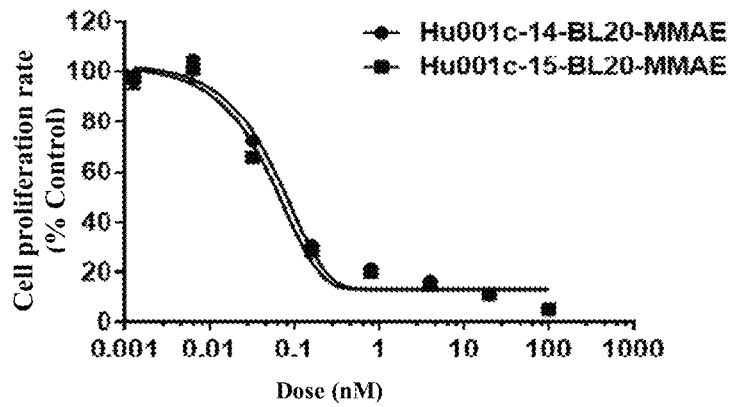
FIG. 57 shows the detection result of the inhibitory activity of the CD73 antibody-drug conjugate on the proliferation of lung cancer cell PC9.
Figure 58:
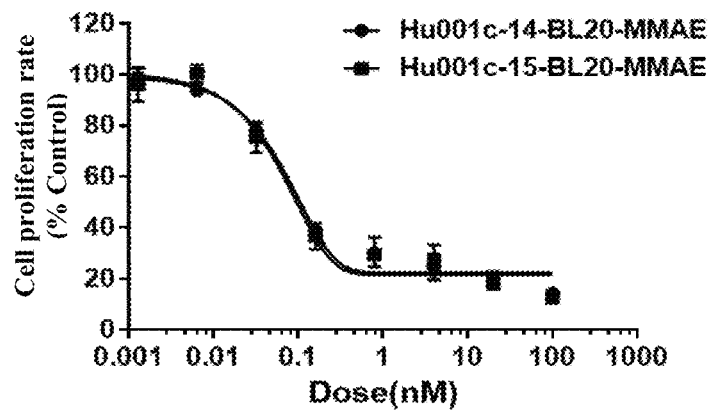
FIG. 58 shows the detection result of the inhibitory activity of the CD73 antibody-drug conjugate on the proliferation of lung cancer cell HCC827.
Figure 59:
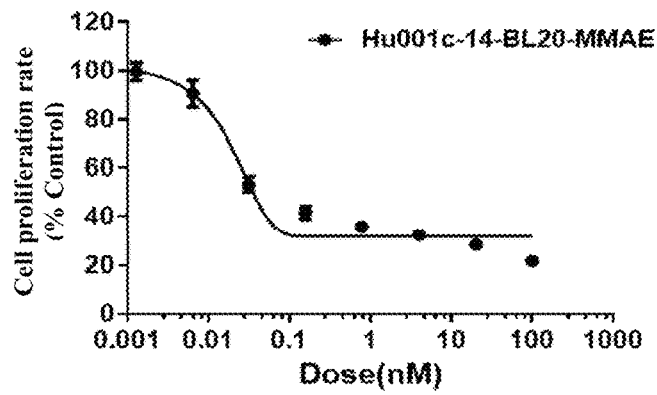
FIG. 59 shows the detection result of the inhibitory activity of the CD73 antibody-drug conjugate on the proliferation of lung cancer cell NCI-H1975.

As shown in FIG. 50, CD73-ADCs did not significantly inhibit the proliferation of CD73-low-expression cell MDA-MB-453, but showed strong cell proliferation inhibition on all of CD73-high-expression cells: Calu-1 (FIG. 51), U87MG (FIG. 52), Calu-6 (FIG. 53), NCI-H441 (FIG. 54), NCI-H292 (FIG. 55), MDA-MB-231 (FIG. 56), PC9 (FIG. 57), HCC827 (FIG. 58), and NCI-H1975 (FIG. 59).

Figure 60:
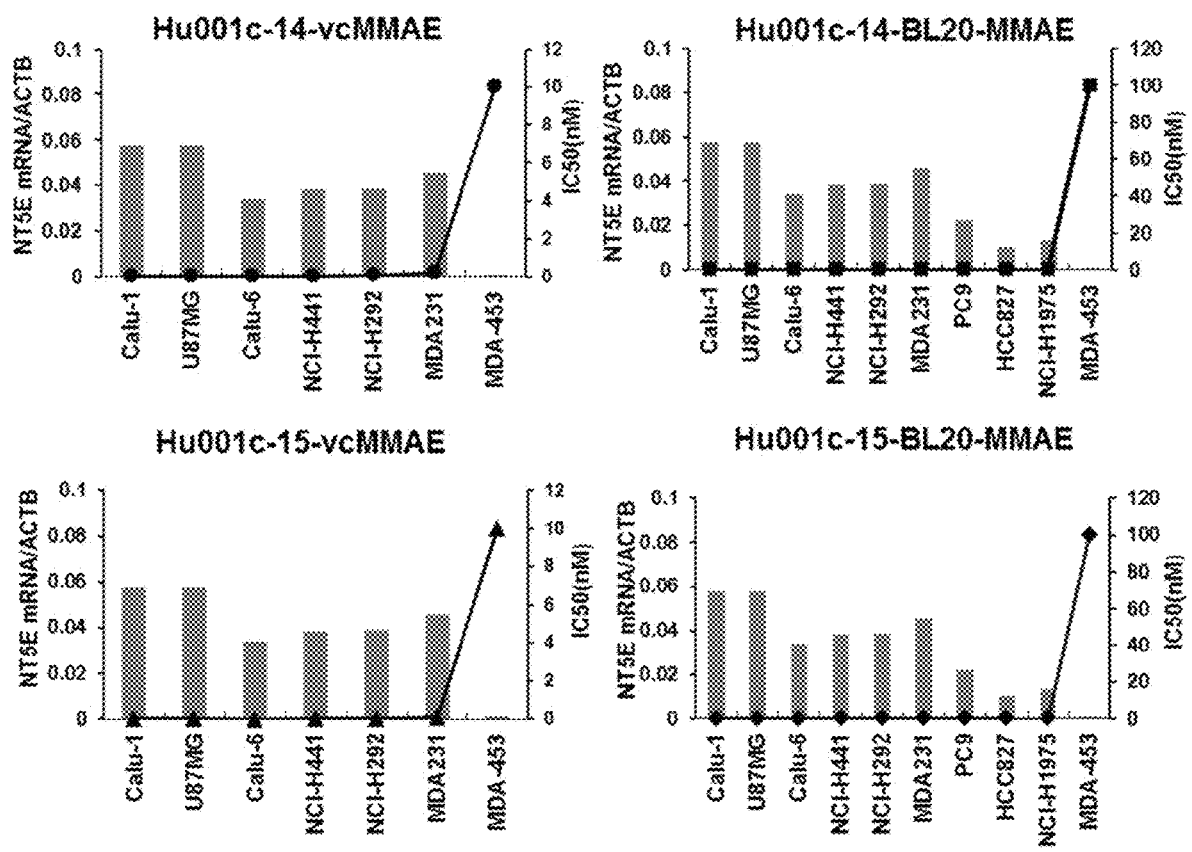
FIG. 60 shows that the cytotoxic activity (IC$_{50}$ value) of the CD73-drug conjugate is directly related to the CD73 expression level in the tested cells, showing target-specific cytotoxicity.

In general, the cytotoxicity of CD73-ADC ($IC_{50}$ value) indicated that the cytotoxic activity of the CD73-drug conjugate was directly related to the CD73 expression level of the tested cells, so it was judged as CD73 target-specific cytotoxicity (FIG. 60). Table-6 summarizes the $IC_{50}$ values of some cells in the proliferation inhibition test.

positive T lymphocytes were sorted using a sorting kit (Supplier: Stemcell, Cat #1795), and labeled with fluorescence. The pre-prepared fluorescent dye CFSE (carboxyfluorescein succinimidyl ester) was added into the cell suspension with a final concentration of 2.5 µM, incubated at 37° C. for 5 min, and washed with PBS for 3 times before being used for the experiment.

Figure 61:
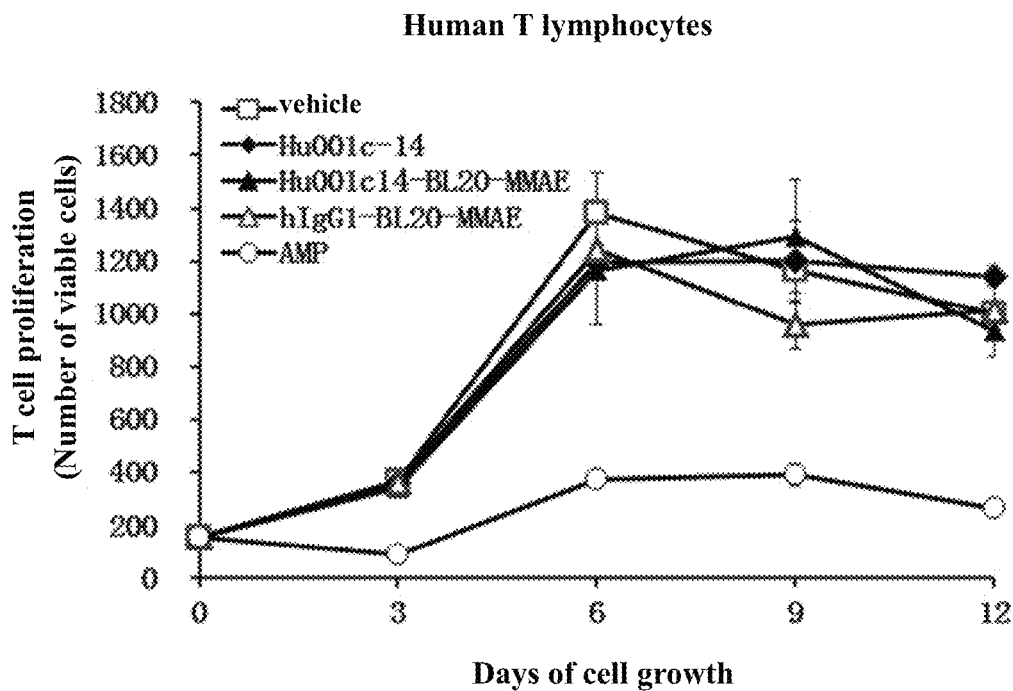
FIG. 61 shows the growth situation of human T lymphocytes (obtained from CD3$^+$ sorting) treated with CD73 antibody, antibody-drug conjugate (both of 10 nM), or AMP (0.3 mM). At a selected time point, the number of viable cells was read by FACS, and the growth curve was drawn.

First, the effect on T cell proliferation curve was observed. CFSE-labeled T cells were spread into a 96-well plate (5000 cells/well), the vehicle (buffer), CD73 antibody, CD73-ADC, control hIgG1-ADC (all was 10 nM) were added, or 0.3 mM adenosine monophosphate (AMP) was added. Using a Fluorescence Activated Cell Sorter (FACS), the numbers of viable cells on the 3rd, 6th, 9th and 12th day after culture were read and counted, and the growth curve was drawn. As shown in FIG. 61, compared with the vehicle and hIgG1-BL20-MMAE, 10 nM Hu001c14-BL20-MMAE did not significantly change the proliferation curve of T cells. However, consistent with expectation, AMP significantly reduced the proliferation rate of T cells.

Figure 62:
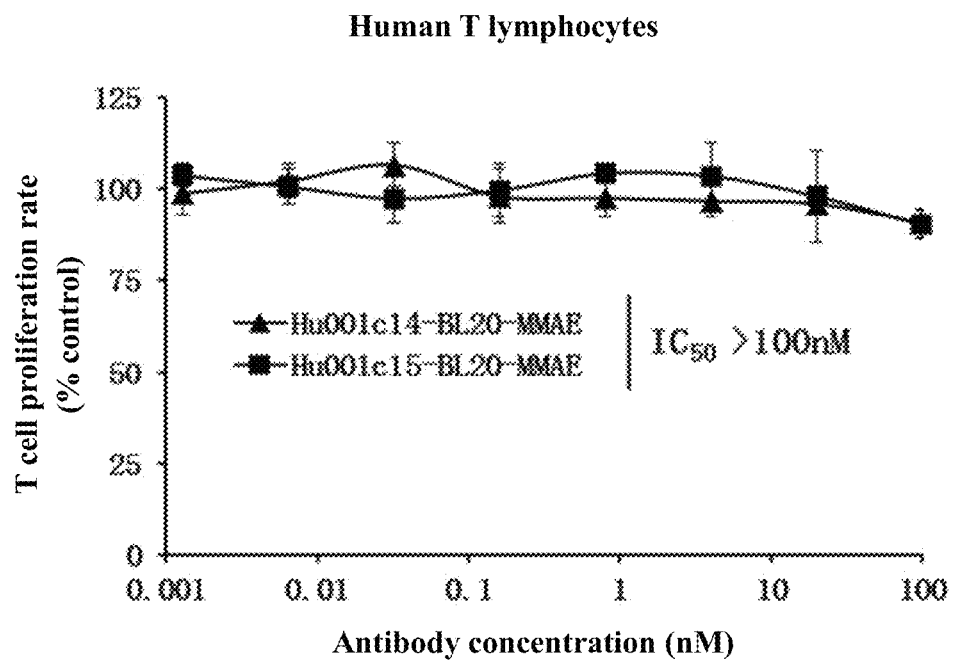
FIG. 62 shows the number of viable cells in a fixed volume which were read after incubating human T lymphocytes with different concentrations of CD73 antibody-drug conjugates for 5 days, and the inhibition curve was plotted based on the proliferation rate (relative to the vehicle/buffer).

Then in another set of experiments, CFSE-labeled T cells were spread into a 96-well plate ($2\times10^4$ cells/well), and CD73-ADC (the final concentration was 100 nM-0.00128 nM, n=3) diluted in a gradient or a control vehicle was added into each well. The number of viable cells after 5 days of culture was read using FACS, and a dose curve was drawn to calculate the $IC_{50}$ value. As shown in FIG. 62, Hu001c14-BL20-MMAE and Hu001c15-BL20-MMAE showed no obvious side effects in the tested concentration range ($IC_{50}$>100 nM).

Example 27 In Vivo Anti-Tumor Activity of CD73-ADC

200 µL of cell suspension containing $5\times10^6$ U87MG, NCI-H441, or NCI-H292 was inoculated subcutaneously into the back of immunodeficient mice (Balb/c, nude), respectively. When the tumor volume grew to 100-300 mm³, the mice were randomly grouped according to tumor size and nude mouse body weight (n=8), and administrated once a week through the tail vein for a total of 2 weeks in a dose

TABLE 6

In vitro anti-tumor activity of CD73 humanized antibody-drug conjugate

| Name of antibody-drug conjugate | Cell proliferation inhibition rate $IC_{50} \pm SD$ (nM) | | | | | | |
|---|---|---|---|---|---|---|---|
| | MDA-MB-453 | Calu-1 | U87MG | Calu-6 | NCI-H441 | NCI-H292 | MDA-MB-231 |
| Hu001C14-vcMMAE | >10 | 0.053 ± 0.005 | 0.023 ± 0.007 | 0.024 ± 0.0006 | 0.032 ± 0.009 | 0.094 ± 0.025 | 0.19 ± 0.038 |
| Hu001C14-BL20E-MMAE | >100 | 0.037 ± 0.013 | 0.020 ± 0.005 | 0.018 ± 0.007 | 0.023 ± 0.006 | 0.051 ± 0.007 | 0.20 ± 0.011 |
| Hu001C15-vcMMAE | >10 | 0.027 ± 0.006 | 0.017 ± 0.005 | 0.012 ± 0.0004 | 0.023 ± 0.007 | 0.053 ± 0.005 | 0.086 ± 0.035 |
| Hu001C15-BL20E-MMAE | >100 | 0.037 ± 0.007 | 0.020 ± 0.005 | 0.020 ± 0.007 | 0.021 ± 10.010 | 0.045 ± 10.009 | 0.22 ± 10.078 |

Example 26 Effect of CD73-ADC on Proliferation of Human T Lymphocytes

Human peripheral blood mononuclear cell (PBMC) cryopreservation tubes were provided by Jiangsu Xidier Biotechnology Co., Ltd. First, PBMC was resuscitated and cultured for 3-4 days using a medium containing 500 ng/mL CD3/CD28 antibody and 100 IU/mL IL-2, and then CD3- of 5 mg/kg, 3 mg/kg, 1 mg/kg, 0.3 mg/kg, respectively. hIgG (hIgG1-MMAE) was set as a negative control, and 15 mg/kg docetaxel (Docetaxel) was set as a positive control. The tumor volume and nude mice body weight were measured 2-3 times a week and recorded to draw a tumor growth curve. The calculation formula for tumor volume (V) was: $V=\frac{1}{2}\times a \times b^2$, wherein a and b represent the length and width of the tumor, respectively.

The in vivo anti-tumor activity results of three preferred humanized CD73-ADCs: Hu001c14-BL20-MMAE, Hu001c14-vcMMAE, and Hu001c15-BL20-MMAE are shown in FIG. 63 to FIG. 67, respectively.

Figure 63:
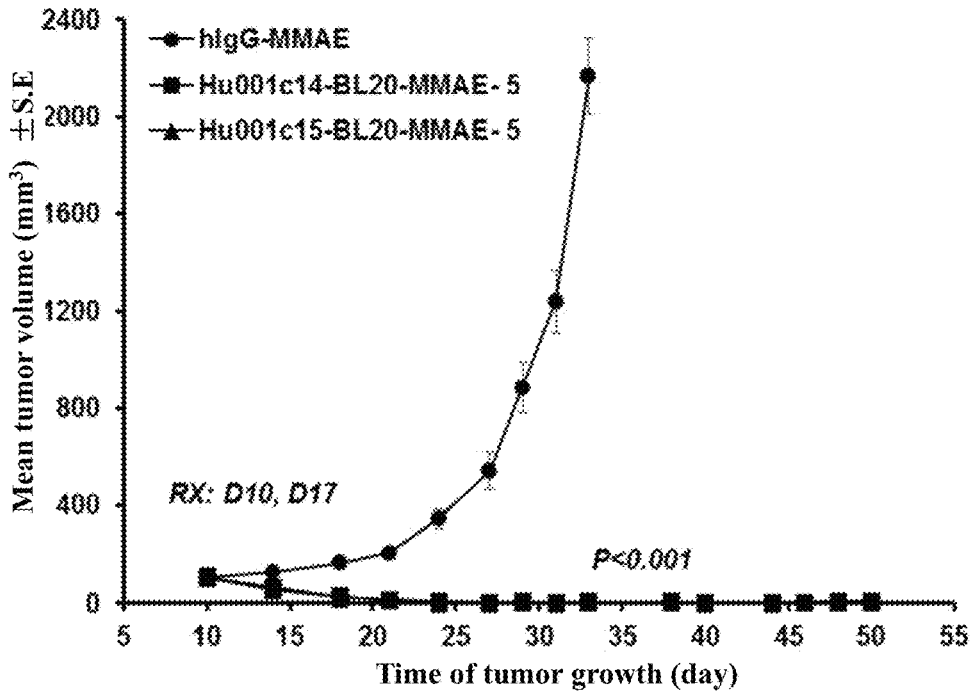
FIG. 63 shows the anti-tumor activity of CD73 antibody-drug conjugate in vivo. U87MG glioma cells with CD73 high expression were inoculated subcutaneously in the back of nude mice. Tumor volume was measured on the 10th day and the mice were randomly divided into groups (n=8). Intravenous administration was performed twice in total (10th and 17th days) at a dose of 5 mg/kg.

As shown in FIG. 63, Hu001c14-BL20-MMAE and Hu001c15-BL20-MMAE at 5 mg/kg could completely inhibit the growth of CD73-high-expression U87MG tumors. The tumors regressed, and no tumor regrowth was observed after drug administration was stopped for more than 30 days.

Figure 64:
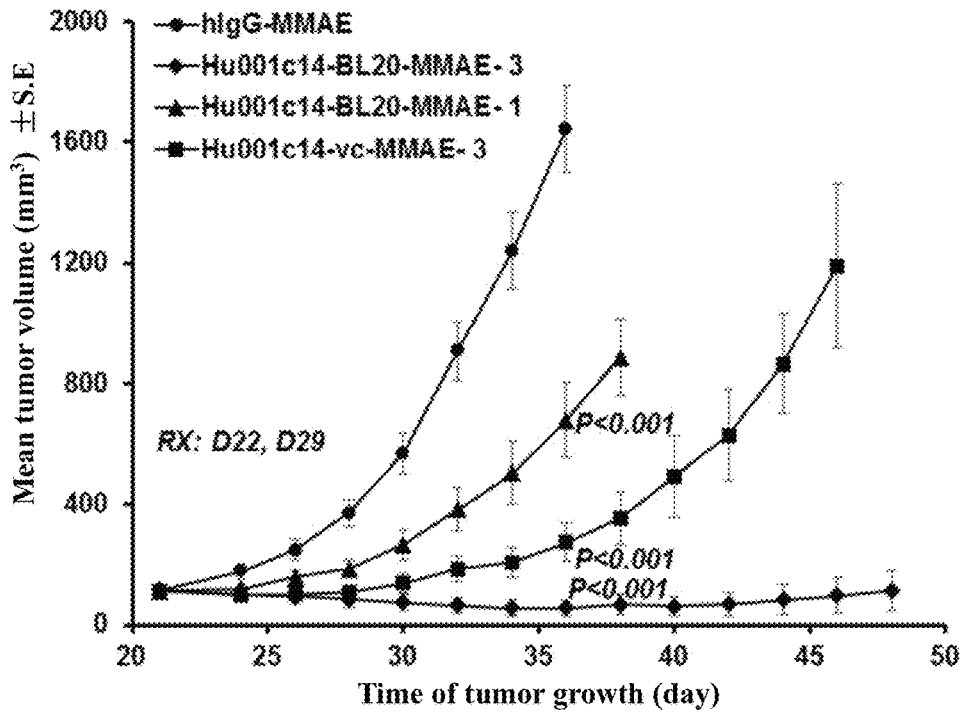
FIG. 64 shows the anti-tumor activity of CD73 antibody-drug conjugate in vivo. The mice were randomly divided into groups (n=8) on the 22nd day after inoculation with U87MG glioma cells. Intravenous administration was performed twice in total (22nd and 29th days) with Hu001c14-BL20-MMAE (3 mg/kg, 1 mg/kg); Hu001c14-vc-MMAE (3 mg/kg).

As shown in FIG. 64, in the U87MG tumor model, Hu001c14-BL20-MMAE showed a dose-related therapeutic effect when administered at 3 mg/kg and 1 mg/kg. And at a same dose of 3 mg/kg, Hu001c14-BL20-MMAE showed stronger anti-tumor activity than Hu001c14-vcMMAE, indicating that the BL20-MMAE linker was more superior.

Figure 65:
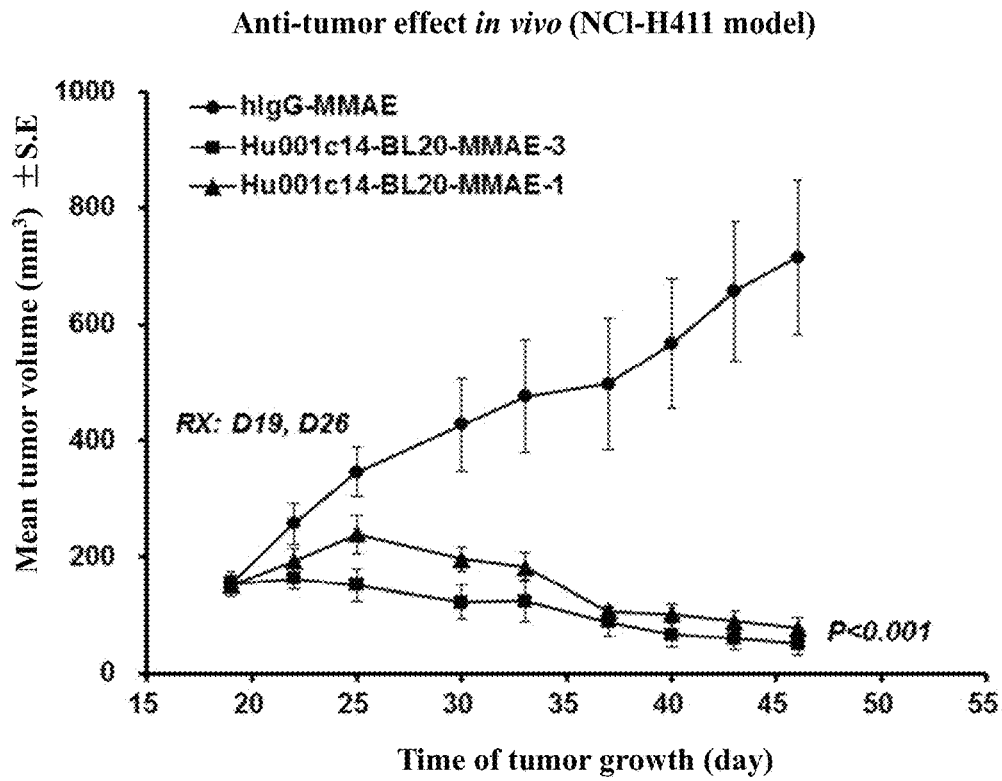
FIG. 65 shows the anti-tumor activity of CD73 antibody-drug conjugate in vivo. The non-small cell lung cancer NCI-H441 cells with CD73 high expression were inoculated subcutaneously in the back of nude mice. The mice were randomly divided into groups on 19th day (n=8). Intravenous administration was performed twice in total (19th and 26th days) at a dose of 3 mg/kg, 1 mg/kg.

As shown in FIG. 65, in the NCI-H441 tumor model, Hu001c14-BL20-MMAE could cause significant tumor regression after the administration of 3 mg/kg and 1 mg/kg, indicating that NCI-H441 tumor was highly sensitive to CD73-ADC.

Figure 66:
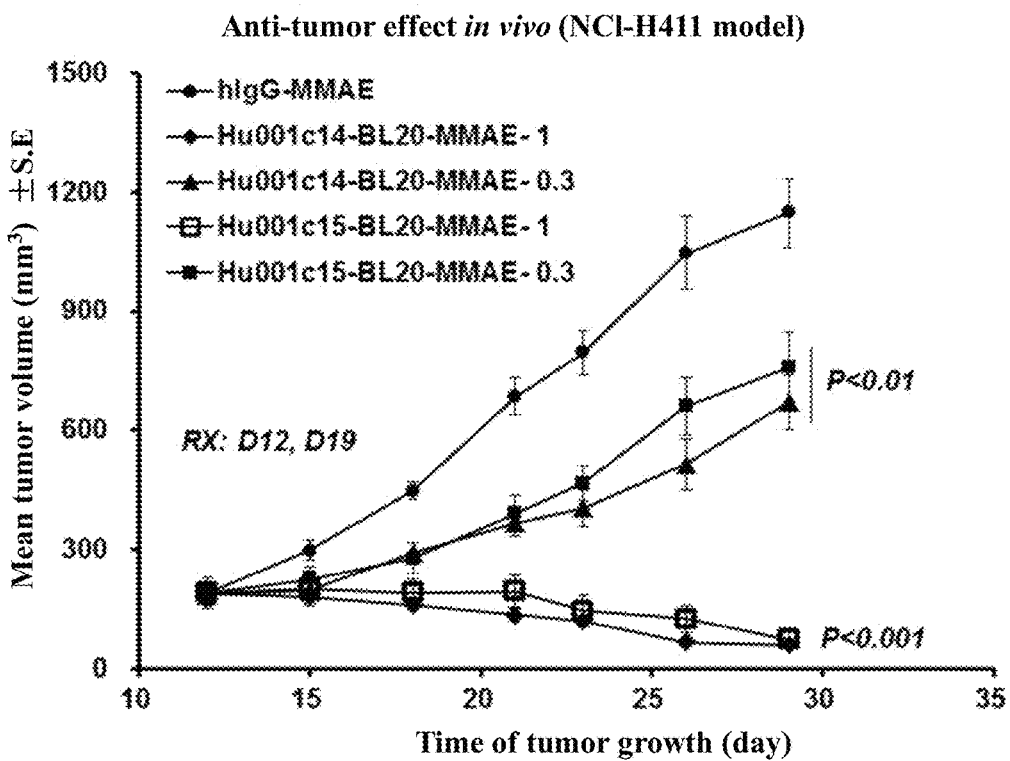
FIG. 66 shows the anti-tumor activity of CD73 antibody-drug conjugate in vivo. NCI-H441 cells were inoculated and the mice were randomly divided into groups on 12th day (n=8). Intravenous administration was performed twice in total (12th and 19th days) at a dose of 1 mg/kg, 0.3 mg/kg, respectively.

As shown in FIG. 66, in the NCI-H441 tumor model, Hu001c14-BL20-MMAE and Hu001c15-BL20-MMAE could cause significant tumor regression after the administration of 1 mg/kg, and still had significant anti-tumor activity after the administration of 0.3 mg/kg, which further confirmed the high sensitivity of NCI-H441 tumor to CD73-ADC.

Figure 67:
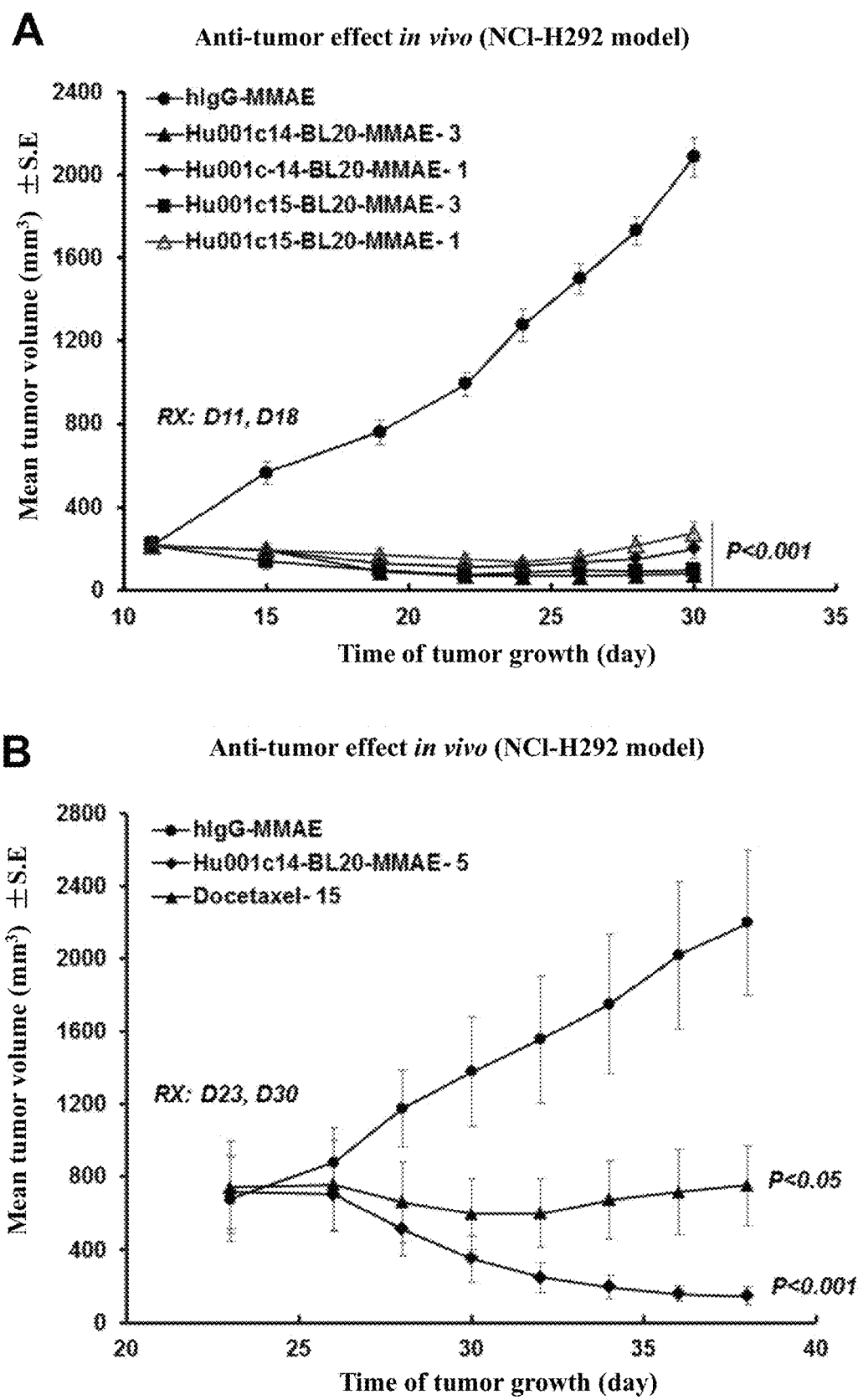
FIG. 67 shows the anti-tumor activity of CD73 antibody-drug conjugate in vivo. The non-small cell lung cancer NCI-H292 cells with CD73 high expression were inoculated subcutaneously in the back of nude mice.

As shown in FIG. 67, in the NCI-H292 tumor model, Hu001c14-BL20-MMAE and Hu001c15-BL20-MMAE could completely inhibit tumor growth after the administration of 3 mg/kg and 1 mg/kg (FIG. 67A). In another independent tumor regression experiment, the administration was performed when the tumor volume reached about 700 mm$^3$, the therapeutic effect of 5 mg/kg Hu001c14-BL20-MMAE was significantly better than that of 15 mg/kg Docetaxel (FIG. 67B).

Example 28 Inhibition of CD73 Humanized Antibody on Cynomolgus Monkey CD73 Enzyme Activity Carbon-terminal polyhistidine-labeled recombinant cynomolgus monkey CD73 enzyme was prepared and obtained using cynomolgus CD73/NT5E extracellular region sequence (EHH53214.1; Met1-Lys547), and the specific amino acid sequence is as shown in SEQ ID NO. 48.

The humanized antibodies in Table 2 were serially diluted, and the effect of the antibodies on the enzyme activity of recombinant cynomolgus monkey CD73 was determined according to the method of Example 5.

Figure 68:
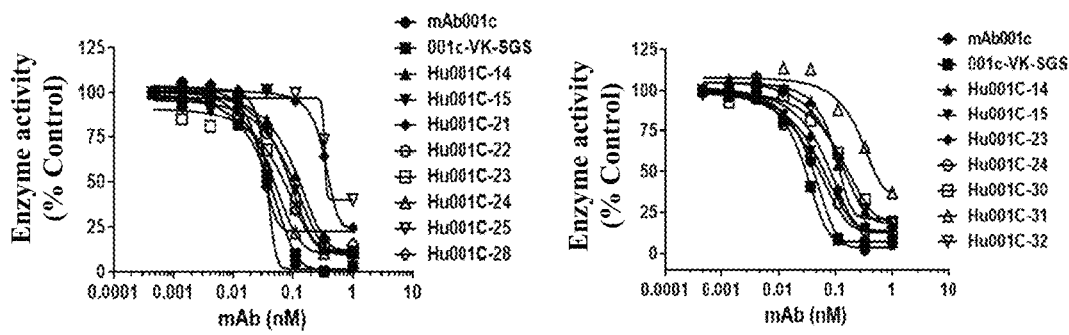
FIG. 68 shows the detected inhibitory activity ($IC_{50}$) of the Hu001c series of humanized antibodies on the catalytic function of recombinant cynomolgus monkey CD73.
Figure 69:
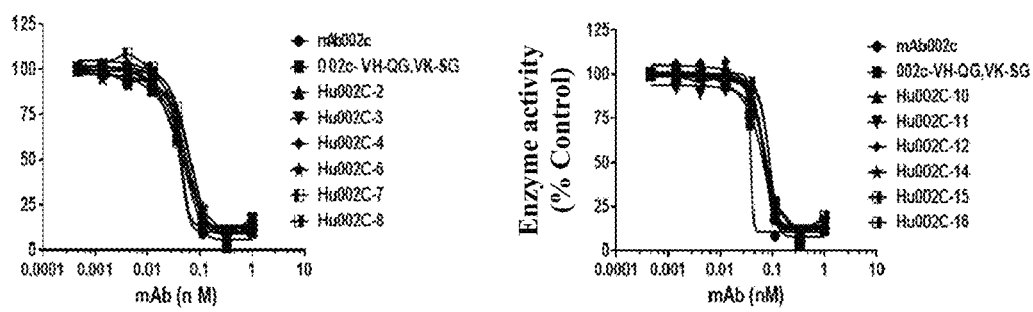
FIG. 69 shows the detected inhibitory activity ($IC_{50}$) of the Hu002c series of humanized antibodies on the catalytic function of recombinant cynomolgus monkey CD73.

The experimental results are shown in FIG. 68 and FIG. 69. The two groups of humanized antibodies had expected inhibitory effect on the cynomolgus monkey CD73 enzyme. The range of the IC$_{50}$ value was approximately the same as the inhibitory activity on the human CD73 enzyme.

Example 29 Safety Experiment of CD73-ADC Against Cynomolgus Monkeys

Two female cynomolgus monkeys were administered a single intravenous infusion of 3 mg/kg Hu001c14-vcMMAE (Test substance number is FD114-ADC), followed by continuous observation for 21 days, and another intravenous infusion of 6 mg/kg Hu001c14-vcMMAE was administrated on the 22nd day (Test substance number is FD114-ADC), followed by continuous observation for 21 days, and then (after 42 days in total) the cynomolgus monkeys were euthanized and dissected. During the experiment, the following indexes were evaluated: cage observation, body weight, food consumption, hematology, blood coagulation, plasma biochemistry, immunophenotype (only detected on the 21st day after administration of 6 mg/kg), naked eye morphology observation, and biological analysis.

The results showed that the animals had no obvious drug-related changes in clinical symptoms, body weight, food consumption and naked eye morphology at each dose. Hematological indexes: on the 7th day after the administration of 3 and 6 mg/kg, there was a slight decrease in RBC, HGB and HCT, and a significant decrease in RET, WBC and their classification (mainly NEUT, MONO and EOS); on the 14th and 21st days after the administration of 3 mg/kg, there was still a slight decrease in RBC, HGB and HCT; and on the 14th and/or 21st day after the administration of 6 mg/kg, the above changes were completely recovered or showed a trend of recovery (FIG. 70). Blood coagulation index: on the 14th day after the administration of 3 mg/kg, the FIB of 2/2 animals temporarily and slightly increased; after the administration of 6 mg/kg, the FIB of 1/2 animals increased slightly; and the recovery trend could be observed on the 21st day after the administration (FIG. 71). Plasma biochemical index: there were no obvious drug-related plasma biochemical changes after administration of 3 and 6 mg/kg (FIG. 72). Immunophenotype: on the 21st day after the administration of 6 mg/kg, 1/2 animals showed a slight increase in CD3+CD4+ and a slight decrease in CD3-CD20+. In general, under the conditions of this experiment, cynomolgus monkeys were infused intravenously with 3 and 6 mg/kg of Hu001c14-vcMMAE in a single dose increment, and the animals were well tolerated. The decrease in quantity of erythroid/granulocyte cells and the increase in fibrinogen were main observation after the administration, and could be recovered after drug administration was stopped. The maximum tolerated dose (MTD) was greater than 6 mg/kg.

In summary, the study of CD73-ADC related examples clearly shows:

1. CD73 humanized antibody-drug conjugates Hu001c14-vcMMAE, Hu001c15-vcMMAE, Hu001c14-BL20-MMAE and Hu001c15-BL20-MMAE all have good CD73-specific tumor cell killing activity, i.e. these ADCs have a strong inhibitory effect on the proliferation of CD73-high-expression tumor cells, but have no obvious toxicity to the proliferation of CD73-low-expression cells.

2. CD73 humanized antibody-drug conjugates Hu001c14-BL20-MMAE and Hu001c15-BL20-MMAE have no obvious toxicity against the cell proliferation of normal human T lymphocytes.

3. Compared with Hu001c14-vcMMAE and Hu001c15-vcMMAE of traditional mcVC-PAB cross-linking technology, Hu001c14-BL20-MMAE and Hu001c15-BL20-MMAE prepared by using the novel linker of the present invention have equivalent or higher anti-tumor activity (Table-6).

4. Based on the more excellent uniformity and stability of the new linker, both of Hu001c14-BL20-MMAE and Hu001c15-BL20-MMAE show lower non-specific (due to the falling off of target head) toxicity and side effects. For example, the cytotoxic IC$_{50}$ against CD73-low-expression MDA-MB-453 is further increased (FIG. 50, Table-6).

5. Based on the preliminary toxicological experiment of Hu001c14-vcMMAE administrated intravenously to cynomolgus monkeys (3 mg/kg, 6 mg/kg), CD73-ADC has shown expected and controllable safety, and so it has the potential for clinical application.

All literatures mentioned in the present application are incorporated herein by reference, as though each one is individually incorporated by reference. In addition, it should also be understood that, after reading the above teachings of the present invention, those skilled in the art can make various changes or modifications, and these equivalents also fall in the scope of claims as defined in the appended claims.

```
Antibody sequence
SEQ ID NO. 1: mAb001 HCDR1
NYYIY

SEQ ID NO. 2: mAb001 HCDR2
WIYPGNLNIKYNEKFKG

SEQ ID NO. 3: mAb001 HCDR3
DDNYAWFAY

SEQ ID NO. 4: mAb001 LCDR1
KASQDVSTAVA

SEQ ID NO. 5: mAb001 LCDR2
WTNTRHT

SEQ ID NO. 6: mAb001 LCDR3
QQHYSTPFT

SEQ ID NO. 7: mAb001-VH
QVQLQQSGPELVKPGASVRISCKTSGYTFTNYYIYWVKQRPGQGLEWIGW

IYPGNLNIKYNEKFKGKSTLTADKSSSTAFMQLSSLTSEDSAVYFCARDD

NYAWFAYWGQGTLVTVSS

SEQ ID NO. 8: mAb001-VL
DIVMTQSHKFMSTSIGDRVSITCKASQDVSTAVAWYQQKPGQSPKLLIYW

TNTRHTGVPDRFTGNTSGTEHTLTISSVQAEDLALYYCQQHYSTPFTFGS

GTTLEIK

SEQ ID NO. 9: mAb001-VL-SGS
DIVMTQSHKFMSTSIGDRVSITCKASQDVSTAVAWYQQKPGQSPKLLIYW

TNTRHTGVPDRFTGSGSGTEHTLTISSVQAEDLALYYCQQHYSTPFTFGS

GTTLEIK

SEQ ID NO. 10: mAb002 HCDR1
SYWMH

SEQ ID NO. 11: mAb002 HCDR2
EINPSNGRSNYNEKFKS

SEQ ID NO. 12: mAb002 HCDR3
RGVSGNYFDY

SEQ ID NO. 13: mAb002 LCDR1
KASQDINTYLS

SEQ ID NO. 14: mAb002 LCDR2
RSNILVD

SEQ ID NO. 15: mAb002 LCDR3
LQYDEFPYT

SEQ ID NO. 16: mAb002-VH
QVQLQQPGAELVKPGASVRLSCKASGYTLTSYWMHWVKKRPGQGLEWIGE

INPSNGRSNYNEKFKSKATLTVDRSSSTVYMQLGSLTSEDSAVYYCARRG

VSGNYFDYWGQGTTLTVSS

SEQ ID NO. 17: mAb002-VH-QG
QVQLQQPGAELVKPGASVRLSCKASGYTLTSYWMHWVKKRPGQGLEWIGE

INPSQGRSNYNEKFKSKATLTVDRSSSTVYMQLGSLTSEDSAVYYCARRG

VSGNYFDYWGQGTTLTVSS

SEQ ID NO. 18: mAb002-VH-NA
QVQLQQPGAELVKPGASVRLSCKASGYTLTSYWMHWVKKRPGQGLEWIGE

INPSNARSNYNEKFKSKATLTVDRSSSTVYMQLGSLTSEDSAVYYCARRG

VSGNYFDYWGQGTTLTVSS

SEQ ID NO. 19: mAb002-VL
DIKMTQSPSSMYASLGERVTMTCKASQDINTYLSWFQQKPGKSPKTLIYR

SNILVDGVPSRFSGSRSGQDYYLTITSLEYEDMGIYYCLQYDEFPYTFGG

GTKLELK

SEQ ID NO. 20: mAb002-VL-SG
DIKMTQSPSSMYASLGERVTMTCKASQDINTYLSWFQQKPGKSPKTLIYR

SNILVSGVPSRFSGSRSGQDYYLTITSLEYEDMGIYYCLQYDEFPYTFGG

GTKLELK

SEQ ID NO. 21: mAb004 HCDR1
DYNMD

SEQ ID NO. 22: mAb004 HCDR2
DINPNNGGSVYNQKFKG

SEQ ID NO. 23: mAb004 HCDR3
ITGTGYWSFDV

SEQ ID NO. 24: mAb004 LCDR1
RASENIYSNLA

SEQ ID NO. 25: mAb004 LCDR2
GATNLAE

SEQ ID NO. 26: mAb004 LCDR3
QHFWGIPWT

SEQ ID NO. 27: mAb004-VH
EVQLQQSGPELVKPGASVKIPCKASGYTFTDYNMDWVKQSHGKSLEWIGD

INPNNGGSVYNQKFKGKATLTVDKSSSTAYMELRSLTSEDTAVYYCGRIT

GTGYWSFDVWGTGTTVTVSP

SEQ ID NO. 28: mAb004-VH-QG
EVQLQQSGPELVKPGASVKIPCKASGYTFTDYNMDWVKQSHGKSLEWIGD

INPNQGGSVYNQKFKGKATLTVDKSSSTAYMELRSLTSEDTAVYYCGRIT

GTGYWSFDVWGTGTTVTVSP

SEQ ID NO. 29: mAb004-VH-NA
EVQLQQSGPELVKPGASVKIPCKASGYTFTDYNMDWVKQSHGKSLEWIGD

INPNNAGSVYNQKFKGKATLTVDKSSSTAYMELRSLTSEDTAVYYCGRIT

GTGYWSFDVWGTGTTVTVSP

SEQ ID NO. 30: mAb004-VL
DIQMTQSPASLSVSVGETVTITCRASENIYSNLAWYQQKQGKSPQLLVYG

ATNLAEGVPSRFSGSGLGTQYSLKISSLQSEDFGSYYCQHFWGIPWTFGG

GTKLEIK

SEQ ID NO. 31: mAb001-VH_HuG.3
QVQLVQSGAEVKKPGASVKVSCKTSGYTFTNYYIYWVRQAPGQRLEWMGW

IYPGNLNIKYNEKFKGRVTITADTSASTAYMELSSLRSEDTAVYYCARDD

NYAWFAYWGQGTLVTVSS

SEQ ID NO. 32: mAb001-VH_HuG.5
QVQLVQSGAEVKKPGASVKVSCKASGYTFTNYYIYWVRQAPGQRLEWIGW

IYPGNLNIKYNEKFKGRVTITADKSASTAYMELSSLRSEDTAVYYCARDD

NYAWFAYWGQGTLVTVSS
```

SEQ ID NO. 33: mAb001-VH_HuG.6
QVQLVQSGAEVKKPGASVKVSCKASGYTFTNYYIYWVKQRPGQRLEWIGW
IYPGNLNIKYNEKFKGRVTITADKSASTAYMELSSLRSEDTAVYYCARDD
NYAWFAYWGQGTLVTVSS

SEQ ID NO. 34: mAb001-VH_HuG.7
QVQLVQSGAEVKKPGASVKVSCKASGYTFTNYYIYWVKQRPGQGLEWIGW
IYPGNLNIKYNEKFKGRVTITADKSASTAYMELSSLRSEDTAVYYCARDD
NYAWFAYWGQGTLVTVSS

SEQ ID NO. 35: mAb001-VH_HuG.8
QVQLVQSGAEVKKPGASVKVSCKTSGYTFTNYYIYWVKQRPGQGLEWIGW
IYPGNLNIKYNEKFKGRVTITADKSASTAYMELSSLRSEDTAVYYCARDD
NYAWFAYWGQGTLVTVSS

SEQ ID NO. 36: mAb001-VK_HuG.1
DIQMTQSPSSLSASVGDRVTITCKASQDVSTAVAWYQQKPGKAPKLLIYW
TNTRHTGVPSRFSGSGSGTDHTLTISSLQPEDFATYYCQQHYSTPFTFGQ
GTKLEIK

SEQ ID NO. 37: mAb001-VK_HuG.2
DIQMTQSPSSLSASVGDRVTITCKASQDVSTAVAWYQQKPGKSPKLLIYW
TNTRHTGVPSRFSGSGSGTDHTLTISSLQPEDFATYYCQQHYSTPFTFGQ
GTKLEIK

SEQ ID NO. 38: mAb002-VH_HuG0
QVQLVQSGAEVKKPGASVKVSCKASGYTLTSYWMHWVRQAPGQGLEWMGE
INPSQGRSNYNEKFKSRVTMTRDTSTSTVYMELSSLRSEDTAVYYCARRG
VSGNYFDYWGQGTLVTVSS

SEQ ID NO. 39: mAb002-VH_HuG1
QVQLVQSGAEVKKPGASVKVSCKASGYTLTSYWMHWVRQAPGQGLEWIGE
INPSQGRSNYNEKFKSRVTLTVDRSTSTVYMELSSLRSEDTAVYYCARRG
VSGNYFDYWGQGTLVTVSS

SEQ ID NO. 40: mAb002-VH_HuG2
QVQLVQSGAEVKKPGASVKVSCKASGYTLTSYWMHWVRQAPGQGLEWIGE
INPSQGRSNYNEKFKSKVTLTVDRSTSTVYMELSSLRSEDTAVYYCARRG
VSGNYFDYWGQGTLVTVSS

SEQ ID NO. 41: mAb002-VH_HuG3
QVQLVQSGAEVKKPGASVKVSCKASGYTLTSYWMHWVKKAPGQGLEWIGE
INPSQGRSNYNEKFKSKVTLTVDRSTSTVYMELSSLRSEDTAVYYCARRG
VSGNYFDYWGQGTLVTVSS

SEQ ID NO. 42: mAb002-VK_HuG1
DIQMTQSPSSLSASVGDRVTITCKASQDINTYLSWFQQKPGKAPKSLIYR
SNILVSGVPSRFSGSGSGQDYTLTISSLQPEDFATYYCLQYDEFPYTFGQ
GTKLEIK

SEQ ID NO. 43: mAb002-VK_HuG2
DIQMTQSPSSLSASVGDRVTITCKASQDINTYLSWFQQKPGKSPKSLIYR
SNILVSGVPSRFSGSGSGQDYTLTISSLQPEDFATYYCLQYDEFPYTFGG
GTKLEIK

SEQ ID NO. 44: mAb002-VK_HuG3
DIQMTQSPSSLSASVGDRVTITCKASQDINTYLSWFQQKPGKSPKSLIYR
SNILVSGVPSRFSGSGSGQDYTLTISSLQPEDFAIYYCLQYDEFPYTFGG
GTKLEIK

SEQ ID NO. 45: mAb001-VH_HuG.9
QVQLVQSGAEVKKPGASVKVSCKASGYTFTNYYIYWVRQAPGQRLEWIGW
IYPGNLNIKYNEKFKGRSTLTADKSASTAYMELSSLRSEDTAVYYCARDD
NYAWFAYWGQGTLVTVSS

SEQ ID NO. 46: mAb001-VH_HuG.10
QVQLVQSGAEVKKPGASVKVSCKASGYTFTNYYIYWVKQRPGQRLEWIGW
IYPGNLNIKYNEKFKGRSTLTADKSASTAYMELSSLRSEDTAVYYCARDD
NYAWFAYWGQGTLVTVSS

SEQ ID NO. 47: mAb001-VK_HuG.0
DIQMTQSPSSLSASVGDRVTITCKASQDVSTAVAWYQQKPGKAPKLLIYW
TNTRHTGVPSRFSGSGSGTDFTLTISSLQPEDFATYYCQQHYSTPFTFGQ
GTKLEIK

SEQ ID NO. 48: Human CD73-ECD
WELTILHTNDVHSRLEQTSEDSSKCVNASRCMGGVARLFTKVQQIRRAEP
NVLLLDAGDQYQGTIWFTVYKGAEVAHFMNALRYDAMALGNHEFDNGVEG
LIEPLLKEAKFPILSANIKAKGPLASQISGLYLPYKVLPVGDEVVGIVGY
TSKETPFLSNPGTNLVFEDEITALQPEVDKLKTLNVNKIIALGHSGFEMD
KLIAQKVRGVDVVVGGHSNTFLYTGNPPSKEVPAGKYPFIVTSDDGRKVP
VVQAYAFGKYLGYLKIEFDERGNVISSHGNPILLNSSIPEDPSIKADINK
WRIKLDNYSTQELGKTIVYLDGSSQSCRFRECNMGNLICDAMINNNLRHT
DEMFWNHVSMCILNGGGIRSPIDERNNGTITWENLAAVLPFGGTFDLVQL
KGSTLKKAFEHSVHRYGQSTGEFLQVGGIHVVYDLSRKPGDRVVKLDVLC
TKCRVPSYDPLKMDEVYKVILPNFLANGGDGFQMIKDELLRHDSGDQDIN
VVSTYISKMKVIYPAVEGRIKAHHHHHHHHHH SEQ ID NO. 49: MEDI9447 heavy chain variable
region (MEDI9447-VH)
EVQLLESGGGLVQPGGSLRLSCAASGFTFSSYAYSWVRQAPGKGLEWVSA
ISGSGGRTYYADSVKGRFTISRDNSKNTLYLQMNSLRAEDTAVYYCARLG
YGRVDEWGRGTLVTVSS SEQ ID NO. 50: MEDI9447 light chain variable
region (MEDI9447-VL)
QSVLTQPPSASGTPGQRVTISCSGSLSNIGRNPVNWYQQLPGTAPKLLIY
LDNLRLSGVPDRFSGSKSGTSASLAISGLQSEDEADYYCATWDDSHPGWT
FGGGTKLTVL

The invention claimed is:

1. An antibody, which binds to CD73, wherein the antibody comprises a heavy chain and a light chain,
wherein the heavy chain has a
heavy chain variable region comprising the following three complementarity determining regions (CDRs):
CDR1 as shown in SEQ ID NO. 10,
CDR2 as shown in SEQ ID NO. 11, and
CDR3 as shown in SEQ ID NO. 12; and
the light chain has a light chain variable region comprising the following three complementarity determining regions (CDRs):
CDR1' as shown in SEQ ID NO. 13,
CDR2' as shown in SEQ ID NO. 14, and
CDR3' as shown in SEQ ID NO. 15;
or
the heavy chain has a heavy chain variable region comprising the following three complementary determining regions (CDRs):
CDR1 as shown in SEQ ID NO. 1,
CDR2 as shown in SEQ ID NO. 2, and
CDR3 as shown in SEQ ID NO. 3; and
the light chain has a light chain variable region comprising the following three complementarity determining regions (CDRs):
CDR1' as shown in SEQ ID NO. 4,
CDR2' as shown in SEQ ID NO. 5, and
CDR3' as shown in SEQ ID NO. 6;
or
the heavy chain has a heavy chain variable region comprising the following three complementary determining regions (CDRs):
CDR1 as shown in SEQ ID NO. 21,
CDR2 as shown in SEQ ID NO. 22, and
CDR3 as shown in SEQ ID NO. 23; and/or the light chain has a light chain variable region comprising the following three complementarity determining regions (CDRs):
CDR1' as shown in SEQ ID NO. 24,
CDR2' as shown in SEQ ID NO. 25, and
CDR3' as shown in SEQ ID NO. 26 or
the heavy chain has a heavy chain variable region comprising the following three complementary determining regions or CDRs:
CDR1 as shown in SEQ ID NO. 1,
CDR2 as shown in SEQ ID NO. 2, and
CDR3 as shown in SEQ ID NO. 3; wherein the sixth amino acid of CDR2 is mutated to Q or the seventh amino acid of CDR2 is mutated to A; and
the light chain has a light chain variable region comprising the following three complementarity determining regions or CDRs:
CDR1' as shown in SEQ ID NO. 4,
CDR2' as shown in SEQ ID NO. 5, and
CDR3' as shown in SEQ ID NO. 6;
or
the heavy chain has a heavy chain variable region comprising the following three complementary determining regions or CDRs:
CDR1 as shown in SEQ ID NO. 1,
CDR2 as shown in SEQ ID NO. 2, and
CDR3 as shown in SEQ ID NO. 3; and
the light chain has a light chain variable region comprising the following three complementarity determining regions or CDRs:
CDR1' as shown in SEQ ID NO. 4,
CDR2' as shown in SEQ ID NO. 5, and
CDR3' as shown in SEQ ID NO. 6; wherein the seventh amino acid of CDR2' is mutated to S;
or
the heavy chain has a heavy chain variable region comprising the following three complementary determining regions or CDRs:
CDR1 as shown in SEQ ID NO. 1,
CDR2 as shown in SEQ ID NO. 2, and
CDR3 as shown in SEQ ID NO. 3; wherein the sixth amino acid of CDR2 is mutated to Q; and
the light chain has a light chain variable region comprising the following three complementarity determining regions or CDRs:
CDR1' as shown in SEQ ID NO. 4,
CDR2' as shown in SEQ ID NO. 5, and
CDR3' as shown in SEQ ID NO. 6; wherein the seventh amino acid of CDR2' is mutated to S;
or
the heavy chain has a heavy chain variable region comprising the following three complementary determining regions or CDRs:
CDR1 as shown in SEQ ID NO. 21,
CDR2 as shown in SEQ ID NO. 22, and
CDR3 as shown in SEQ ID NO. 23; wherein the sixth amino acid of CDR2 is mutated to Q or the seventh amino acid of CDR2 is mutated to A; and
the light chain has a light chain variable region comprising the following three complementarity determining regions or CDRs:
CDR1' as shown in SEQ ID NO. 24,
CDR2' as shown in SEQ ID NO. 25, and
CDR3' as shown in SEQ ID NO. 26.

2. A recombinant protein which comprises:
(i) the antibody of claim 1; and
(ii) an optional tag sequence that assists expression and/or purification.

3. A CAR construct comprising a scFv segment of a monoclonal antibody that specifically binds to CD73, wherein the scFv segment of the monoclonal antibody antigen binding region of the CAR construct is a binding region that specifically binds to CD73, and
the scFv has a heavy chain variable region comprising the following three complementarity determining regions or CDRs:
CDR1 as shown in SEQ ID NO. 10,
CDR2 as shown in SEQ ID NO. 11, and
CDR3 as shown in SEQ ID NO. 12; and
a light chain variable region comprising the following three complementarity determining regions or CDRs:
CDR1' as shown in SEQ ID NO. 13,
CDR2' as shown in SEQ ID NO. 14, and
CDR3' as shown in SEQ ID NO. 15;
or
the scFv has a heavy chain variable region comprising the following three complementarity determining regions or CDRs:
CDR1 as shown in SEQ ID NO. 1,
CDR2 as shown in SEQ ID NO. 2, and
CDR3 as shown in SEQ ID NO. 3; and
a light chain variable region comprising the following three complementarity determining regions or CDRs:
CDR1' as shown in SEQ ID NO. 4,
CDR2' as shown in SEQ ID NO. 5, and
CDR3' as shown in SEQ ID NO. 6;
or
the scFv has a heavy chain variable region comprising the following three complementarity determining regions or CDRs:
CDR1 as shown in SEQ ID NO. 21,
CDR2 as shown in SEQ ID NO. 22, and
CDR3 as shown in SEQ ID NO. 23; and
a light chain variable region comprising the following three complementarity determining regions or CDRs:
CDR1' as shown in SEQ ID NO. 24,
CDR2' as shown in SEQ ID NO. 25, and
CDR3' as shown in SEQ ID NO. 26 or
the heavy chain has a heavy chain variable region comprising the following three complementary determining regions or CDRs:
CDR1 as shown in SEQ ID NO. 1,
CDR2 as shown in SEQ ID NO. 2, and
CDR3 as shown in SEQ ID NO. 3; wherein the sixth amino acid of CDR2 is mutated to Q or the seventh amino acid of CDR2 is mutated to A; and
the light chain has a light chain variable region comprising the following three complementarity determining regions or CDRs:
CDR1' as shown in SEQ ID NO. 4,
CDR2' as shown in SEQ ID NO. 5, and
CDR3' as shown in SEQ ID NO. 6;
or
the heavy chain has a heavy chain variable region comprising the following three complementary determining regions or CDRs:
CDR1 as shown in SEQ ID NO. 1,
CDR2 as shown in SEQ ID NO. 2, and
CDR3 as shown in SEQ ID NO. 3; and
the light chain has a light chain variable region comprising the following three complementarity determining regions or CDRs:

CDR1' as shown in SEQ ID NO. 4,
CDR2' as shown in SEQ ID NO. 5, and
CDR3' as shown in SEQ ID NO. 6; wherein the seventh amino acid of CDR2' is mutated to S;
or
the heavy chain has a heavy chain variable region comprising the following three complementary determining regions or CDRs:
CDR1 as shown in SEQ ID NO. 1,
CDR2 as shown in SEQ ID NO. 2, and
CDR3 as shown in SEQ ID NO. 3; wherein the sixth amino acid of CDR2 is mutated to Q; and
the light chain has a light chain variable region comprising the following three complementarity determining regions or CDRs:
CDR1' as shown in SEQ ID NO. 4,
CDR2' as shown in SEQ ID NO. 5, and
CDR3' as shown in SEQ ID NO. 6; wherein the seventh amino acid of CDR2' is mutated to S;
or
the heavy chain has a heavy chain variable region comprising the following three complementary determining regions or CDRs:
CDR1 as shown in SEQ 1D NO. 21,
CDR2 as shown in SEQ ID NO. 22, and
CDR3 as shown in SEQ ID NO. 23; wherein the sixth amino acid of CDR2 is mutated to Q or the seventh amino acid of CDR2 is mutated to A; and
the light chain has a light chain variable region comprising the following three complementarity determining regions or CDRs:
CDR1' as shown in SEQ ID NO. 24,
CDR2' as shown in SEQ ID NO. 25, and
CDR3' as shown in SEQ ID NO. 26.

4. A recombinant immune cell expressing an exogenous CAR construct of claim 3.

5. An antibody-drug conjugate which comprises:
(a) the antibody of claim 1; and
(b) a coupling moiety coupled to the antibody moiety, and the coupling moiety is selected from the group consisting of a detectable label, a drug, a toxin, a cytokine, a radionuclide, an enzyme, and a combination thereof.

6. The antibody-drug conjugate of claim 5, wherein the antibody-drug conjugate ADC is as shown in the following molecular formula:

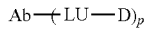

$$Ab-(LU-D)_p$$

wherein:
Ab is an anti-CD73 antibody,
LU is a linker (also called connector);
D is a drug;
and the subscript p is a value selected from 1-10.

7. The antibody-drug conjugate of claim 6, wherein the LU is selected from the group consisting of: 6-maleimido-caproyl-valine-citrulline-p-aminobenzyloxycarbonyl (MC-val-cit-PAB), 6-maleimidocaproyl-alanine-phenylalanine-p-aminobenzyloxycarbonyl (MC-ala-phe-PAB), maleimidopropionyl-valine-citrulline-p-aminobenzyloxycarbonyl (MP-val-cit-PAB), maleimidopropionyl-alanine-phenylalanine-p-aminobenzyloxycarbonyl (MP-ala-phe-PAB), N-succinimidyl 4-(2-pyridylthio)pentanoate (SPP), N-succinimidyl 4-(N-maleimidomethyl)cyclohexane-1-carboxylate (SMCC), 4-(2-pyridyldithio)butanoic acid N-hydrosuccinimide ester (SPDB), N-succinimidyl (4-iodo-acetyl)aminobenzoate (SIAB) and disubstituted maleimide linker.

8. The antibody-drug conjugate of claim 6, wherein D is selected from the group consisting of:
(i) maytansine, maytansinoid, auristatin, dorastatin;
(ii) Monomethyl auristatin E (MMAE), Monomethyl auristatin F (MMAF), Monomethyl Dolastatin 10 (MMAD); and
(iii) a DNA damage drug.

9. The antibody-drug conjugate of claim 5, wherein the heavy chain variable region sequence of the antibody is selected from the group consisting of: SEQ ID NO. 7, SEQ ID NO. 16, SEQ ID NO. 17, SEQ ID NO. 18, SEQ ID NO. 27, SEQ ID NO. 28, SEQ ID NO. 29, SEQ ID NO. 31, SEQ ID NO. 32, SEQ ID NO. 33, SEQ ID NO. 34, SEQ ID NO. 35, SEQ ID NO. 45, SEQ ID NO. 46, SEQ ID NO. 38, SEQ ID NO. 39, SEQ ID NO. 40, and SEQ ID NO. 41; and
the light chain variable region sequence of the antibody is selected from the group consisting of: SEQ ID NO. 8, SEQ ID NO. 9, SEQ ID NO. 19, SEQ ID NO. 20, SEQ ID NO. 30, SEQ ID NO. 36, SEQ ID NO. 47, SEQ ID NO. 37, SEQ ID NO. 42, SEQ ID NO. 43, and SEQ ID NO. 44.

10. The antibody-drug conjugate of claim 5, wherein the wherein the antibodies comprise wherein the antibodies respectively comprise the heavy chain variable region (VH) sequences and light chain variable region (VL) sequences as shown below:

| Names of antibodies | VH SEQ ID NO: | VL SEQ ID NO: |
|---|---|---|
| mAb001c | 7 | 8 |
| mAb001c-VK-SGS | 7 | 9 |
| mAb002c | 16 | 19 |
| mAb002c-VH-QG | 17 | 19 |
| mAb002c-VH-NA | 18 | 19 |
| mAb002c-VK-SG | 16 | 20 |
| mAb002c-VH-QG, VK-SG | 17 | 20 |
| mAb004c | 27 | 30 |
| mAb004c-VH-QG | 28 | 30 |
| mAb004c-VH-NA | 29 | 30 |
| Hu001c-14 | 31 | 36 |
| Hu001c-15 | 31 | 37 |
| Hu001c-21 | 32 | 36 |
| Hu001c-22 | 33 | 36 |
| Hu001c-23 | 34 | 36 |
| Hu001c-24 | 35 | 36 |
| Hu001c-25 | 32 | 37 |
| Hu001c-28 | 35 | 37 |
| Hu001c-30 | 46 | 47 |
| Hu001c-31 | 45 | 36 |
| Hu001c-32 | 46 | 36 |
| Hu002c-2 | 38 | 42 |
| Hu002c-3 | 38 | 43 |
| Hu002c-4 | 38 | 44 |
| Hu002c-6 | 39 | 42 |
| Hu002c-7 | 39 | 43 |
| Hu002c-8 | 39 | 44 |
| Hu002c-10 | 40 | 42 |
| Hu002c-11 | 40 | 43 |
| Hu002c-12 | 40 | 44 |
| Hu002c-14 | 41 | 42 |
| Hu002c-15 | 41 | 43 |
| Hu002c-16 | 41 | 44. |

11. A pharmaceutical composition comprising:
(i) the antibody of claim 1, an antibody-drug conjugate of the antibody, and a combination thereof; and
(ii) a pharmaceutically acceptable carrier.

12. A method for inhibiting tumor cell growth and migration, comprising the steps of: administering the antibody of claim 1 or an antibody-drug conjugate of the antibody, a CAR-T cell expressing the antibody, and a combination thereof to a subject in need.

\* \* \* \* \*

SEQUENCE LISTING

<160> NUMBER OF SEQ ID NOS: 50

<210> SEQ ID NO 1
<211> LENGTH: 5
<212> TYPE: PRT
<213> ORGANISM: Mus musculus

<400> SEQUENCE: 1

Asn Tyr Tyr Ile Tyr
1               5

<210> SEQ ID NO 2
<211> LENGTH: 17
<212> TYPE: PRT
<213> ORGANISM: Mus musculus

<400> SEQUENCE: 2

Trp Ile Tyr Pro Gly Asn Leu Asn Ile Lys Tyr Asn Glu Lys Phe Lys
1               5                   10                  15

Gly

<210> SEQ ID NO 3
<211> LENGTH: 9
<212> TYPE: PRT
<213> ORGANISM: Mus musculus

<400> SEQUENCE: 3

Asp Asp Asn Tyr Ala Trp Phe Ala Tyr
1               5

<210> SEQ ID NO 4
<211> LENGTH: 11
<212> TYPE: PRT
<213> ORGANISM: Mus musculus

<400> SEQUENCE: 4

Lys Ala Ser Gln Asp Val Ser Thr Ala Val Ala
1               5                   10

<210> SEQ ID NO 5
<211> LENGTH: 7
<212> TYPE: PRT
<213> ORGANISM: Mus musculus

<400> SEQUENCE: 5

Trp Thr Asn Thr Arg His Thr
1               5

<210> SEQ ID NO 6
<211> LENGTH: 9
<212> TYPE: PRT
<213> ORGANISM: Mus musculus

<400> SEQUENCE: 6

Gln Gln His Tyr Ser Thr Pro Phe Thr
1               5

<210> SEQ ID NO 7
<211> LENGTH: 118
<212> TYPE: PRT
<213> ORGANISM: Mus musculus

<400> SEQUENCE: 7

Gln Val Gln Leu Gln Gln Ser Gly Pro Glu Leu Val Lys Pro Gly Ala

-continued

```
                1               5                  10                  15
Ser Val Arg Ile Ser Cys Lys Thr Ser Gly Tyr Thr Phe Thr Asn Tyr
                    20                  25                  30

Tyr Ile Tyr Trp Val Lys Gln Arg Pro Gly Gln Gly Leu Glu Trp Ile
                    35                  40                  45

Gly Trp Ile Tyr Pro Gly Asn Leu Asn Ile Lys Tyr Asn Glu Lys Phe
            50                  55                  60

Lys Gly Lys Ser Thr Leu Thr Ala Asp Lys Ser Ser Ser Thr Ala Phe
65                  70                  75                  80

Met Gln Leu Ser Ser Leu Thr Ser Glu Asp Ser Ala Val Tyr Phe Cys
                    85                  90                  95

Ala Arg Asp Asp Asn Tyr Ala Trp Phe Ala Tyr Trp Gly Gln Gly Thr
                    100                 105                 110

Leu Val Thr Val Ser Ser
            115
```

<210> SEQ ID NO 8
<211> LENGTH: 107
<212> TYPE: PRT
<213> ORGANISM: Mus musculus

<400> SEQUENCE: 8

```
                1               5                  10                  15
Asp Ile Val Met Thr Gln Ser His Lys Phe Met Ser Thr Ser Ile Gly

Asp Arg Val Ser Ile Thr Cys Lys Ala Ser Gln Asp Val Ser Thr Ala
                    20                  25                  30

Val Ala Trp Tyr Gln Gln Lys Pro Gly Gln Ser Pro Lys Leu Leu Ile
                    35                  40                  45

Tyr Trp Thr Asn Thr Arg His Thr Gly Val Pro Asp Arg Phe Thr Gly
            50                  55                  60

Asn Thr Ser Gly Thr Glu His Thr Leu Thr Ile Ser Ser Val Gln Ala
65                  70                  75                  80

Glu Asp Leu Ala Leu Tyr Tyr Cys Gln Gln His Tyr Ser Thr Pro Phe
                    85                  90                  95

Thr Phe Gly Ser Gly Thr Thr Leu Glu Ile Lys
            100                 105
```

<210> SEQ ID NO 9
<211> LENGTH: 107
<212> TYPE: PRT
<213> ORGANISM: Artificial Sequence
<220> FEATURE:
<223> OTHER INFORMATION: mAb001-VL-SGS

<400> SEQUENCE: 9

```
                1               5                  10                  15
Asp Ile Val Met Thr Gln Ser His Lys Phe Met Ser Thr Ser Ile Gly

Asp Arg Val Ser Ile Thr Cys Lys Ala Ser Gln Asp Val Ser Thr Ala
                    20                  25                  30

Val Ala Trp Tyr Gln Gln Lys Pro Gly Gln Ser Pro Lys Leu Leu Ile
                    35                  40                  45

Tyr Trp Thr Asn Thr Arg His Thr Gly Val Pro Asp Arg Phe Thr Gly
            50                  55                  60

Ser Gly Ser Gly Thr Glu His Thr Leu Thr Ile Ser Ser Val Gln Ala
65                  70                  75                  80

Glu Asp Leu Ala Leu Tyr Tyr Cys Gln Gln His Tyr Ser Thr Pro Phe
                    85                  90                  95
```

```
Thr Phe Gly Ser Gly Thr Thr Leu Glu Ile Lys
            100                 105
```

```
<210> SEQ ID NO 10
<211> LENGTH: 5
<212> TYPE: PRT
<213> ORGANISM: Mus musculus

<400> SEQUENCE: 10

Ser Tyr Trp Met His
1               5

<210> SEQ ID NO 11
<211> LENGTH: 17
<212> TYPE: PRT
<213> ORGANISM: Mus musculus

<400> SEQUENCE: 11

Glu Ile Asn Pro Ser Asn Gly Arg Ser Asn Tyr Asn Glu Lys Phe Lys
1               5                   10                  15

Ser

<210> SEQ ID NO 12
<211> LENGTH: 10
<212> TYPE: PRT
<213> ORGANISM: Mus musculus

<400> SEQUENCE: 12

Arg Gly Val Ser Gly Asn Tyr Phe Asp Tyr
1               5                   10

<210> SEQ ID NO 13
<211> LENGTH: 11
<212> TYPE: PRT
<213> ORGANISM: Mus musculus

<400> SEQUENCE: 13

Lys Ala Ser Gln Asp Ile Asn Thr Tyr Leu Ser
1               5                   10

<210> SEQ ID NO 14
<211> LENGTH: 7
<212> TYPE: PRT
<213> ORGANISM: Mus musculus

<400> SEQUENCE: 14

Arg Ser Asn Ile Leu Val Asp
1               5

<210> SEQ ID NO 15
<211> LENGTH: 9
<212> TYPE: PRT
<213> ORGANISM: Mus musculus

<400> SEQUENCE: 15

Leu Gln Tyr Asp Glu Phe Pro Tyr Thr
1               5

<210> SEQ ID NO 16
<211> LENGTH: 119
<212> TYPE: PRT
<213> ORGANISM: Mus musculus

<400> SEQUENCE: 16
```

Gln Val Gln Leu Gln Gln Pro Gly Ala Glu Leu Val Lys Pro Gly Ala
1               5                   10                  15

Ser Val Arg Leu Ser Cys Lys Ala Ser Gly Tyr Thr Leu Thr Ser Tyr
            20                  25                  30

Trp Met His Trp Val Lys Lys Arg Pro Gly Gln Gly Leu Glu Trp Ile
        35                  40                  45

Gly Glu Ile Asn Pro Ser Asn Gly Arg Ser Asn Tyr Asn Glu Lys Phe
    50                  55                  60

Lys Ser Lys Ala Thr Leu Thr Val Asp Arg Ser Ser Thr Val Tyr
65                  70                  75                  80

Met Gln Leu Gly Ser Leu Thr Ser Glu Asp Ser Ala Val Tyr Tyr Cys
                85                  90                  95

Ala Arg Arg Gly Val Ser Gly Asn Tyr Phe Asp Tyr Trp Gly Gln Gly
                100                 105                 110

Thr Thr Leu Thr Val Ser Ser
            115

<210> SEQ ID NO 17
<211> LENGTH: 119
<212> TYPE: PRT
<213> ORGANISM: Artificial Sequence
<220> FEATURE:
<223> OTHER INFORMATION: mAb002-VH-QG

<400> SEQUENCE: 17

Gln Val Gln Leu Gln Gln Pro Gly Ala Glu Leu Val Lys Pro Gly Ala
1               5                   10                  15

Ser Val Arg Leu Ser Cys Lys Ala Ser Gly Tyr Thr Leu Thr Ser Tyr
            20                  25                  30

Trp Met His Trp Val Lys Lys Arg Pro Gly Gln Gly Leu Glu Trp Ile
        35                  40                  45

Gly Glu Ile Asn Pro Ser Gln Gly Arg Ser Asn Tyr Asn Glu Lys Phe
    50                  55                  60

Lys Ser Lys Ala Thr Leu Thr Val Asp Arg Ser Ser Thr Val Tyr
65                  70                  75                  80

Met Gln Leu Gly Ser Leu Thr Ser Glu Asp Ser Ala Val Tyr Tyr Cys
                85                  90                  95

Ala Arg Arg Gly Val Ser Gly Asn Tyr Phe Asp Tyr Trp Gly Gln Gly
                100                 105                 110

Thr Thr Leu Thr Val Ser Ser
            115

<210> SEQ ID NO 18
<211> LENGTH: 119
<212> TYPE: PRT
<213> ORGANISM: Artificial Sequence
<220> FEATURE:
<223> OTHER INFORMATION: mAb002-VH-NA

<400> SEQUENCE: 18

Gln Val Gln Leu Gln Gln Pro Gly Ala Glu Leu Val Lys Pro Gly Ala
1               5                   10                  15

Ser Val Arg Leu Ser Cys Lys Ala Ser Gly Tyr Thr Leu Thr Ser Tyr
            20                  25                  30

Trp Met His Trp Val Lys Lys Arg Pro Gly Gln Gly Leu Glu Trp Ile
        35                  40                  45

Gly Glu Ile Asn Pro Ser Asn Ala Arg Ser Asn Tyr Asn Glu Lys Phe

```
            50                  55                  60

Lys Ser Lys Ala Thr Leu Thr Val Asp Arg Ser Ser Thr Val Tyr
 65                  70                  75                  80

Met Gln Leu Gly Ser Leu Thr Ser Glu Asp Ser Ala Val Tyr Tyr Cys
                     85                  90                  95

Ala Arg Arg Gly Val Ser Gly Asn Tyr Phe Asp Tyr Trp Gly Gln Gly
                100                 105                 110

Thr Thr Leu Thr Val Ser Ser
            115

<210> SEQ ID NO 19
<211> LENGTH: 107
<212> TYPE: PRT
<213> ORGANISM: Mus musculus

<400> SEQUENCE: 19

Asp Ile Lys Met Thr Gln Ser Pro Ser Ser Met Tyr Ala Ser Leu Gly
  1               5                  10                  15

Glu Arg Val Thr Met Thr Cys Lys Ala Ser Gln Asp Ile Asn Thr Tyr
                 20                  25                  30

Leu Ser Trp Phe Gln Gln Lys Pro Gly Lys Ser Pro Lys Thr Leu Ile
             35                  40                  45

Tyr Arg Ser Asn Ile Leu Val Asp Gly Val Pro Ser Arg Phe Ser Gly
 50                  55                  60

Ser Arg Ser Gly Gln Asp Tyr Tyr Leu Thr Ile Thr Ser Leu Glu Tyr
 65                  70                  75                  80

Glu Asp Met Gly Ile Tyr Tyr Cys Leu Gln Tyr Asp Glu Phe Pro Tyr
                 85                  90                  95

Thr Phe Gly Gly Gly Thr Lys Leu Glu Leu Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: mAb002-VL-SG

<400> SEQUENCE: 20

Asp Ile Lys Met Thr Gln Ser Pro Ser Ser Met Tyr Ala Ser Leu Gly
  1               5                  10                  15

Glu Arg Val Thr Met Thr Cys Lys Ala Ser Gln Asp Ile Asn Thr Tyr
                 20                  25                  30

Leu Ser Trp Phe Gln Gln Lys Pro Gly Lys Ser Pro Lys Thr Leu Ile
             35                  40                  45

Tyr Arg Ser Asn Ile Leu Val Ser Gly Val Pro Ser Arg Phe Ser Gly
 50                  55                  60

Ser Arg Ser Gly Gln Asp Tyr Tyr Leu Thr Ile Thr Ser Leu Glu Tyr
 65                  70                  75                  80

Glu Asp Met Gly Ile Tyr Tyr Cys Leu Gln Tyr Asp Glu Phe Pro Tyr
                 85                  90                  95

Thr Phe Gly Gly Gly Thr Lys Leu Glu Leu Lys
            100                 105

<210> SEQ ID NO 21
<211> LENGTH: 5
<212> TYPE: PRT
<213> ORGANISM: Mus musculus
```

```
<400> SEQUENCE: 21

Asp Tyr Asn Met Asp
1               5

<210> SEQ ID NO 22
<211> LENGTH: 17
<212> TYPE: PRT
<213> ORGANISM: Mus musculus

<400> SEQUENCE: 22

Asp Ile Asn Pro Asn Asn Gly Gly Ser Val Tyr Asn Gln Lys Phe Lys
1               5                   10                  15

Gly

<210> SEQ ID NO 23
<211> LENGTH: 11
<212> TYPE: PRT
<213> ORGANISM: Mus musculus

<400> SEQUENCE: 23

Ile Thr Gly Thr Gly Tyr Trp Ser Phe Asp Val
1               5                   10

<210> SEQ ID NO 24
<211> LENGTH: 11
<212> TYPE: PRT
<213> ORGANISM: Mus musculus

<400> SEQUENCE: 24

Arg Ala Ser Glu Asn Ile Tyr Ser Asn Leu Ala
1               5                   10

<210> SEQ ID NO 25
<211> LENGTH: 7
<212> TYPE: PRT
<213> ORGANISM: Mus musculus

<400> SEQUENCE: 25

Gly Ala Thr Asn Leu Ala Glu
1               5

<210> SEQ ID NO 26
<211> LENGTH: 9
<212> TYPE: PRT
<213> ORGANISM: Mus musculus

<400> SEQUENCE: 26

Gln His Phe Trp Gly Ile Pro Trp Thr
1               5

<210> SEQ ID NO 27
<211> LENGTH: 120
<212> TYPE: PRT
<213> ORGANISM: Mus musculus

<400> SEQUENCE: 27

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
                20                  25                  30

Asn Met Asp Trp Val Lys Gln Ser His Gly Lys Ser Leu Glu Trp Ile
            35                  40                  45
```

```
Gly Asp Ile Asn Pro Asn Asn Gly Gly Ser Val Tyr Asn Gln Lys Phe
        50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Thr Ala Val Tyr Tyr Cys
                     85                  90                  95

Gly Arg Ile Thr Gly Thr Gly Tyr Trp Ser Phe Asp Val Trp Gly Thr
                100                 105                 110

Gly Thr Thr Val Thr Val Ser Pro
            115                 120

<210> SEQ ID NO 28
<211> LENGTH: 120
<212> TYPE: PRT
<213> ORGANISM: Artificial Sequence
<220> FEATURE:
<223> OTHER INFORMATION: mAb004-VH-QG

<400> SEQUENCE: 28

Glu Val Gln Leu Gln Gln Ser Gly Pro Glu Leu Val Lys Pro Gly Ala
 1               5                  10                  15

Ser Val Lys Ile Pro Cys Lys Ala Ser Gly Tyr Thr Phe Thr Asp Tyr
                20                  25                  30

Asn Met Asp Trp Val Lys Gln Ser His Gly Lys Ser Leu Glu Trp Ile
             35                  40                  45

Gly Asp Ile Asn Pro Asn Gln Gly Gly Ser Val Tyr Asn Gln Lys Phe
        50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Thr Ala Val Tyr Tyr Cys
                     85                  90                  95

Gly Arg Ile Thr Gly Thr Gly Tyr Trp Ser Phe Asp Val Trp Gly Thr
                100                 105                 110

Gly Thr Thr Val Thr Val Ser Pro
            115                 120

<210> SEQ ID NO 29
<211> LENGTH: 120
<212> TYPE: PRT
<213> ORGANISM: Artificial Sequence
<220> FEATURE:
<223> OTHER INFORMATION: mAb004-VH-NA

<400> SEQUENCE: 29

Glu Val Gln Leu Gln Gln Ser Gly Pro Glu Leu Val Lys Pro Gly Ala
 1               5                  10                  15

Ser Val Lys Ile Pro Cys Lys Ala Ser Gly Tyr Thr Phe Thr Asp Tyr
                20                  25                  30

Asn Met Asp Trp Val Lys Gln Ser His Gly Lys Ser Leu Glu Trp Ile
             35                  40                  45

Gly Asp Ile Asn Pro Asn Asn Ala Gly Ser Val Tyr Asn Gln Lys Phe
        50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Thr Ala Val Tyr Tyr Cys
                     85                  90                  95

Gly Arg Ile Thr Gly Thr Gly Tyr Trp Ser Phe Asp Val Trp Gly Thr
```

```
                    100                 105                 110
Gly Thr Thr Val Thr Val Ser Pro
            115                 120

<210> SEQ ID NO 30
<211> LENGTH: 107
<212> TYPE: PRT
<213> ORGANISM: Mus musculus

<400> SEQUENCE: 30

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Gly Ala Thr Asn Leu Ala Glu Gly Val Pro Ser Arg Phe Ser Gly
    50                  55                  60

Ser Gly Leu Gly Thr Gln Tyr Ser Leu Lys Ile Ser Ser Leu Gln Ser
65                  70                  75                  80

Glu Asp Phe Gly Ser Tyr Tyr Cys Gln His Phe Trp Gly Ile Pro Trp
                85                  90                  95

Thr Phe Gly Gly Gly Thr Lys Leu Glu Ile Lys
            100                 105

<210> SEQ ID NO 31
<211> LENGTH: 118
<212> TYPE: PRT
<213> ORGANISM: Artificial Sequence
<220> FEATURE:
<223> OTHER INFORMATION: mAb001-VH_HuG.3

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Asn Tyr
            20                  25                  30

Tyr Ile Tyr Trp Val Arg Gln Ala Pro Gly Gln Arg Leu Glu Trp Met
        35                  40                  45

Gly Trp Ile Tyr Pro Gly Asn Leu Asn Ile Lys Tyr Asn Glu Lys Phe
    50                  55                  60

Lys Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Asn Tyr Ala Trp Phe Ala Tyr Trp Gly Gln Gly Thr
            100                 105                 110

Leu Val Thr Val Ser Ser
        115

<210> SEQ ID NO 32
<211> LENGTH: 118
<212> TYPE: PRT
<213> ORGANISM: Artificial Sequence
<220> FEATURE:
<223> OTHER INFORMATION: mAb001-VH_HuG.5

<400> SEQUENCE: 32

Gln Val Gln Leu Val Gln Ser Gly Ala Glu Val Lys Lys Pro Gly Ala
```

```
                1               5                  10                  15
            Ser Val Lys Val Ser Cys Lys Ala Ser Gly Tyr Thr Phe Thr Asn Tyr
                            20                  25                  30

Tyr Ile Tyr Trp Val Arg Gln Ala Pro Gly Gln Arg Leu Glu Trp Ile
                        35                  40                  45

Gly Trp Ile Tyr Pro Gly Asn Leu Asn Ile Lys Tyr Asn Glu Lys Phe
                    50                  55                  60

Lys Gly Arg Val Thr Ile Thr Ala Asp Lys Ser Ala Ser Thr Ala Tyr
             65                  70                  75                  80

Met Glu Leu Ser Ser Leu Arg Ser Glu Asp Thr Ala Val Tyr Tyr Cys
                            85                  90                  95

Ala Arg Asp Asp Asn Tyr Ala Trp Phe Ala Tyr Trp Gly Gln Gly Thr
                            100                 105                 110

Leu Val Thr Val Ser Ser
                            115

<210> SEQ ID NO 33
<211> LENGTH: 118
<212> TYPE: PRT
<213> ORGANISM: Artificial Sequence
<220> FEATURE:
<223> OTHER INFORMATION: mAb001-VH_HuG.6

<400> SEQUENCE: 33

Gln Val Gln Leu Val Gln Ser Gly Ala Glu Val Lys Lys Pro Gly Ala
             1               5                  10                  15

Ser Val Lys Val Ser Cys Lys Ala Ser Gly Tyr Thr Phe Thr Asn Tyr
                            20                  25                  30

Tyr Ile Tyr Trp Val Lys Gln Arg Pro Gly Gln Arg Leu Glu Trp Ile
                        35                  40                  45

Gly Trp Ile Tyr Pro Gly Asn Leu Asn Ile Lys Tyr Asn Glu Lys Phe
                    50                  55                  60

Lys Gly Arg Val Thr Ile Thr Ala Asp Lys Ser Ala Ser Thr Ala Tyr
             65                  70                  75                  80

Met Glu Leu Ser Ser Leu Arg Ser Glu Asp Thr Ala Val Tyr Tyr Cys
                            85                  90                  95

Ala Arg Asp Asp Asn Tyr Ala Trp Phe Ala Tyr Trp Gly Gln Gly Thr
                            100                 105                 110

Leu Val Thr Val Ser Ser
                            115

<210> SEQ ID NO 34
<211> LENGTH: 118
<212> TYPE: PRT
<213> ORGANISM: Artificial Sequence
<220> FEATURE:
<223> OTHER INFORMATION: mAb001-VH_HuG.7

<400> SEQUENCE: 34

Gln Val Gln Leu Val Gln Ser Gly Ala Glu Val Lys Lys Pro Gly Ala
             1               5                  10                  15

Ser Val Lys Val Ser Cys Lys Ala Ser Gly Tyr Thr Phe Thr Asn Tyr
                            20                  25                  30

Tyr Ile Tyr Trp Val Lys Gln Arg Pro Gly Gln Gly Leu Glu Trp Ile
                        35                  40                  45

Gly Trp Ile Tyr Pro Gly Asn Leu Asn Ile Lys Tyr Asn Glu Lys Phe
                    50                  55                  60
```

```
Lys Gly Arg Val Thr Ile Thr Ala Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Asp Asn Tyr Ala Trp Phe Ala Tyr Trp Gly Gln Gly Thr
            100                 105                 110

Leu Val Thr Val Ser Ser
            115

<210> SEQ ID NO 35
<211> LENGTH: 118
<212> TYPE: PRT
<213> ORGANISM: Artificial Sequence
<220> FEATURE:
<223> OTHER INFORMATION: mAb001-VH_HuG.8

<400> SEQUENCE: 35

Gln Val Gln Leu Val Gln Ser Gly Ala Glu Val Lys Lys Pro Gly Ala
  1               5                  10                  15

Ser Val Lys Val Ser Cys Lys Thr Ser Gly Tyr Thr Phe Thr Asn Tyr
                 20                  25                  30

Tyr Ile Tyr Trp Val Lys Gln Arg Pro Gly Gln Gly Leu Glu Trp Ile
             35                  40                  45

Gly Trp Ile Tyr Pro Gly Asn Leu Asn Ile Lys Tyr Asn Glu Lys Phe
 50                  55                  60

Lys Gly Arg Val Thr Ile Thr Ala Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Asp Asn Tyr Ala Trp Phe Ala Tyr Trp Gly Gln Gly Thr
            100                 105                 110

Leu Val Thr Val Ser Ser
            115

<210> SEQ ID NO 36
<211> LENGTH: 107
<212> TYPE: PRT
<213> ORGANISM: Artificial Sequence
<220> FEATURE:
<223> OTHER INFORMATION: mAb001-VK_HuG.1

<400> SEQUENCE: 36

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Trp Thr Asn Thr Arg His Thr Gly Val Pro Ser Arg Phe Ser Gly
 50                  55                  60

Ser Gly Ser Gly Thr Asp His Thr Leu Thr Ile Ser Ser Leu Gln Pro
 65                  70                  75                  80

Glu Asp Phe Ala Thr Tyr Tyr Cys Gln Gln His Tyr Ser Thr Pro Phe
                 85                  90                  95

Thr Phe Gly Gln Gly Thr Lys Leu Glu Ile Lys
            100                 105

<210> SEQ ID NO 37
```

```
<211> LENGTH: 107
<212> TYPE: PRT
<213> ORGANISM: Artificial Sequence
<220> FEATURE:
<223> OTHER INFORMATION: mAb001-VK_HuG.2

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ser Pro Lys Leu Leu Ile
        35                  40                  45

Tyr Trp Thr Asn Thr Arg His Thr Gly Val Pro Ser Arg Phe Ser Gly
50                  55                  60

Ser Gly Ser Gly Thr Asp His Thr Leu Thr Ile Ser Ser Leu Gln Pro
65                  70                  75                  80

Glu Asp Phe Ala Thr Tyr Tyr Cys Gln Gln His Tyr Ser Thr Pro Phe
                85                  90                  95

Thr Phe Gly Gln Gly Thr Lys Leu Glu Ile Lys
            100                 105

<210> SEQ ID NO 38
<211> LENGTH: 119
<212> TYPE: PRT
<213> ORGANISM: Artificial Sequence
<220> FEATURE:
<223> OTHER INFORMATION: mAb002-VH_HuG0

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Trp Met His Trp Val Arg Gln Ala Pro Gly Gln Gly Leu Glu Trp Met
        35                  40                  45

Gly Glu Ile Asn Pro Ser Gln Gly Arg Ser Asn Tyr Asn Glu Lys Phe
50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gly Val Ser Gly Asn Tyr Phe Asp Tyr Trp Gly Gln Gly
            100                 105                 110

Thr Leu Val Thr Val Ser Ser
        115

<210> SEQ ID NO 39
<211> LENGTH: 119
<212> TYPE: PRT
<213> ORGANISM: Artificial Sequence
<220> FEATURE:
<223> OTHER INFORMATION: mAb002-VH_HuG1

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30
```

Trp Met His Trp Val Arg Gln Ala Pro Gly Gln Gly Leu Glu Trp Ile
            35                  40                  45

Gly Glu Ile Asn Pro Ser Gln Gly Arg Ser Asn Tyr Asn Glu Lys Phe
 50                  55                  60

Lys Ser Arg Val Thr Leu Thr Val Asp Arg Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Arg Gly Val Ser Gly Asn Tyr Phe Asp Tyr Trp Gly Gln Gly
                100                 105                 110

Thr Leu Val Thr Val Ser Ser
        115

<210> SEQ ID NO 40
<211> LENGTH: 119
<212> TYPE: PRT
<213> ORGANISM: Artificial Sequence
<220> FEATURE:
<223> OTHER INFORMATION: mAb002-VH_HuG2

<400> SEQUENCE: 40

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Leu Thr Ser Tyr
                 20                  25                  30

Trp Met His Trp Val Arg Gln Ala Pro Gly Gln Gly Leu Glu Trp Ile
            35                  40                  45

Gly Glu Ile Asn Pro Ser Gln Gly Arg Ser Asn Tyr Asn Glu Lys Phe
 50                  55                  60

Lys Ser Lys Val Thr Leu Thr Val Asp Arg Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Arg Gly Val Ser Gly Asn Tyr Phe Asp Tyr Trp Gly Gln Gly
                100                 105                 110

Thr Leu Val Thr Val Ser Ser
        115

<210> SEQ ID NO 41
<211> LENGTH: 119
<212> TYPE: PRT
<213> ORGANISM: Artificial Sequence
<220> FEATURE:
<223> OTHER INFORMATION: mAb002-VH_HuG3

<400> SEQUENCE: 41

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Leu Thr Ser Tyr
                 20                  25                  30

Trp Met His Trp Val Lys Lys Ala Pro Gly Gln Gly Leu Glu Trp Ile
            35                  40                  45

Gly Glu Ile Asn Pro Ser Gln Gly Arg Ser Asn Tyr Asn Glu Lys Phe
 50                  55                  60

Lys Ser Lys Val Thr Leu Thr Val Asp Arg Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

```
Ala Arg Arg Gly Val Ser Gly Asn Tyr Phe Asp Tyr Trp Gly Gln Gly
            100                 105                 110

Thr Leu Val Thr Val Ser Ser
        115
```

<210> SEQ ID NO 42
<211> LENGTH: 107
<212> TYPE: PRT
<213> ORGANISM: Artificial Sequence
<220> FEATURE:
<223> OTHER INFORMATION: mAb002-VK_HuG1

<400> SEQUENCE: 42

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Thr Tyr
             20                  25                  30

Leu Ser Trp Phe Gln Gln Lys Pro Gly Lys Ala Pro Lys Ser Leu Ile
         35                  40                  45

Tyr Arg Ser Asn Ile Leu Val Ser Gly Val Pro Ser Arg Phe Ser Gly
 50                  55                  60

Ser Gly Ser Gly Gln Asp Tyr Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                 85                  90                  95

Thr Phe Gly Gln Gly Thr Lys Leu Glu Ile Lys
            100                 105
```

<210> SEQ ID NO 43
<211> LENGTH: 107
<212> TYPE: PRT
<213> ORGANISM: Artificial Sequence
<220> FEATURE:
<223> OTHER INFORMATION: mAb002-VK_HuG2

<400> SEQUENCE: 43

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Thr Tyr
             20                  25                  30

Leu Ser Trp Phe Gln Gln Lys Pro Gly Lys Ser Pro Lys Ser Leu Ile
         35                  40                  45

Tyr Arg Ser Asn Ile Leu Val Ser Gly Val Pro Ser Arg Phe Ser Gly
 50                  55                  60

Ser Gly Ser Gly Gln Asp Tyr Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                 85                  90                  95

Thr Phe Gly Gly Gly Thr Lys Leu Glu Ile Lys
            100                 105
```

<210> SEQ ID NO 44
<211> LENGTH: 106
<212> TYPE: PRT
<213> ORGANISM: Artificial Sequence
<220> FEATURE:
<223> OTHER INFORMATION: mAb002-VK_HuG3

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Thr Tyr
            20                  25                  30

Leu Ser Trp Phe Gln Gln Lys Pro Gly Lys Ser Pro Lys Ser Leu Ile
        35                  40                  45

Tyr Arg Ser Asn Ile Leu Val Ser Gly Val Pro Ser Arg Phe Ser Gly
    50                  55                  60

Ser Gly Ser Gly Gln Asp Tyr Thr Leu Thr Ile Ser Ser Leu Gln Pro
65              70                  75                  80

Glu Asp Phe Ala Ile Tyr Tyr Cys Leu Gln Tyr Asp Glu Phe Pro Tyr
                85                  90                  95

Thr Phe Gly Gly Gly Thr Lys Leu Glu Ile
            100                 105

<210> SEQ ID NO 45
<211> LENGTH: 118
<212> TYPE: PRT
<213> ORGANISM: Artificial Sequence
<220> FEATURE:
<223> OTHER INFORMATION: mAb001-VH_HuG.9

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Arg Leu Glu Trp Ile
        35                  40                  45

Gly Trp Ile Tyr Pro Gly Asn Leu Asn Ile Lys Tyr Asn Glu Lys Phe
    50                  55                  60

Lys Gly Arg Ser Thr Leu Thr Ala Asp Lys Ser Ala Ser Thr Ala Tyr
65              70                  75                  80

Met Glu Leu Ser Ser Leu Arg Ser Glu Asp Thr Ala Val Tyr Tyr Cys
                85                  90                  95

Ala Arg Asp Asp Asn Tyr Ala Trp Phe Ala Tyr Trp Gly Gln Gly Thr
            100                 105                 110

Leu Val Thr Val Ser Ser
        115

<210> SEQ ID NO 46
<211> LENGTH: 118
<212> TYPE: PRT
<213> ORGANISM: Artificial Sequence
<220> FEATURE:
<223> OTHER INFORMATION: mAb001-VH_HuG.10

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile Tyr Trp Val Lys Gln Pro Gly Gln Arg Leu Glu Trp Ile
        35                  40                  45

Gly Trp Ile Tyr Pro Gly Asn Leu Asn Ile Lys Tyr Asn Glu Lys Phe
    50                  55                  60

Lys Gly Arg Ser Thr Leu Thr Ala Asp Lys Ser Ala Ser Thr Ala Tyr
65              70                  75                  80
```

```
Met Glu Leu Ser Ser Leu Arg Ser Glu Asp Thr Ala Val Tyr Tyr Cys
                85                  90                  95

Ala Arg Asp Asp Asn Tyr Ala Trp Phe Ala Tyr Trp Gly Gln Gly Thr
            100                 105                 110

Leu Val Thr Val Ser Ser
        115

<210> SEQ ID NO 47
<211> LENGTH: 107
<212> TYPE: PRT
<213> ORGANISM: Artificial Sequence
<220> FEATURE:
<223> OTHER INFORMATION: mAb001-VK_HuG.0

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Trp Thr Asn Thr Arg His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Phe
                85                  90                  95

Thr Phe Gly Gln Gly Thr Lys Leu Glu Ile Lys
            100                 105

<210> SEQ ID NO 48
<211> LENGTH: 532
<212> TYPE: PRT
<213> ORGANISM: Homo sapiens

<400> SEQUENCE: 48

Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160
```

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
        275                 280                 285

Pro Glu Asp Pro Ser Ile Lys Ala Asp Ile Asn Lys Trp Arg Ile Lys
    290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Thr Asp Glu
            340                 345                 350

Met Phe Trp Asn His Val Ser Met Cys Ile Leu Asn Gly Gly Gly Ile
        355                 360                 365

Arg Ser Pro Ile Asp Glu Arg Asn Asn Gly Thr Ile Thr Trp Glu Asn
370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Val Lys Leu Asp Val
        435                 440                 445

Leu Cys Thr Lys Cys Arg Val Pro Ser Tyr Asp Pro Leu Lys Met Asp
    450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys Ala His His His His His
        515                 520                 525

His His His His
    530

<210> SEQ ID NO 49
<211> LENGTH: 117
<212> TYPE: PRT
<213> ORGANISM: Artificial Sequence
<220> FEATURE:
<223> OTHER INFORMATION: MEDI9447-VH

```
<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
                100                 105                 110

Val Thr Val Ser Ser
        115

<210> SEQ ID NO 50
<211> LENGTH: 110
<212> TYPE: PRT
<213> ORGANISM: Artificial Sequence
<220> FEATURE:
<223> OTHER INFORMATION: MEDI9447-VL

<400> SEQUENCE: 50

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asp Asn Leu Arg Leu Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu
                100                 105                 110
```